(12) United States Patent
Ranky et al.

(10) Patent No.: US 9,228,859 B2
(45) Date of Patent: Jan. 5, 2016

(54) CUSTOMIZABLE EMBEDDED SENSORS

(71) Applicant: Northeastern University, Boston, MA (US)

(72) Inventors: Richard Ranky, Ridgewood, NJ (US); Constantinos Mavroidis, Arlington, MA (US)

(73) Assignee: Northeastern University, Boston, MA (US)

( * ) Notice: Subject to any disclaimer, the term of this patent is extended or adjusted under 35 U.S.C. 154(b) by 246 days.

(21) Appl. No.: 13/627,745

(22) Filed: Sep. 26, 2012

(65) Prior Publication Data
US 2013/0079693 A1 Mar. 28, 2013

Related U.S. Application Data

(60) Provisional application No. 61/539,198, filed on Sep. 26, 2011, provisional application No. 61/650,531, filed on May 23, 2012.

(51) Int. Cl.
*B05D 3/14* (2006.01)
*A61F 5/00* (2006.01)
*G01L 3/00* (2006.01)
(Continued)

(52) U.S. Cl.
CPC *G01D 11/00* (2013.01); *G01B 7/18* (2013.01); *G01L 1/06* (2013.01); *G01L 1/127* (2013.01); *G01L 1/142* (2013.01); *G01L 9/0072* (2013.01); *G01L 9/02* (2013.01); *G01L 25/00* (2013.01); *H01L 41/29* (2013.01); *H01L 41/314* (2013.01); *A61F 2005/0188* (2013.01); *Y10T 29/49117* (2015.01)

(58) Field of Classification Search
CPC ....... H01L 41/29; H01L 41/314; G01D 11/00
USPC ............... 73/862.08, 862.321; 427/100, 97.7; 602/16, 21–29
See application file for complete search history.

(56) References Cited

U.S. PATENT DOCUMENTS 3,968,055 A 7/1976 Palmer
6,049,160 A 4/2000 Safari et al.
(Continued)

OTHER PUBLICATIONS

International Search Report and Written Opinion issued by the U.S. Patent and Trademark Office as International Searching Authority for International Application No. PCT/US2012/057316 mailed on Jan. 17, 2013 (13 pages).

*Primary Examiner* — Cachet Sellman
(74) *Attorney, Agent, or Firm* — Wilmer Cutler Pickering Hale and Dorr LLP

(57) ABSTRACT

A method of constructing a sensor includes depositing a first material in a predetermined arrangement to form a structure. The depositing results in at least one void occurring within the structure. The method further includes depositing a second material within the voids. The second material may have electrical properties that vary according to deformation of the second material. The method also includes providing electrical access to the second material to enable observation of the one or more electrical properties. A sensor includes a structure that has one or more voids distributed within the structure. The sensor also includes a material deposited within the one or more voids. The material may be characterized by one or more electrical properties such as piezoresistivity. The sensor includes a first contact electrically coupled to a first location on the material, and a second contact electrically coupled to a second location on the material.

11 Claims, 24 Drawing Sheets

(51) Int. Cl.
*G01L 3/14* (2006.01)
*G01D 11/00* (2006.01)
*H01L 41/314* (2013.01)
*H01L 41/29* (2013.01)
*G01L 9/00* (2006.01)
*G01L 9/02* (2006.01)
*G01L 25/00* (2006.01)
*G01L 1/06* (2006.01)
*G01L 1/12* (2006.01)
*G01L 1/14* (2006.01)
*G01B 7/16* (2006.01)
*A61F 5/01* (2006.01)

(56) References Cited

U.S. PATENT DOCUMENTS

| | | | | |
|---|---|---|---|---|
| 6,053,899 | A * | 4/2000 | Slanda et al. | 604/500 |
| 6,155,120 | A * | 12/2000 | Taylor | 73/862.046 |
| 6,169,605 | B1 * | 1/2001 | Penn et al. | 358/1.1 |
| 6,265,139 | B1 * | 7/2001 | Yun et al. | 430/330 |
| 7,323,634 | B2 * | 1/2008 | Speakman | 136/256 |
| 7,415,883 | B2 | 8/2008 | Kaplan | |
| 7,755,254 | B2 * | 7/2010 | Kobayashi et al. | 310/328 |
| 2009/0306801 | A1 | 12/2009 | Sivak et al. | |
| 2011/0190201 | A1 | 8/2011 | Hyde et al. | |

* cited by examiner

| Technology Description | Visual |
|---|---|
| Conductive rubber materials have been deposited on elastic Lycra substrates to create a skin-tight kinesthetic garment for biomechanics measurement. The overall material is lightweight, adheres well to the conductive rubbers, and has high elasticity which does not inhibit motion. Depending on the garment and rubber material, the vulcanizing process can sometimes require temperatures above 300°C and a press of several MPa.<br><br>The four stages of this Production process are:<br><br>• Mixture preparation<br>• Mask design<br>• Deposition<br>• Vulcanization and mask removal | 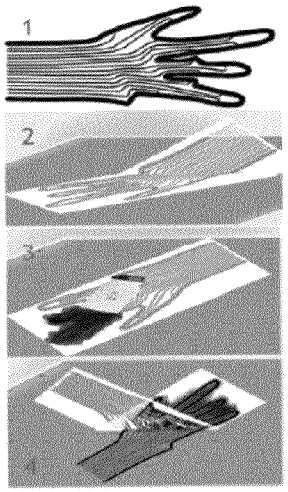 |
| The sensor at right combines using a piezoresistive micro etched silicon diaphragm and a hydrogel-filled chamber which swells in response to changes in environmental conditions like pH, $CO_2$, and Glucose. The swelling effect strains the diaphragm for the sensor output to act similarly to a strain gage. | 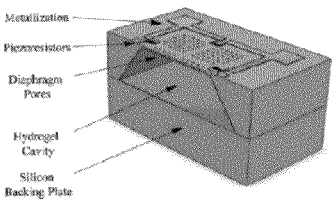 |
| At right is another example of sensor fabrication carried out via advanced silicon etching. The overall device is a 3-axis normal and shear force sensing chip and carrier chip contained under a flexible substrate, designed to interface with residual lower and upper limb. | 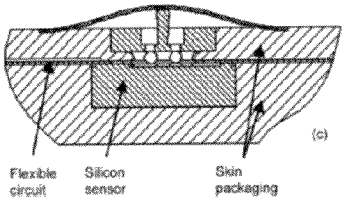 |

FIG. 11A

| Technology Description | Visual |
|---|---|
| The same sensor has also been used to evaluate cutting forces exerted by a surgical scalpel by being mounted just behind the blade (image at right). The blade is connected to a sphere-cam polyurethane shape with a flattened surface. Shear and normal forces on the blade are detected from transmission to the MEMS structure. This is an example of a modular and scalable biomechanics structure for low-cutting forces using a micro-machining techniques. | 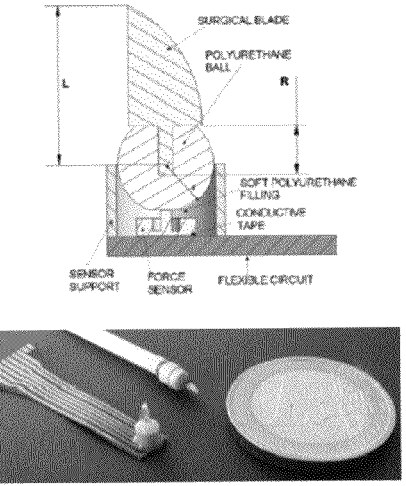 |
| The flexure at right can detect forces (0-25 mN) in 3-axes using 16 p-type integrated piezoresistors on a silicone crystal membrane, connected to wheatstone bridges. The sensor is fabricated using photolithography on front side of the wafer, with membranes on the reverse side 25 μm thick using anisotropic wet chemical etching. Piezoresistive elements have a resting resistance of are 2.26 ±0.198 kΩ. | 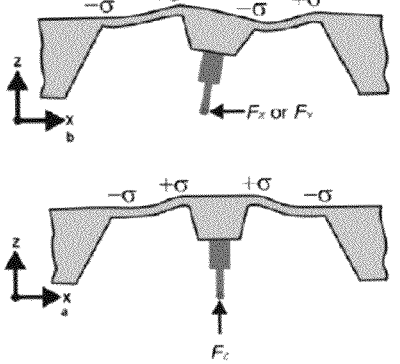 |
| Two concentric envelopes around the finger can act as a contact sensor when the conductive fluid between them is forced to move from compression (contacting the finger to an object). The conductive suspension remains in a liquid between the elastomeric skin, depending on where the ground and reference measurement electrodes are the location and magnitude of forces around the finger can be detected. Using a liquid to act as the sensing element poses challenges for leaks, air infiltration, particles settling over time, and non-uniform redistribution of the fluid. | 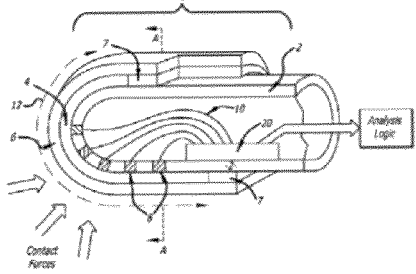 |

FIG. 11B

| Technology Description | Visual |
|---|---|
| In the image at right a 50g weight deflects the angled strut to bring the reflective surface closer to the collector. These structures can line a robotics manipulator to determine how much force is being applied, or to measure compliance of the grasped object. | 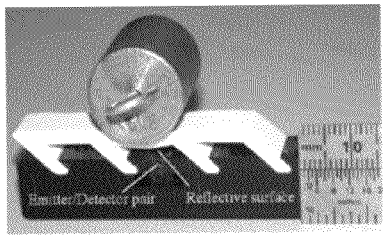 |
| The catheter at right has an embedded Infra Red sensor to measure deflection within the tip, as well as electro-magnetic sensing elements for shear loads. All components including the reflective surface on the inside of the catheter were assembled into a 6mm diameter compliant housing built using an Objet Connex500 MPJ system. The researchers report that total time to fabricate, assemble, and calibrate can be under 3 hours. However they note some challenges in using the compliant printed material for the flexure because of it hysteresis and viscoelastic behavior. | 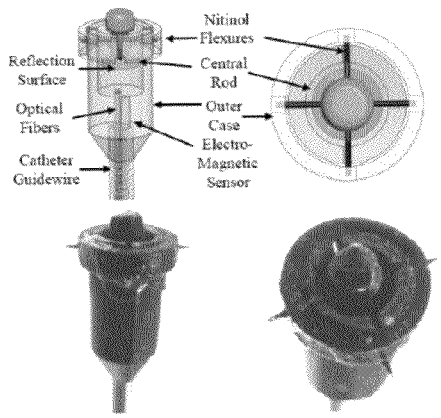 |
| For measuring interaction forces on the lower limb between the human and exoskeleton LOPES, this compliant IR based sensor lines the cuffs. This distributed approach along the soft tissue checks for comfort and safety when using the robotic assistance for gait retraining. The sensor has a compliant silicone exterior which contacts the limb, and as the flexure is compressed, it occludes the pathway between a light emitter and photodiode. Pads are roughly 20mm by 60mm to fit inside the leg cuffs. | 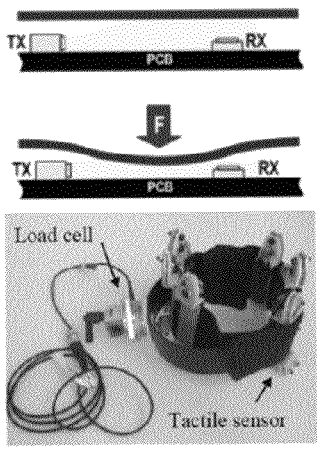 |

FIG.12A

| Technology Description | Visual |
|---|---|
| The robotic finger at right uses a Fiber Bragg Grating sensor at the tip for force measurement, assembled into a robotic device made from copper mesh and SLA materials using the Shape Deposition Modeling (SDM) process. A known wavelength of light passes through the tube (similar to a fiber optic cable) and as it is compressed from the surrounding flexure, the wavelength of light changes. Measuring this effect allows back calibration for force measurement. Tradeoffs compare embedding the tube using the specialized SDM technique but the sensor is immune to electromagnetic noise along its length. | 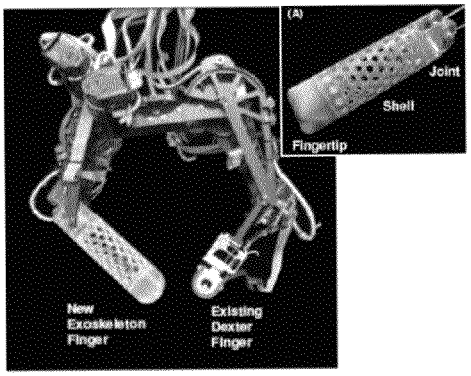 |

FIG. 12B

| Technology Description | Visual |
|---|---|
| Although resistors used in modern circuit are usually rolled carbon film, deposition of carbon directly can operate similarly. Commercial work from Optomec has been shown using an aerosol jetting process to selectively sputter an atomized carbon ink onto the exterior freeform surfaces of parts 25-30 microns wide. In the image at right it shows a wing prototype where one conductive element acts like a radio antennae and the other like as a wire to power the motor. | |
| University of Texas El Paso has hardware developed which integrates FDM and SLA hardware with direct print technology to external channels and grooves. The silver ink used has high conductivity but has only been used for rigid electronics since it cannot maintain a connection when strained. The electric dice at right act like wires with surface mount LEDs to denote the pips. | |
| NScript uses micro dispensing pumps to spray-print conformal electronics like wires and antennae onto the exterior surfaces of parts. The conductive traces are primarily either carbon (left image) or silver particles (right image) in a evaporating suspension which have high conductivity when used on rigid objects. | |
| The University of Illinois has an educational initiative to use a conductive silver ink pen for students to draw images by hand which can activate LED lights and teach students about basic electrical properties. | |

FIG. 13A

| Technology Description | Visual |
|---|---|
| Thin stretchable and conforming sensors from MC10 monitor physiological and biological signals from the body exterior for sports monitoring. The sensors and accompanying electronics are able to undergo strains in all directions several times their original length, so they can be used on highly flexible substrates like latex, leather, paper or adhere to skin. | 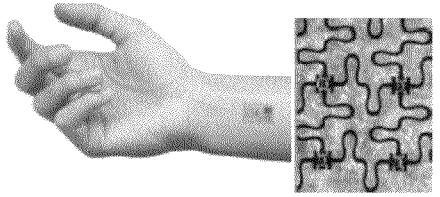 |
| The Bare project from the Royal College of Art, London is based in London uses carbon traces in suspension which can be brushed or sprayed onto the human body for artistic wearable electronics applications. The traces are non toxic and water soluble. | 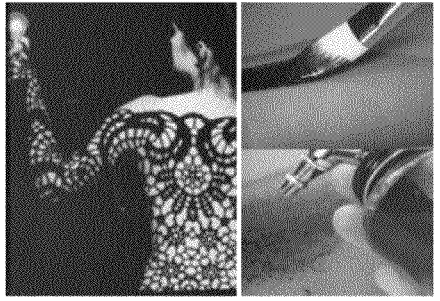 |
| Using the same operating principle as a carbon film rotary potentiometer, this design for an angular displacement (bend) sensor uses flexible material with sliding contact conductive surfaces. As the sensor is bent, the amount of conductive film between the electrodes decreases and resistance drops. Alternative embodiments have been suggested using a conductive fluid or suspension. | 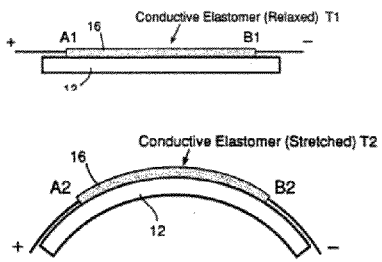 |

FIG. 13B

| Technology Description | Visual |
|---|---|
| The micro-robotics laboratory at Harvard is using MEMS-based layered fabrication to build structures which can unfold into small mobile robots. The image at right shows a complete robot with detail on the flexible layer between the structural elements [reference http://micro.seas.harvard.edu/]. | 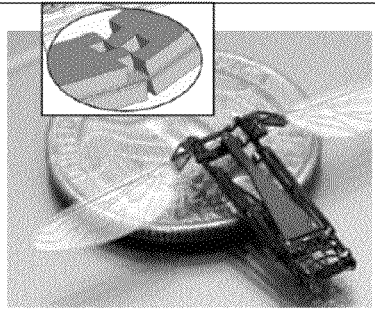 |
| Harvard Whitesides Research Group for Active soft Robotics has a design for a "Hyperelastic pressure sensor" embedded in a flexible robot. The hollow tubes can be filled with air for pneumatic actuation or filled with a conductive liquid, in this case Eutactic Gallium Indium. These hollow tubes held inside tubes arebuilt into the robot at the time of molding from silicone using positive and negative features. | 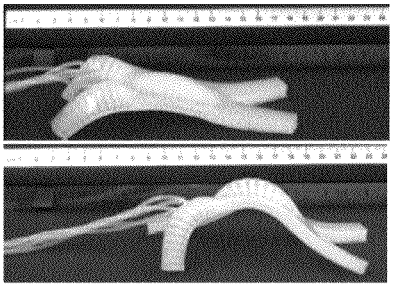 |
| Biomimetic tentacle fabricated from flexible AM materials with embedded shape memory alloy actuating elements. Its partner at the right of the image is the user-sensing element. The project intention is to create objects which respond to environmental and human actions in an art gallery setting. | 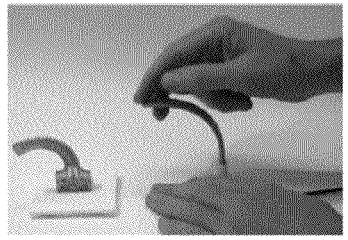 |
| Tooling for Electrode Discharge Machining (EDM) can be expensive with a short life span. The image at right shows an SLA part with conductive coating and embedded channels for circulating coolant through the part during EDM. | 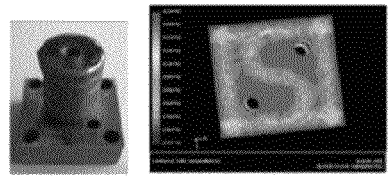 |
| Work by De Laurentis et al. has yielded robotics devices and mechanisms built in an SLA device pre-assembled and pre-sensorized by inserting the components into the resin bath during a pause in the build process. | 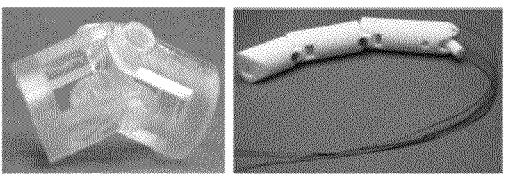 |

FIG. 15

CUSTOMIZABLE EMBEDDED SENSORS

CROSS REFERENCE TO RELATED APPLICATIONS

This application claims benefit of the following patent applications, the contents of which are hereby incorporated by reference in their entirety: U.S. Provisional Patent Application Ser. No. 61/539,198, filed Sep. 26, 2011 and U.S. Provisional Patent Application Ser. No. 61/650,531, filed May 23, 2012.

BACKGROUND

Creating custom sensorized structures for the human body can be time and cost intensive, and in many cases each particular user requires redesigning it from the start. Streamlining the capability to embed sensing elements into structures can provide greater quantitative feedback to users, medical practitioners, researchers for ergonomic comfort, patient exercise progress during a physical therapy regime, monitoring tools for patient evaluation, and assistive tools worn daily to improve quality of life.

SUMMARY OF THE INVENTION

In one aspect, the invention is a method of constructing a sensor. The method includes depositing a first material in a predetermined arrangement to form a structure. The depositing results in at least one void occurring within the structure. The method also includes depositing a second material within the voids. The second material has one or more electrical properties that vary according to deformation of the second material. The method further includes providing electrical access to the second material to enable observation of the one or more electrical properties.

In one embodiment, the depositing a first material further includes using an additive manufacturing technique. In another embodiment, the predetermined arrangement includes a sensor design. The predetermined arrangement may include a plurality of consecutive layers. Each of the consecutive layers may be a cross-sectional profile of the sensor design. The voids may be defined within the profile.

In another embodiment, the second material is a conductive elastomer. The one or more electrical properties may include piezoresistive properties. The piezoresitive properties may include a change in the electrical resistance characteristic with respect to the amount of deformation experienced by the material. The piezoresistive properties may be associated with a piezopelectric effect. The second material may be a room temperature vulcanizing silicon suspension of electrically conductive particles. The electrically conductive particles may include nickel-coated graphite particles.

In another embodiment, depositing the second material further includes injecting the second material through a port in the structure. The port may provide access to the at least one void. In one embodiment, the injecting is accomplished with a syringe. The syringe may connect to the port through a coupler that is securely fastened to the syringe and the port. The coupler may be s a Leur lock that has threads for coupling to the syringe.

In one embodiment, providing electrical access to the second material further includes attaching a first electrode to a first location on the second material and attaching a second electrode to a second location on the second material. The first location may be a first end of the second material. The second location may be a second end of the second material.

Another embodiment further includes embedding one or more electrical components in the structure. The one or more electrical components may be electrically coupled to the second material. The one or more electrical components may be an amplifier, a filter, a comparator, an electrode, a voltage regulator, a current regulator, a sampler or a buffer, or any combination of these components. In general, an component known in the art may be included in the structure.

In another aspect, the invention includes a sensor. The sensor includes a structure, and the structure may include one or more voids distributed within the structure. The sensor also includes a material deposited within the one or more voids. The material is characterized by one or more electrical properties. The sensor further includes a first contact electrically coupled to a first location on the material, and a second contact electrically coupled to a second location on the material.

In one embodiment, the structure includes a plurality of consecutive layers, each of which is a cross-sectional profile of the structure. The plurality of consecutive layers was produced using an additive manufacturing technique.

The structure may be based on a sensor design, i.e., the structure is constructed according a design plan created by a human designer, a computer-based algorithm or other automated system, or a combination thereof. In one embodiment, the sensor design describes a torque sensor. In another embodiment, the sensor design describes a force sensor. In yet another embodiment, the sensor design describes an impact sensor. In another embodiment, the sensor design describes a bend sensor. In a further embodiment, the sensor design describes a vibration sensor.

In one embodiment, the first location on the material is a first end of the material and the second location on the material is a second end of the material. In another embodiment, the one or more electrical properties includes piezoresistive properties.

In an embodiment, the material is deposited within the one or more voids by injecting the material through an opening in the structure. An adapter connecting the opening to an injector may be used. The adapter may include threads that are used to couple to the injector. The adapter may be removably coupled to the opening in the structure, so that the adapter may be detached from the opening after the material is deposited in the void. In one embodiment, the material may include graphite particles in a silicone RTV suspension.

In another aspect, the invention is an orthotic device. The orthotic device includes a structure for providing support to a portion of human anatomy. The structure may include one or more voids distributed within the structure. The orthotic device may include a material deposited within the one or more voids. The material may be characterized by a piezoresistive property. The device further includes a first contact electrically coupled to a first location on the material, and a second contact electrically coupled to a second location on the material.

In another aspect, the invention includes an ankle-foot orthosis, which a structure for providing support for one or more of a foot, ankle and lower leg. The structure may include one or more voids distributed within the structure. The orthosis also includes a material deposited within the one or more voids. The material may be characterized by a piezoresistive property. The orthosis may include a first contact electrically coupled to a first location on the material, and a second contact electrically coupled to a second location on the material.

In another aspect, the invention includes an upper extremity measuring device, which includes a structure having a first surface and a second surface. The structure may include at least one void distributed within the structure beneath the first surface and at least one void distributed in the structure beneath the second surface. The device further includes a material deposited within the voids. The material may be characterized by a piezoresistive property. For each of the voids within the structure, a first contact may be electrically coupled to a first location on the material, and a second contact may be electrically coupled to a second location on the material.

In another aspect, the invention includes a device for sensing contact with an object. The device includes a structure having an exterior surface, the structure including at a first void and a second void extending into the exterior surface. The structure includes a plurality of consecutive layers, each of which is a cross-sectional profile of the structure. The device further includes a material deposited into the voids, wherein the material is characterized by a piezoresistive property and wherein the material deposited into the first void is not in contact with the material deposited into the second void. The device also includes an electrical circuit electrically coupled to the material deposited into the first void and to the material deposited into the second void. The exterior surface contacting the object causes the electrical circuit to form a closed electrical circuit. In one embodiment, a conductive object causes the electrical circuit to form a closed electrical circuit when the conductive object is electrically coupled to the material in the first void and to the material in the second void. In another embodiment, the object causes the electrical circuit to form a closed electrical circuit when the object manipulates a cantilevered portion of the material in the first void to be electrically coupled to the material in the second void. In one embodiment, the plurality of consecutive layers was produced using an additive manufacturing technique.

In another aspect, the invention includes a device for supporting at least a portion of an electrical circuit. The device includes a structure including one or more voids distributed within the structure. The structure includes a plurality of consecutive layers, each of which is a cross-sectional profile of the structure. The device further includes a material deposited into the at least one void. The material is characterized by a piezoresistive property. The material is electrically coupled to the electrical circuit, such that the material forms at least a portion of a conductor in the electrical circuit. In one embodiment, the plurality of consecutive layers was produced using an additive manufacturing technique.

BRIEF DESCRIPTION OF DRAWINGS

The foregoing and other objects of this invention, the various features thereof, as well as the invention itself, may be more fully understood from the following description, when read together with the accompanying drawings in which:

FIGS. 11A and 11B present different research and commercially available sensor techniques that use the piezoresistive effect.

FIGS. 12A and 12B present different research and commercially available sensor techniques that use IR/optical for human biomechanics sensing.

FIGS. 13A and 13B present different research and commercially available sensor techniques that use conductive materials for human biomechanics sensing.

FIG. 15 presents different research and commercially available sensor techniques that use small scale mechatronics for human biomechanics sensing.

DETAILED DESCRIPTION

Suitable exterior regions where custom structures which need to support, sense, and interact with the body exterior can be determined based on the following four criteria:

Regions that are most utilized for the largest variety of activities of daily living.

Controlled range of motion is used daily for best quality of life.

Regions that have a large anthropometric variability—not just in terms of key measurements but of curves and surfaces.

Boney prominences where the tissue can be uncomfortable if pinched, or where loss of circulation can occur if over-compressed.

Figure 1:
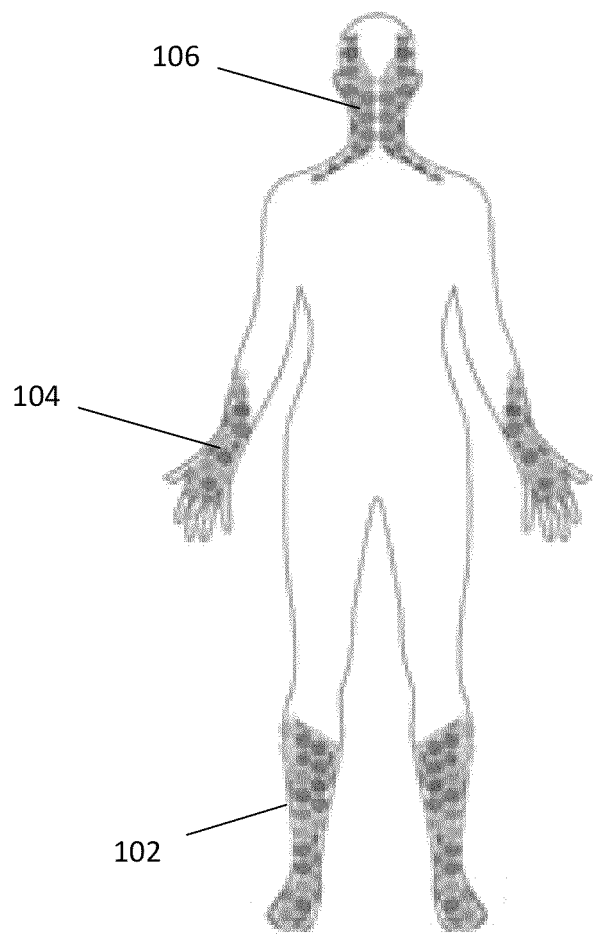
FIG. 1 shows regions of the human body that could benefit from devices which combine 3-dimensional (3D) scanning and embedded sensors.

FIG. 1 illustrates regions of the human body that could benefit from devices which combine 3-dimensional (3D) scanning and embedded sensors in, for example, an additive manufacturing structure. As shown, the ankle-foot complex 102, the wrist-hand complex 104, and the neck-head complex 106 exhibit these characteristics. The exemplary embodiments described herein generally focus on the first two regions: the distal effectors, using requirements and results of sensorized tools for the upper extremity as example sensor modalities. The head and neck complex is included within the scope of the appended claims and of this disclosure, even though the head-neck complex is not explicitly treated in the exemplary embodiments. Further, other regions of the body may also be considered to be included within the scope of the appended claims and of this disclosure, even though not explicitly treated in the exemplary embodiments.

A piezoresistive sensing phenomenon is used as the transducing element of the described embodiments. Such a transducing element has different modalities depending on what the physical phenomenon is to be sensed. A family of sensors is possible using this underlying transducing element, and examples are shown that may be used to measure force, pressure, torque, vibration, impact, and contact, among others, and combinations thereof. Additionally, the sensor design and fabrication options allow the user to tailor the sensing range depending on the application on the body and the anticipated loading magnitudes.

The described embodiments may customize the characteristics of each force sensor, for example, to the individual user and surrounding geometry in the device via two implementation modes:

Intra-Device Phenomenon:
Self-diagnostic measurements for health of the device containing the sensor, such as: impact, mechanical fatigue, device damage, device flexion. One example includes an ankle foot orthosis with embedded sensors to check for wear & tear, impact sensors detecting a force threshold.

Device-Environment Phenomenon:
Sensing interactions between the surrounding environment/person, and the device body. One example of this implementation mode includes computer-interface button device, detection of heel strike and contact in footwear, wearable medical monitoring tools, torsion and force sensors.

The described embodiments combine sensor design and device design to address needs not previously researched. Customizable force sensors have been discussed in previous work, but limited mostly to the nano and micro-scale. In order to effectively interact with the forces of a human body, meso-scale instrumentation is required. As used herein, "meso-scale" means physical dimensions able to be estimated by the naked human eye. Similarly to off-the shelf sensors, the unique geometry of the disclosed embodiments, and their scalable design requires very specific fabrication capabilities which can also easily produce a wide range of sensors—both stand-alone sensors and sensors that are embedded in the body of a device itself. This necessitates a fabrication methodology which can build highly accurate features at a small scale; hollow features & voids; thin surfaces; and is expandable for a mass customization platform. It is feasible to fabricate these structures using several methods including insertion casting, lost wax casting, 5-axis precision CNC milling, or plastic dipping.

For speed and process flexibility, the exemplary embodiments described herein utilize the technique of Additive Manufacturing (AM), also commonly referred to as 'Rapid Prototyping' or 'layered manufacturing'. AM differs from conventional subtractive fabrication methods like milling and turning because it creates three-dimensional contours and features by adding and bonding successive thin cross-sectional layers of material rather than removing material from an initial structure or deforming portions of the initial structure.

The unique advantages of AM have been adopted by medical practitioners in surgical theater as tool guides and surgical implants because of their fabrication flexibility and production speed. For the same reasons AM is also being explored as a way to build functional plastic components for the exterior of the body. Developments in non-invasive 3D scanning have made it possible to acquire digital models of freeform surfaces like the superficial contours of the human body to serve as the design references. The combination of these two technologies can provide patient-specific data input corresponding to anatomical features; as well as a means of producing a readily-instrumented patient-specific form output with electronic components already embedded. In the medical context AM sensorized devices are well suited to assist, measure & evaluate, and rehabilitate patients.

Figure 2:
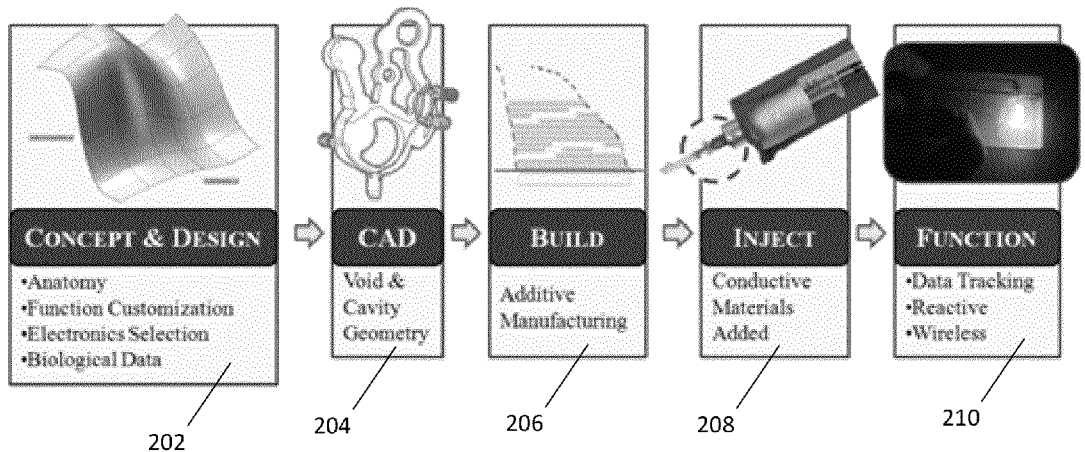
FIG. 2 shows the process of integrating design of the device with sensors and electrical wiring.

FIG. 2 shows the process of integrating design of the device with sensors and electrical wiring. The process begins with Concept and Design 202. By using a flexible fabrication like AM, the design input parameters range from anatomical landmarks and parametric equations to qualitative usability selections by the end user or medical practitioner. Following Concept and Design is computer-aided design (CAD) processing 204, during which a CAD model is generated for the structural shape with specialized cavities, voids, channels and other types of empty features (referred to herein generally as 'voids') built in to accept the conductive elements. During the Build stage 206, AM techniques are used to produce a physical manifestation of the model. Once the fabrication has been completed in the Build stage 206, these empty features (e.g., voids and cavities) are filled with a conductive material (for example a piezoresistive elastomeric suspension) during the Inject 208 stage. Depending on the specific geometry for each of the voids, once filled they will respond to mechanical stimuli differently. The complete device is then able to function 210 as it responds to interactions with the user and itself. The responses range from conducting electricity to increasing resistance from applied force, torsion, or moments, as originally planned by the selected internal geometry of the cavities.

There are over 700,000 incidences of stroke each year in the US. During the acute care phase following injury to the brain like stroke or impact trauma, physical therapy exercises for fine motor control, dexterity, and gait initiates functional recovery via neuro plasticity.

Reduced sensitivity and range of motion of the affected side of the body presents challenges in monitoring a patient to ensure that they are responding effectively to a rehabilitation regime. Assessment scales for patient recovery are based off capabilities similar to activities of daily living like turning a doorknob or opening a jar and usually include patient-based feedback on a discrete scale. A family of easily sensorized tools could compliment this process which can track patient progress in a quantifiable way. Tools which can connect to a computer or electronic storage device can record patient activities and exercises during and outside of the scheduled physical therapy sessions and have been shown to improve motor function.

For conditions remaining past acute care, long term use of assistive devices like orthoses or braces enable users to have a wider range of activities of daily living (ADL) for a higher quality of life. Such devices have user-specific features since their efficacy of these devices is affected by how well they suit the specific conditions the patient's anthropometry and iso-kinetic capabilities, which can vary significantly according to the specific motor control capabilities. By embedding sensors in these devices, clinicians will be able to monitor the wearer's daily activities in and outside of the hospital setting.

3D scanning devices digitize freeform surfaces by capturing a cloud of discrete coordinates. The points are connected to re-create surfaces of the scan target digitally. Depending on the resolution of the scan, the process can be used for industrial manufacturing quality control of dimensional accuracy and surface roughness, digitizing legacy components which have no dimensional documentation, or medical modeling where they are used as the intermediate step to fabricate anatomy via additive manufacturing. Such models have had successful implementation in preoperative planning, custom hip and knee implants, facial prosthetics post-surgery and teaching tools for patients and medical staff. For subcutaneous imaging, Computed Tomography (CT) and Magnetic Resonance Imaging (MRI) have been used to generate the points and surfaces of the target, but this discussion will focus on technology which captures superficial features only. These devices may be divided into two categories of contact and non-contact.

Contact devices physically touch the surface and register the location by deflection at the end effecter via electronic switch. Contacting touch-probes vary in their resolution from sub-millimeter scale to meso structures and are often very accurate over a wide measurement volume because they are often in the form of an end effector and articulated arm that provides a mechanical ground relative to previous measurements.

Non-contact scanners (i.e., 3D laser-based scanners) are able to capture surface geometry from a distance. Depending on the technology can be only a few centimeters from the surface, to several miles in the case of landscape mapping. For softer and more delicate structures or for very large objects (an aircraft, for example) they sweep across the field of view with light-based measurements. In some cases handheld devices use both methods to capture a larger field of view with mechanically grounded coordinates attached to the point cloud.

Figure 3:
FIG. 3 illustrates the Konica Minolta Vivid 910 Laser Scanner.

3D laser-based scanners are non-contact scanners that emit a beam oriented normal to the surface to be scanned. The light reflected back from the surface is captured as a 2D projection by an imaging device (e.g., a Charged-Couple Device (CCD) camera) and a point cloud is created using triangulation between the two cameras and the laser emitter. Laser scanners are designed for contour capture and cannot record color or texture information without an additional image to wrap around the digital surface. FIG. 3 illustrates the Konica Minolta Vivid 910 Laser Scanner, an example of a laser scanner suitable for use with the described embodiments.

Figure 4:
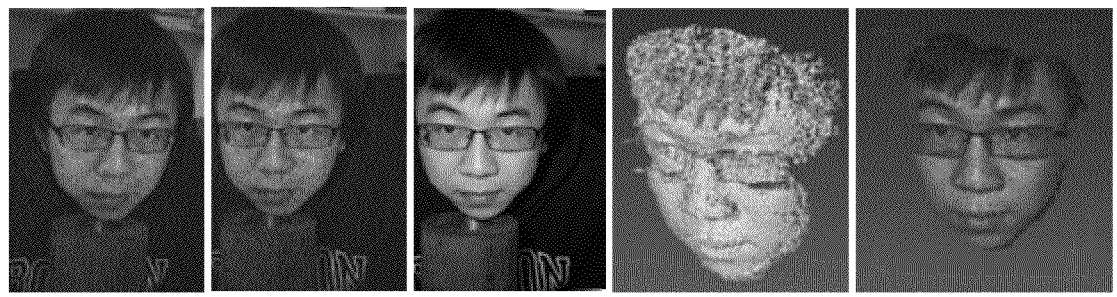
FIG. 4 shows the progression that occurs when creating a digital version of the surfaces and colors of a physical objet using non-contact stereoscopic photogrammetry.

For medical applications, most commercial laser scanners used for scanning are rated as eye safe, but reflections on curved surfaces and other inadvertent events can result in a potentially harmful focused beam. Knowing the receiver locations and orientations, lines are mathematically triangulated to produce 3D coordinates of each unobscured point in both pictures necessary to reproduce an adequate point cloud for shape and size reproduction. 3D photogrammetric scanners use images captured from different points of view to reconstruct a surface. Images are taken from at least two different known locations in order to triangulate and measure "lines of sight" for each targeted surface. The images in FIG. 4 show the progression that occurs when creating a digital version of the surfaces and colors of a physical objet using non-contact stereoscopic photogrammetry. In this case of measuring surfaces distances in three dimensions, there must be two points of reference (i.e. two camera receivers) to determine the depth of each XY coordinate. This is analogous to humans' depth perception by having two eyes. This device projects a color map onto the scan target and captures three JPEG images—one from each camera while the projected color map is on, and a single image when it is off.

To turn the point cloud into a useable reference for Computer-Aided Design (CAD), two intermediate steps take place. The first is to clean the point cloud by removing anomalies (spikes), filling holes, and decimating the cloud to reduce the file size. The second step is to fit parametric shapes on the scan surface. For applications with mechanical parts with parametric geometry it is possible to fit shapes like cylinders and cubes, but for the smooth freeform contours of organic shapes Non-Uniform Rational B-Splines (NURBS) are most appropriate.

The capabilities of designing devices and parts to fit anatomy are significantly affected by the quality of the scan data from the initial capture. Scan quality of bare skin is greatly impacted by physical characteristics of the subject, environmental conditions, and the capabilities of the hardware used. Target and lighting conditions can readily be controlled with appropriate calibration, consistent even lighting and a stable scanner mount; but the greatest variation remains with the subject. The average skin tone and hue vary from one person to the next, as well as the variation within a patch of skin. These are conditions common in medical applications which pose challenges for 3D scanners to accurately digitize superficial geometry of live human subjects. Skin allows wavelengths of light and radiation to pass through for perform vital functions (e.g., the production of vitamin D). Much of the light emitted from a 3D scanner will experience sub-surface scatter when passing through the epidermal boundary and refract or be absorbed under the skin surface which limits the number of data points registered and generates errors spikes. For high-accuracy laser scanners, the blood vessel and skin deformation from a single heartbeat may appear as two different surfaces. Voluntary motions like the subject remaining still, as well as involuntary motions like heartbeat, twitches, or trembling pose challenges for high-quality scans. For thinner anatomy like the ear lobe these effects from the circulatory system are even more prevalent and can induce small, but uncontrollable scan deviations. Optical scanners also have difficulty capturing sharp edges like individual hair follicles which scatter light in random directions away from the receiver. Large surface patches of missing data can result from excessive specular reflection, Even slight motion can cause anomalies as spikes in the mesh, and hair follicles, and certain tones can be more challenging to record.

Scan quality from projected-light 3D scanners can be sensitive to color tone and specular reflection of a scan surface. Samples had outer diameter 3 cm and leg length 2.5 cm. Scans were taken against a black matte background with leading edges 70 cm away from the central lens. The matte samples were evenly coated with Krylon Dulling Spray 1310 (Krylon Products Group, Cleveland, Ohio, USA). Glossy samples were evenly coated with Krylon UV-Resistant Clear Acrylic Gloss Coating. The matte samples have higher diffuse reflections, and the glossy samples have higher specular reflection based on the refractive index of each coating.

Under all conditions, white surfaces have the best scan quality for even surfaces. The black sections are unable to reflect sufficient light and have the largest irregularities and spikes. The high-gloss edges are difficult to register because they scatter light randomly and appear as holes. These factors must all be taken into account when designing devices to fit on the human wearers to maximize their comfort and functionality.

An object with complex freeform 3D contours can be very challenging and very costly to prototype & manufacture with traditional fabrication methods. Additive Manufacturing (AM, but also known as "Layered Fabrication", "Rapid Prototyping", "3D Printing", "Additive Fabrication", or "Layered Manufacturing") is a fabrication methodology which opens possibilities to readily fabricate these previously impossible features in a fast, accurate, and cost-effective way. Subtractive machining practices like milling and turning remove waste material until only the part features remain. AM fabricates a three-dimensional object from the base up by adding thin consecutive cross-sectional profiles of the object which bind together for a complete 3D shape. This is fixtureless fabrication since no new tooling is required and although there are many different fabrication materials, machines, and procedures worldwide; the natures of these technologies remain similar.

The unique capabilities of AM have benefited the engineering design process in reduced development time & cost, greater variety in a family designs, and prototypes more accurate to functional testing of the final device. The first RP machines began with 3D Systems in 1986, but the technology and industry have already made significant strides in development in a relatively young life. The normally long time periods between design iterations for form and fit evaluation can be significantly reduced with AM, so depending on part size it may take only a few hours to go from digital design to physical part. These factors make the technology excellent for custom parts produced to order in small quantities. Virtually all layered processes can deposit material in the horizontal plane much more rapidly than they can build up thickness. Consequently parts are typically built lying down so that their shortest overall dimension is oriented along the z-axis to optimize for build time. Parts are also frequently nested within the build chamber to maximize parts per build cycle.

Summary of Advantages Using AM in the Medical Field
  Highly accurate at small scale
  Able to build hollow features and voids
  Thin complex surfaces
  Convenient mass customization
  Consolidation of components
  Decentralized distribution network
  Complex geometry from biological and mathematical inputs
  Functional materials
  Small batch fabrication Designing parts and shapes with curved internal features and undercuts offers new advantages which are currently being researched as more efficient hydraulic cooling channels and for safer routing of electronics. This eases part consolidation since build complexity is less impactful compared to subtractive fabrication methods. Reducing the parts in the bill of materials and integrating electrical components is one benefit of embedded semiconductors using techniques of the described embodiments.

Figure 5:
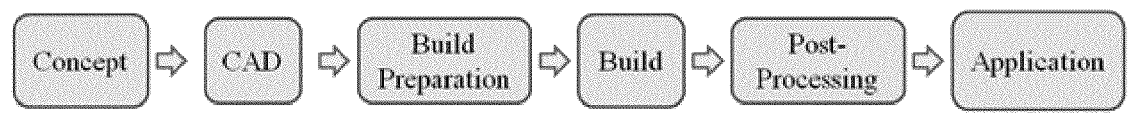
FIG. 5 illustrates generic AM processing.

Part of concurrent engineering practices is considering the method and constraints of fabrication at each phase of the design process. Traditional subtractive fabrication methods have a large emphasis on 'design for manufacturing' and anticipating these constraints early on. Although AM processes do also have materials and geometry limitations, their capabilities encourage a reverse philosophy of 'manufacture for design'. The generic AM process laid out in FIG. 5 can be a continuation of the 3D scanning process (starting at the CAD phase with parametric surfaces) or can operate independently as any other fabrication stage.

The tool paths (or in some cases laser paths) are generated from the Build preparation according to the surface geometry of the part and its support structures. The key digital step in this process is generating this surface geometry using a Standard Tessellation Language (STL) file. An STL file recreates the surface geometries of the CAD part in triangles of varying size and shape and does not contain any other design data, just measurement units and geometry. Similarly to decimating and parameterizing the 3D scan surface, the resolution of the triangles affects the file size, complexity, and physical resolution of the part to be built. For complex internal voids and features it is not only important to have a fabrication method with high enough resolution to build them, but that the STL file and build preparation are set to preserve these features and not interpolate them away. The processes described below represent the current major groupings of commercial types of AM, with each one able to build internal features in flexible plastic materials.

Stereolithography

Stereolithography (SLA) is a comparatively older technology than some of the other additive manufacturing processes, but it remains one of the most widely used methods. It was one of the first processes that could produce a part strong enough to be used as an end product rather than just a design mockup or a prototype.

Figure 6:
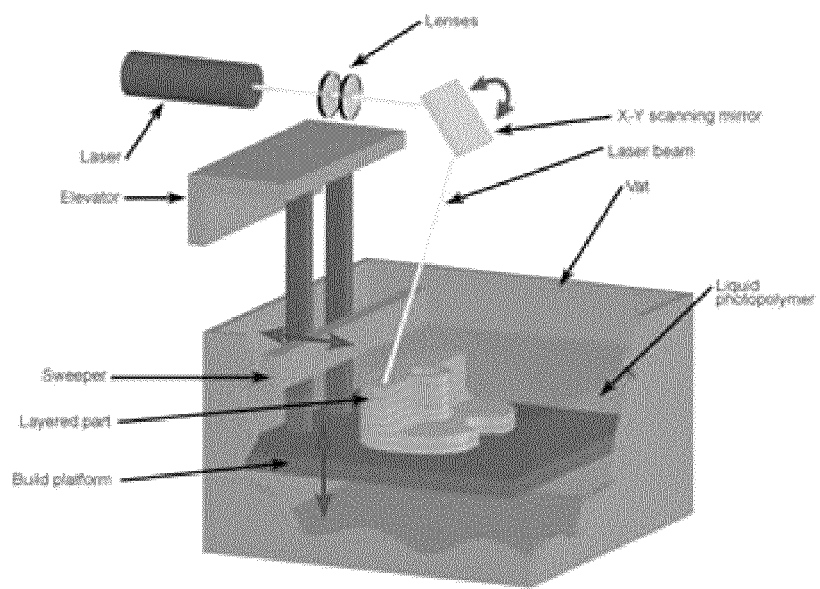
FIG. 6 provides an SLA illustration.

The stereolithography process uses a laser beam in the ultraviolet wavelength (on the order of 325 nm) to sequentially cure (polymerize) cross sectional slices in a liquid photopolymer resin vat to create the 3D contours of the build object. See FIG. 6 for a SLA illustration. The area of photopolymer that is hit by the laser beam partially cures into a continuous thin sheet which is parallel with the X-Y plane. The platform upon which this sheet sits is then lowered by one layer's thickness (3D Systems Viper resolution is on the order of 0.05 mm in the Z-axis) and the laser traces a new cross section on top of the first. Most lasers are static in the machine, with the beam continuously redirected by mirrors for profiling the path. The build sequence for a laser is typically first the borders to dam the liquid volume from flowing out, followed by a rectangular hatch to solidify the layer. The laser is powerful enough to penetrate through the top few adjacent sheets and binds them together to create the final three-dimensional object. Acrylate-based photopolymers are the most widely used resin systems developed for stereolithography. As part of the build calibration, each part is scaled to account for a shrinkage factor, usually on the order of 0.8% or less.

For any overhanging features in the part a support lattice framework is built with each layer to stabilize the part geometry and isolate the part surface from the build platform. Inclines of greater than 30 typically do not require a support structure.

After the build process has been completed, some post processing is required. The support lattice needs to be manually removed and the contact surfaces manually cleaned. Isopropanol is a common chemical to assist cleaning. After cleaning, the part must be transferred to a ultraviolet (UV) oven to finish curing the resin.

SLA parts are susceptible to shrinkage and distortion even after post-processing. Heat, moisture, and contact with chemical agents and strong solvents will affect the color, shape, and integrity of the material. Moisture and heat causes the part to soften and creep, while continuous exposure to UV light will increase the opacity of the resin. These wavelengths already cure the resin in the build chamber, and overexposure to UV light will embrittle the parts.

The table below presents advantages and disadvantages of SLA.

| Main Advantages: | Main Disadvantages: |
|---|---|
| Excellent Surface Finish | Degradation from Prolonged UV Exposure |
| High Strength Material Properties | Post-Processing Requires HAZMAT |
| Availability of Transparent Materials | Post-Curing UV Process Required |
| High Build Speed | Limited Biocompatability for Prolonged Contact |
| Low, Predictable Shrinkage factors for resins | |

Extrusion Based—Fused Deposition Modeling

Fused Deposition Modeling (FDM) creates layers by extruding beads of molten thermoplastic which bond as they contact the part surface and immediately cool. FDM can utilize many compositions of plastic—the most common being ABS, Polycarbonate, or a combination. New variations and combinations of extrusion head design are appearing quickly, but the most common is one nozzle for support material, one nozzle for build material. The build chamber is a heated space, maintained at a temperature just below the material's melting point.

Figure 7:
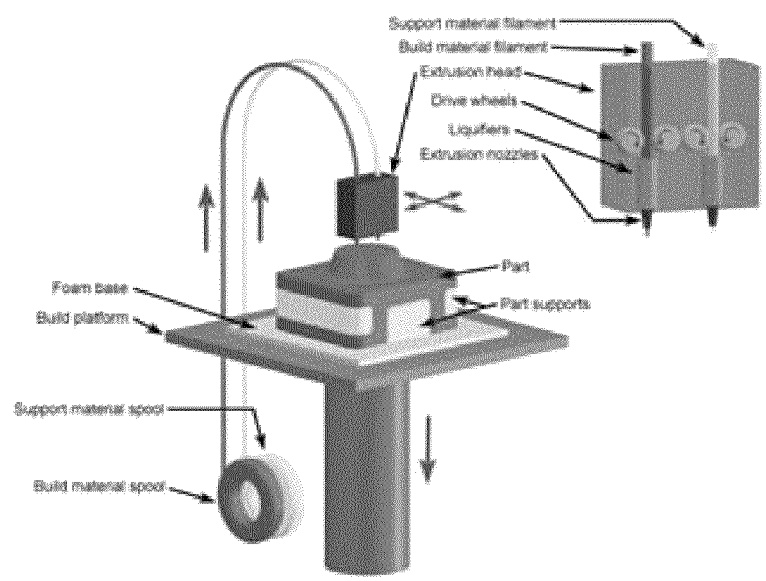
FIG. 7 illustrates an FDM setup.

Within this heated environment when one layer of liquid plastic contacts the semi-molten layer beneath it they will harden together as the two layers bind. Build and support material is feed in like spools, and after the extruder has completed the cross-section in the X-Y plane, the platform drops one layer thickness for the next profile. Thermoplastic modeling material feeds into temperature controlled FDM extrusion head, heated to a semi-liquid state. The resulting part will be anisotropic, with structural properties dependent on XYZ direction, and will have a relatively coarse surface finish. See FIG. 7 for an illustration of an FDM setup.

Post-processing for FDM requires removing the support material, which is either broken away manually or washed off using soap and water in an ultrasonic bath. The latter uses support materials which are water-soluble (WaterWorks-soluble support system). For internal structures, it is near impossible to remove the breakaway support configuration, but if only built externally, readily separate when the part surface is flexed.

The Z-height layer thickness ranges from 0.15 mm to 0.35 mm from a wire filament typically 1.15 mm in diameter. The high viscosity of the plastic limits the deposition rate, and resulting build speed since the entire cross section must be filled with material. The smallest features for an FDM cross-section are limited to twice the diameter of the extruded bead because it will always trace an outline of each edge for the cross-sections before filling in between. The table below presents advantages and disadvantages of FDM.

| Main Advantages: | Main Disadvantages: |
|---|---|
| Minimal Waste of build Material | Unpredictable Shrinkage |
| Ease & Simplicity of Post-Processing | Delamination Rate impacts material properties |
| Ease of Material Change in Build | |
| Inexpensive Material | |

Multi-Polymer Jetting

Figure 8:
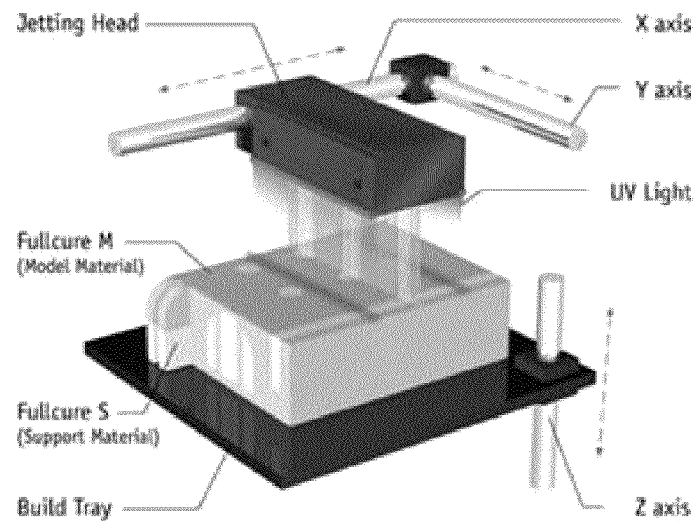
FIG. 8 illustrates a multi-polymer jetting process.

Multi-Polymer Jetting (MPJ) systems (e.g., from Objet) have the capability to manufacture parts out of multiple materials within the same part or platform. The technology is based on hardware from traditional jet printers, but deposits rows of material that each have thickness. The photosensitive ink is immediately cured by a UV lamp, and kept flat with a planar; which both trail the build stage. It is compatible with a wide range of materials with different properties, and can produce rubber-like parts with various Shore A values. FIG. 8 illustrates a multi-polymer jetting process. This fabrication process has capabilities to produce thin heterogeneous structures, with discrete features possessing different mechanical stiffness values.

Each region is saved as a separate STL file, and are aligned by using a common coordinate system. This allows multiple features to be connected while being built with different properties. The technology is commonly used to prototype overmolding, rubber features and coatings, and other applications using compliant surfaces. These show that heterogeneous parts of compliant Fullcure 970 TangoBlack and rigid Fullcure 830 VeroWhite materials to build membranes with thickness 0.58 mm. The table below presents advantages and disadvantages of MPJ.

| Main Advantages: | Main Disadvantages: |
|---|---|
| Very high feature resolution | Cannot Build Hollow Cavities with support material |
| Ease & Simplicity of Post-Processing | Sensitive to UV light |
| Ability to build heterogeneous parts | |
| High fabrication speed | |

Powder-Based: Selective Laser Sintering

Selective Laser Sintering (SLS) uses a $CO_2$ heat-generating laser beam to sinter thermoplastic nylon powder together in consecutive layers to form a complete object. Between building each cross-section, precision rollers deposit a thin layer of powder on the top of the build chamber. The build chamber is heated near to its sintering temperature and when the laser is directed to the profile it heats the particles just beyond their melting point and they fuse together. Sintering differs from melting or fusing because it joins powder particles without deformations caused by flow of molten material. The narrow beam causes only particles directly in the center of the beam to reach the sintering point and although adjacent layers get heated they do not melt and instead serve as continuous support.

The platform descends one layer thickness (range of 0.076 mm) and traces the next profile (X-Y plane resolution of 0.178 mm for feature edges). The build chamber is filled with inert Nitrogen gas to maintain a consistent heat and laser strength until the part is complete. Density and shape of gathered particles has significant effect on bonding and mechanical properties. Generally with higher density of packing come better mechanical properties. After cooling, the powder forms a matrix of approximate density of particle material. Grain boundaries affect mechanical properties like elastic limit and Young's Modulus. Finer-grain materials have higher yield strength and hardness than coarse-grain.

Figure 9:
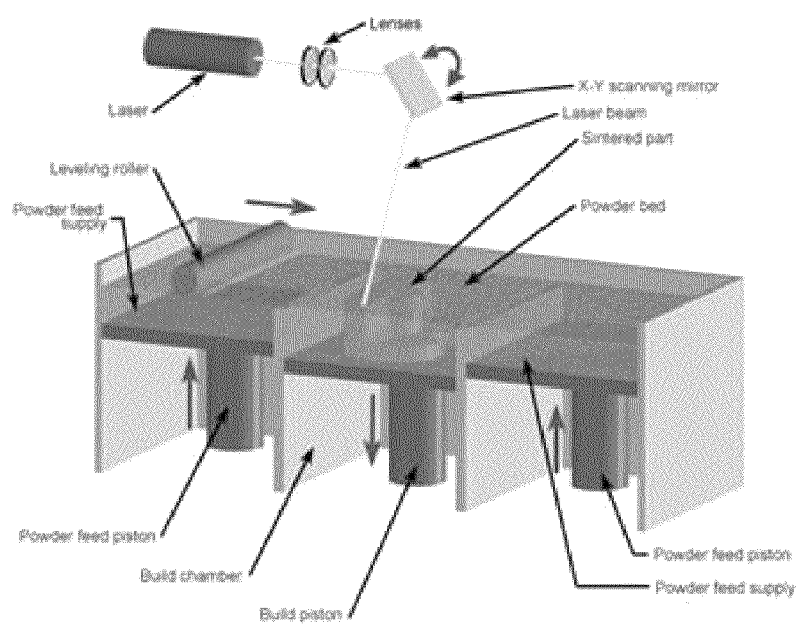
FIG. 9 illustrates an exemplary SLS system.

At high temperatures grain boundaries enhance creep rate in metals, coarse grain is preferred for lower temperatures. It is important to balance the grain size of the plastic. Large particles will cause the part surface to be coarse, but if ground too fine then electrostatic charges can build up and make it difficult to spread powder in 2D layer. This process has been utilized for thermoplastics, composites, ceramics, and various metals. For plastics it is commonly some derivative of polyamide (nylon, sometimes glass-filled), and for metals is commonly a combination of titanium and stainless steel. FIG. 9 illustrates an exemplary SLS system.

For as many hours as it takes to build a part, it is required to cool down the chamber before the part(s) can be freed from the powder and cleaned. The particles neighboring the part walls stick slightly to the finished part from thermal conductivity. As part of the post-processing, these particles will need to be blown away with compressed air and sometimes sanded.

Materials have a common quantified shrinkage of 3-4%. Combined with residual stresses from thermal bonding and cooling it increases the tendency for thin parts to curl, bow, or warp if they are improperly stored before cooling completely. The un-sintered powder from a build cannot all be reused for new parts since it has deformed. After remaining in a prolonged state of elevated temperature it will not bind as predictably as before. This necessitates using at least 40% virgin (i.e., not previously heated) material for every build platform. The remaining powder from previous build cycles is considered scrap and disposed of or recycled. The table below presents advantages and disadvantages of SLS.

| Main Advantages: | Main Disadvantages: |
| --- | --- |
| No Support Structure Required | Almost 50% Virgin Material per Platform |
| Materials Available for High Flexibility | High Startup Power Consumption |
| Biocompatible Materials Available for Short Term Implantation, and sterilization | Cost-Effective Build Requires Filling an Entire Chamber |
| Actual Nylon as time-stable material | Large Infrastructure required |

Embedded Electronics

For more extensive monitoring and greater traceability of a wearer's medical state, electronic sensing and data transmission components may be embedded into devices either worn or in close proximity to the body. This allows for iterating design and geometry changes as necessary based on one or a combination of patient feedback, biomechanical analysis of the device and its wearer, and measurements taken by embedded sensing elements.

Various models have been discussed for process planning of embedding electronics occurring anywhere between the design to post-fabrication stages of device creation. Customizable sensors which can interact with a human at a meso scale without being overly complex pose unique design and implementation challenges. Two in particular are integration with the surface geometry and device body, as well as the range of compliant and rigid mechanical properties of the soft tissue. A number of different types of electronics and sensors have been embedded into devices for the purpose of sensing physical phenomenon, or transmitting its data.

Piezo-Resistive Sensors

Piezoresistivity is a material property where the electrical resistance changes from an applied strain. The internal arrangement of the atoms' energy bands dictates the degree of this effect. Metals and semiconductors both have piezoresistive properties, and even insulating materials are able to be endowed with this characteristic by doping them with conductive particles. The size, shape, concentration, and doping material itself all affect the degree of this effect. Flexible insulating materials like rubber or foam can be made conductive by using the doping. The piezoresistive phenomenon differs from the piezoelectric effect in that strain induces a change in electrical resistance only, whereas the latter produces an electric potential.

From theory of mechanics, the direction of the applied strain is important since the longitudinal and transverse strains will differ slightly according to the Poisson's ratio. Likewise, the respective piezo-coefficients will slightly differ, even if the material is isotropic because the cross section shrinks. In a semiconductor the dominant value is associated with the dominant stress. The unit resistivity (also referred to as volume resistivity to note that current passes through the material, not along its surface).

Strain Gages

Figure 10:
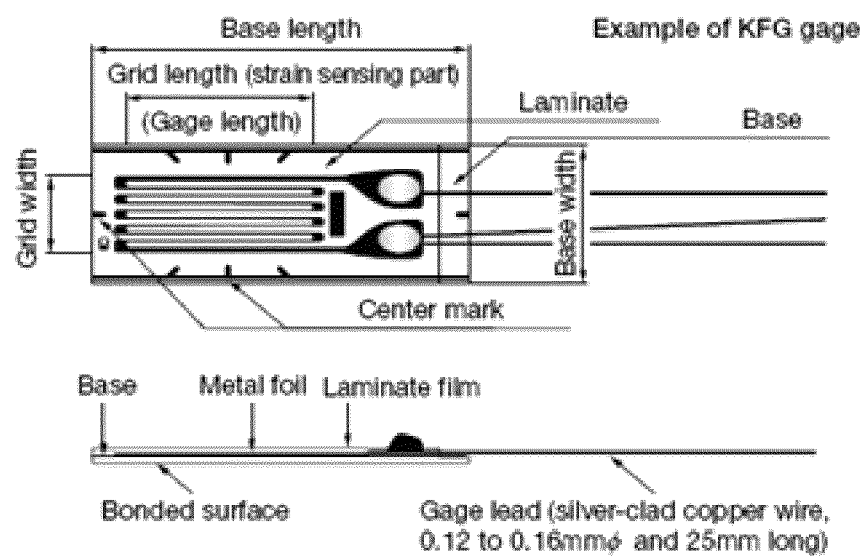
FIG. 10 illustrates an exemplary strain guage.

A strain gage is a thin metal foil of a single lead, arranged in a rectangular zig zag pattern to measure small deflections at the application surface. The metal foil is a piezoresistive material on a plastic backing designed for uniaxial strain sensing. FIG. 10 illustrates an exemplary strain guage. They can be arranged in a circular array to form a rosette, each one using a Wheatstone bridge to convert the resistance to a voltage and measure it according to a known reference. They can be delicate to apply and susceptible to thermal drift.

FIGS. 11A and 11B present different research and commercially available sensor techniques that use the piezoresistive effect for human biomechanics sensing.

Sensors Based on Infrared and Optics

Infrared (IR) sensors use a photo diode to determine the wavelength and intensity of light as outputted by an analogue signal. These devices can record the environmental conditions using just this component, or when in a controlled chamber use a light emitter as the known value and be calibrated when the pathway is interrupted or partially occluded. FIGS. 12A and 12B present different research and commercially available sensor techniques that use IR/optical for human biomechanics sensing.

Sensors Based on Magnetics

Using the hall-effect to measure proximity of permanent magnets is a popular choice for robust two-state sensors. In many automobile models for example, the ignition key turns on the engine using a magnet and hall-effect switch.

Using a rectangular array of four hall-effect sensors around a permanent magnet, a modular sensor has been embedded in polyurethane. Multiple arrays of this design have been applied to the end effector of a robot (e.g., the 'Obrero' robot) as a sensing skin. The compliant design was chosen to mimic the performance of human skin, and to overcome some of the challenges the researchers had previously found using FSR technology.

Sensors Based on Capacitance

Design of a capacitive-based force sensor array have been developed by researchers at the National Taiwan University in Taipei that can sense both normal forces and shear forces by detecting the displacement of a flexible polydimethlysiloxane (PDMS) membrane. Approaching the design from a MEMS standpoint, Cheng et al. use PDMS as the flexure, and an array of four capacitors as the strain transducers. The components of normal and shear forces are determined by the magnitude and distribution amongst the four sensing elements under the dome. Similarly to the magnet & Hall effect design in the previous section, this uses an inexpensive rectangular array of OEM sensors to create a 3-axis sensing dome. The foot print of each sensor is 8 mm×8 mm.

Sensors Based on Conductive Materials

Conductive materials can act like wires, radio antennae, or contact switches. The composition of these traces can be from simple graphite suspensions to more rare materials like platinum which are highly conductive. The methods of deposition on the exterior of surfaces range from extrusion to aerosol jetting, similar to airbrushing. These technologies for creating for conformal electronics are sometimes referred to as 'direct print' or 'direct write'. FIGS. 13A and 13B present different research and commercially available sensor techniques that use conductive materials for human biomechanics sensing.

Force Sensing Resistors

The technology for Force Sensing Resistors (FSR) uses degree of contact between two thin surfaces to measure how much force is being applied. Although at first this may seem like a piezoresistive effect, and operationally they are very similar to strain gages, but the composition of the films are contact based because they are intended to have a constant unit resistance. Although termed to detect force, an equally apt name would be 'pressure sensitive resistor' since the measurement depends on a load applied across the circular detection area. Depending on the composition, they can measure forces up to 120 lbf, acting like a variable resistor having a range for example from 0 to 1.2 kΩ.

The sensor is constructed of three regions: (a) the base active area with two electrodes leading out; (b) a spacer ring on top along the perimeter; and (c) an application disc with conductive ink screen printed on the underside. As the applied force within the sensing area is increased, the amount of conductive ink connecting the two electrodes on the base area increases, and the resistance of the sensor drops. The thickness of the spacer is typically between 0.03 mm and 0.1 mm and may be screen printed of a pressure sensitive adhesive, may be cut from a film pressure sensitive adhesive, or may be built up using any combination of materials that can both separate and adhere to the two substrates. Some variations have a third conductive layer or high-temperature materials, but hold to the same general operating principle. Some major advantages of industrial FSRs are their low cost, thin profile, and flexible substrate. Some disadvantages are the conditioning requirements, sensitivity to surface area of load application, drift, and hysteresis compared to high-accuracy strain-gage based load cells.

Shape Deposition Manufacturing

Figure 14A:
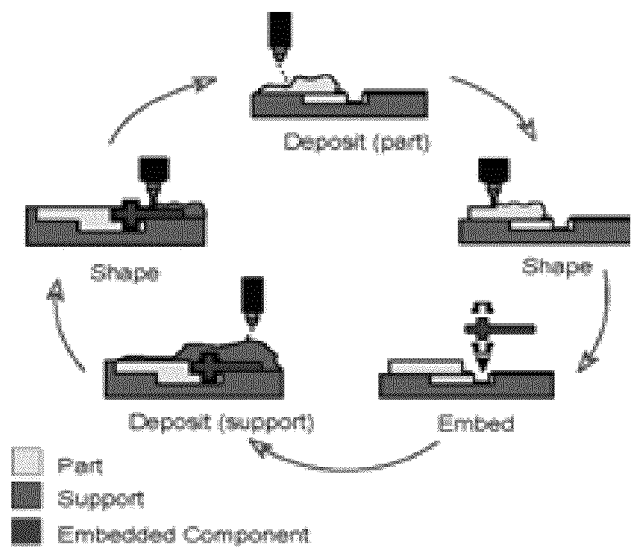
FIG. 14A illustrates fitting of components between stages.

Shape Deposition is a manufacturing paradigm which incorporates the advantages of several processes including Additive Manufacturing, 5-axis CNC machining, shot-peening surfaces for stress relief and 'microcasting'. Between the stations for these processes, a robotized palette can move a part job, and allow fitting of other components like circuit boards and mechanisms in between the stages as shown in FIG. 14A.

Figure 14B:
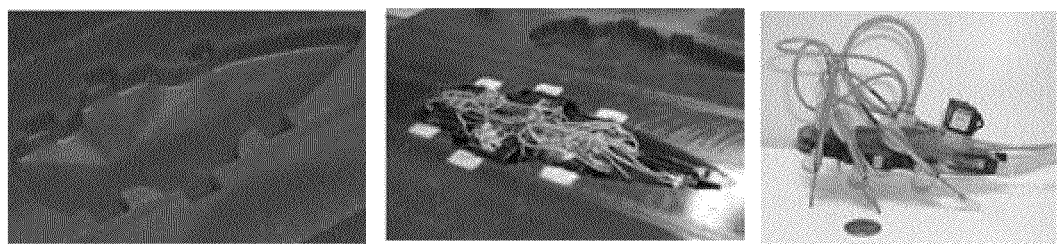
FIG. 14B illustrates SDM stages of Robotic Insect Body with embedded components.

SDM techniques have allowed parts to be built with electronic components already assembled inside the body of the part for sensing and actuation. Researchers in SDM advocate that in fabrication of small scale robotics, the fasteners can dominate much of the complexity, volume, and mass. One of the aims of this process is to remove these constraints. This also allows for more biologically inspired design, as in the case of integrating electrical and mechanical components for the robotic hexapod shown in FIG. 14B. This figure illustrates SDM stages of Robotic Insect Body with embedded components [ref Clark 2001 from Stanford].

As shown above, the geometry cavity was milled from wax, the components were inserted, and casting material was poured to fill the voids, with one final milling operation to clean the exterior surfaces. Having access to the interior of the part during the build enables placing passively compliant components by embedding material sections of varying stiffness. In design of a compliant under actuated hand, flexible materials were inserted during the fabrication process to remove the need for fasteners The entire SDM process uses several high-resolution machines which incurs combined time and cost overhead. One version of the shaping station used was a 5-axis CNC milling machine with a 21-head automatic tool changing mechanism. SDM is a highly flexible set of processes, and avoids many of the challenges associated with using conventional AM materials. However it is currently still a specialized research process not readily available to commercial sources like on-line vendors.

Small Scale Mechatronics

The ability to embed specialized components and geometries in small-scale mechatronic devices is possible through techniques other than SDM. FIG. 15 presents different research and commercially available sensor techniques that use small scale mechatronics for human biomechanics sensing.

The described embodiments provide a methodology that integrates sensor design with device architecture for equipment which interacts with the human body. The objective of embedding sensors into custom devices may be achieved, for example, by using an Additive Manufacturing (AM) approach. Although a variety of fabrication methods may also be used for the described embodiments, the group of AM technologies are shown in the examples herein because they provide the most flexibility and agility of resources for a small customized group of devices. Additionally, AM has a unique fabrication ability to create parts with voids and cavities inside whose geometry has high resolution, accuracy, and repeatability.

The interior sensing element is relatively similar for each type of sensor (e.g., force, torque, impact) but the surround flexure changes depending on what phenomenon is desired to detect. The mechanical stiffness of this flexure is dictated by the surrounding geometry, which is customizable according to the magnitude of force, moment, etc. This being said, the sensor can be designed to suit low frequency & large magnitude strains of for example lower extremity orthotics, high frequency, lower magnitude strains for upper extremity devices, or something in between.

By specially designing the geometry of voids and cavities of a device, and injecting into them a conductive elastic gel, a low-cost design option for interaction sensing as well as device self-diagnostics is possible. Depending on the design of the surrounding structure many different types of mechanical sensor are possible, and standalone sensor examples are developed in this chapter for force, torque, and impact.

The possible applications of an embedded sensor have a wide range of requirements which may even sometimes conflict. For the exemplary modalities in this chapter, the sensor requirements will be selected as if the described embodiments are used for upper extremity biomechanics measurement. For human-interaction studies, force sensing resistors (FSR) would normally be the first low-cost choice. The described embodiments lower the barrier to adding instrumentation by approximating the performance of comparable FSR technology but allowing greater design flexibility, ease, and cost.

The fabrication options with the AM fields were compared according to range of physical build capabilities, as well as the material selections and unique attributes. Transparent interaction with the wearer was the most important requirement for the interface. The presence of the sensors should not alter the user/wearer's actions from discomfort, and should not pose a danger or hazard to them. Lastly, for commercial force-sensing resistors the lead time for custom shape and loading range can take between 2-4 weeks, or longer in case of high demand. In some embodiments described herein, the entire CAD, fabrication, and preparation for a sensor device may take less than one week. A set of sensor requirements associated with the described embodiments is compiled in four categories in the table below to compare to commercial alternatives.

measured either with a Hall Effect sensor, or as a variable resister. The process of producing permanent magnets requires specialized equipment to polarize the ferrous particles and needs to be in a specific orientation and alignment. This may not be as practical as other sensor phenomena for unique custom parts with non-regularly placed sensors in varying orientations.

Conductive liquid suspensions which remain in a liquid state tend to settle if not rotated periodically. The liquid channels themselves may also be susceptible to leaks and require a flexible reservoir adjacent to the sensing site. Being able to fit the sensing material into the cavities necessitated it to be in an injectable/extrudable gel or fluidic state during the build and then later solidify to retain a robust shape.

| Sensor Goals to Match FSR Technology for Upper Extremities | | |
|---|---|---|
| Aspect | Requirements | Specifications |
| Force Sensing Performance | Accuracy | Linearity = 4% |
| | Longevity | Drift <5% log time scale |
| | Low-Medium Force Range | Force range up for 20 N |
| | Hysteresis | Hysteresis 5% Full Scale |
| | Output resistance measurable | Low cost additional amplification hardware |
| | Single axis sensing | Examine effect of shear forces |
| | Number of cycles functionality | Examine up to 5000 cycles |
| Fabrication | Does not require AM hardware modifications for SLA, FDM, SLS, MPJ machines | Existing AM machines are candidates for fabrication |
| | | Minimum Build Feature Resolution 0.5 mm Hollow cavity & void capabilities |
| | Materials have time-stable Properties | Flexure does not mechanically or chemically degrade over time |
| | Low-cost | Batch device quantity is under $10 per sensor |
| Human Interaction | Comfortable against the body | No sharp protruding features, smooth integration with surrounding structure |
| | Functional for range of body compliances | Can be used against boney protuberances and musculature tissue rigidities |
| | Non-intrusive | Can be built as near imperceptible to the user |
| | Poses no serious biohazards pre or post-cure | In superficial contact or vessel rupture non toxic |
| Customization | Short Lead | Time for full custom is under 1 week |
| | Minimize operations to customize & embed sensor into design | Design and embedding process has foresight for automation |
| | Embedding process has high agility | Embedding process does not change for each device |
| | Each sensor individual customization | Geometry is sensor-specific and location-independent |
| | | Inputs taken from user, designer, and their data |

While the exemplary embodiment utilize piezoresistance, other sensing phenomenon such as magnetoresistance, capacitance, and inductance may also be used, although with varying degrees of effectiveness.

For example, capacitive-based sensors such as dielectric polymers can be highly accurate and cover large surface areas. They use the contact between two thin films to measure the buildup and passing of electrons to relate back to contact and sometimes pressure. The specialized geometry to provide the deflection ranges between the films can be several orders of magnitude lower than most AM processes. However, the practical challenges of inserting or attaching two thin film materials over a variety of non-planar geometry may be more complex than using an existing off the shelf solution to assemble into a cavity of the device.

The magnetoresistive and ferromagnetic phenomenon are viable as options as suspensions of ferrous particles which can be injected and then magnetized in hollow cavities of the device. Either method may induce an electrical change in the presence of the field of a permanent magnet and could be Accordingly, some of the described embodiments may utilize a material from the family of piezoresistive elastomeric suspensions would offer an effective sensing element to fulfill the specifications.

Sensors according to the described embodiments work as a transducer that converts mechanical deformations to detectable changes in electrical signals. The core of the sensor element takes advantage of a piezo-resistive polymer within an AM structure that is integrated seamlessly with the surrounding device body. The mechanical properties of the AM material and the physical properties of the geometry surrounding the sensing polymer dictate the mode and amount of strain it will undergo. Specific geometry can limit deflection to a single plane, while the material stiffness and elastic range dictates the physical deflection. This can be controlled by selecting dimensional properties in synchrony with the build material so that the flexure's maximum elastic deformation is always selected for the anticipated loading range.

Commercial force sensors have a sensing element which is strained by the deformation of a well-characterized reasonably rigid exterior housing. Such commercial versions however cannot be embedded within the body of small devices and are complexity and cost-prohibitive for many human-sensing applications. In addition, to act as a self-diagnostic of the mechanical fatigue and performance of the medical device, these commercial structures could not be distributed throughout the volume of the device.

Figure 16:
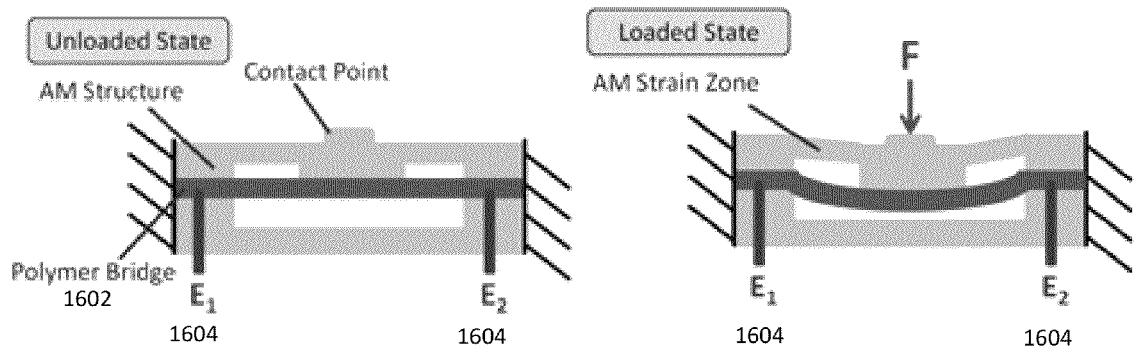
FIG. 16 illustrates devices that use a spring flexure element built from AM materials.

Instead of aluminum or stainless steel as the spring element to strain the sensing component, some of the described embodiments use a spring flexure element built from AM materials as shown in FIG. 16. The piezoresistive polymer is contained in the polymer bridge 1602 and acts as the variable resistor element in the sensing circuit. An electrode 1604 at either end of the polymer bridge 1602 is the connection to attach the sensor to a circuit. Except for the volume of the sensing element, the geometry and dimensions of the polymer bridge remains independent from the device geometry surrounding the embedding site. The device design can be adapted from a legacy part or taken from a 3D scan containing freeform geometry like that of the human body.

The range of geometry for the polymer bridge and sensor may be concurrently based on structural characteristics, as well as electrical and fabrication capabilities. The dimensional design may be iterative as more constraints and benefits are determined from the polymer to be embedded, the polymer electrical properties, and sensor design robustness. The bridge 1602 may have a constant cross-section (i.e., constant along the length of the bridge) for homogeneous flow of electrons and to avoid geometries which create sudden pressure step when the polymer is injected, although other cross sections may be used. One embodiment of the bridge may have a circular cross section (although other shaped cross sections may be used) because the corresponding radial symmetry avoids shear friction concentration areas when the polymer is injected, and because the bridge itself will have the highest stiffness in each axis. The circular profile also simplifies the CAD process because it maintains a constant depth profile, which makes the bridge and injection line immune to rotational alignment challenges that can result from creating 3D swept cut features in the device volume. This is also why the polymer bridge may have a constant wall thickness around its central axis to contain the conductive material.

Repeatability and reliability of the signals is tied to the linearity of the flexure deflection. Thus, the described embodiments may constrain deformation to remain within the elastic zone of the stress-strain profile of both the conductive sensing material and its AM flexure housing. This is assuming the selected sensor function is to measure force/strain from ongoing use. For a safety warning in case of a device over-strain, it is only necessary to measure once a strain which exceeds the proportional limit and alert the user.

Figure 17A:
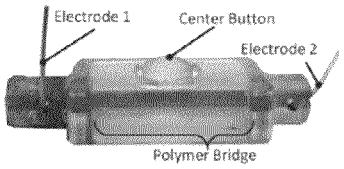
FIG. 17A illustrates the general working principal for piezoresistive elastomer suspensions.

The mechanics of the polymer bridge dictate the range of forces the flexure of the sensor can elastically experience. The instantaneous longitudinal strain of the polymer dictates its electrical state and is key to simulating its electrical response. Its significance is the degree to which the conductive particles are separated. FIG. 17A illustrates the general working principal for piezoresistive elastomer suspensions.

Mechanical deformation considerations exist for exploiting the piezoresistive longitudinal strain properties. In the case of a simple and well-characterized geometry such as a cantilevered beam with a point or distributed load, the neutral axis passes through the centroid of the beam which creates a zone for tension and a zone for compression. A beam in pure bending has no axial stress on it so wouldn't have any strain at the particles on the neutral axis. Piezoresistive materials operate on a premise of uniform tension through their cross-section to pull the conductive particles away from each other. Having a compression zone adjacent to the tension zone could have unpredictable electrical responses.

One option to retain a cantilever design is to introduce the hollow polymer bridge area to the tension side of the beam and keep it as a cantilever. However this design can be quite fragile for anything but very small loads and is sensitive to off-planar loads. Clamping the bridge on either end as a 'built-in beam' design ensures longitudinal strain along the centroid of the bridge, keeps the radial symmetry, and overall stiffens the sensor geometry. Assumptions for this model include:

Silicone is not structural, i.e. it will not have any mechanical support.

Silicone will not have any longitudinal slip relative to the ABS hollow bridge, i.e., the strain of the flexure is the strain of the sensing element.

There is planar XY stress only.

Since both ends of the bridge are clamped, each side has two reaction forces and a moment, making the problem statically indeterminate since we have six unknowns and only three equilibrium equations. However we can remove some by using symmetry conditions since the load is applied directly in the center of the beam. The deflection equation for the built-in beam is a $4^{th}$-order equation with a $2^{nd}$ order spatial derivative along the beam axis. Maximum deflection occurs at the beam center, along the line of symmetry. This value dictates the magnitude of longitudinal strain. When designing the polymer bridge of each sensor for its application device, the force will be the primary specification in the analysis, followed by the three geometric parameters: tube inner diameter, tube outer diameter, and bridge length.

It can be shown that in the case of a beam in simple bending, the longitudinal strain along any plane parallel to the deformed neutral axis is constant. This is not valid for the conditions here because the deflection profile is a curve with non-constant radius, due to the clamped conditions at either beam end. The strain will vary along the bridge with minimum values at the boundary edges & center point since the slope is zero, and maximum values at $x=L/4$, and $x=3L/4$ from maximum slope and the symmetry conditions. Therefore it is helpful to examine the strain plot of the entire beam and check the average strain which the polymer is subjected to.

Exterior: AM Housing Special Considerations

The particular geometry of the described embodiments, as well as the scalable design requires very specific fabrication capabilities which can also easily produce a wide range of sensors; both stand-alone and embedded in the body of a device itself. This makes using Additive Manufacturing (AM—also commonly referred to as 'Rapid Prototyping' or 'layered manufacturing') attractive, which can be used to build highly accurate features at a small scale, including hollow features and voids, thin surfaces, and is expandable for a mass customization platform with a variety of materials. For medical sensing applications, although it is important to select parts based primarily on material properties, it is not mutually exclusive from its AM fabrication process. They are examined concurrently since the process settings will significantly change the material properties expressed in a part.

Enabling Solvent Escape

The AM material structure around the polymer bridge needs to offer appropriate conditions to completely cure the conductive material. In the case of solvent based epoxies and silicones, there needs to be some way of allowing the solvent gas to escape the silicone during the degassing phase. The solvent can depart from the polymer via pores and micro cavities in the AM material, or by chemically combining with it. Examples of these two methods were evaluated using samples of SLS nylon 12 and SLA Accura 40 plastics, which were imaged with a scanning electron microscope for micro pore structure to evaluate solvent escape.

The nylon used in the SLS process is chemically non-reactive to the solvents but contains a pore structure that allows the gas to escape. Completeness of curing is confirmed by the resting resistance value of a polymer bridge.

During the sintering process, the core regions of a part will have been kept at an elevated temperature for longer since there is a higher laser dwell time, as oppose to the edges where it dwells for the shortest time and the particles between layers don't fuse together as completely. As the depth of the layer increases, each layer becomes more solid and porosity reduces, which is more challenging for the gas to escape into. Therefore for best possible cure conditions the sensor site and insertion channels should be closer to the surface/outer edges of the part features.

The SLA parts are non-porous and have the most well-ordered crystal structure, but to a certain degree still allows curing by chemically accepting/combining with the solvent up to a saturation point. This material exhibits the conditions most challenging for the solvent to escape because the threshold is material-dependent, and it may structurally degrade the bridge interior. The SLA parts have no pore structure or room for the solvent to escape into. It has been confirmed that the polymer reaches full cure under certain geometric conditions, and a portion of the channel interior was dissolved. The SLA resin is chemically sensitive to strong solvents like isopropanol or ethers even in its fully cured state, which reinforces the assumption that the solvent gas is reacting with the polymer bridge interior. Although the degraded tube still conducts electricity, the degradation creates a dead zone and reduces sensitivity of any strain-based sensor design because the silicone is no longer strained equally to the SLA flexure around it. Cross sections of the ABS FDM and SLS Nylon 12 tubes did not exhibit any similar reactions.

Orthotropic Mechanical Properties

Mechanical properties of AM fabrication materials are orthotropic by nature and are dictated by their build orientation. At least some of the embodiments measure the strain state of the surrounding material in the elastic zone and notify the user of the forces without crossing the yield point into permanent deformation. Depending on the sensor insertion location, the orthotropic material properties will affect the strain limit. SLS nylon is an ideal AM method for building devices using this solvent-based elastomer sensor because the porosity can be well-controlled by the sintering parameters, in addition to having a high elastic limit and being biocompatible.

Results were averaged for five samples built in three orthogonal Z-axes. It is also worth noting the difference in failure mode depending on orientation. Sample A acted more like a brittle SLA material since it did not have a well-defined yield point with any plastic deformation. A plastic deformation zone is also an important safety consideration to minimize hazards to the wearer in the event that a failure mode occurred.

The part will always carry the highest mechanical properties when the Z-build axis is normal to the cross-sectional build planes of greatest surface area. Sample B had the greatest 'necking' and largest elastic deformation zone. Sample C was more prone to failure at stress concentration zones, and sample A was the most brittle. If orientation of sensor vs build/part orientation is an influence on performance then the robustness of measurement will need to be verified and accounted for in signal acquisition or filtering.

Interior: Conductive Material

Sensors of the described embodiment include a conductive elastomer with piezoresistive properties. A suitable material exhibits a change in electrical properties when subjected to strain from the AM structure surrounding it, while complying with the insertion limitations from operating within hollow cavities and be safe to use alongside humans. Polymer requirements may be subdivided into four categories based on physical properties, and ease of integration into the AM polymer bridge design.

Integration with Current Vendor Processes:

To facilitate commercial accessibility the end AM components should be buildable in nearly any service bureau, and either the end user can insert the conductive elements themselves or the bureaus can easily add it to their service capabilities without modifying their current AM hardware to embed the conductive material. This also necessitates the conductive material itself to be readily available and not require any special handling procedures outside of good laboratory practices. Shape Deposition Modeling (SDM) is a technology specially suited to insert components and materials during the build phase, but requires specialized hardware and the technology are currently not widely accessible to researchers or consumers via service bureaus.

Insertion [Embedding] & Preparation of Conductive Material:

The sensor operation site may not be adjacent to the insertion site, so the material had to be able to pass into the sensor site without deteriorating. If the conductive material was inserted in an uncured state, it had to cure within the partially enclosed chamber for the sensor, in conditions of ambient temperature and pressure. Many AM materials have creep temperatures below 200° C., which is a common curing temperature for compression molding to vulcanize elastomers. Most piezoelectric and ferroelectric materials require deposition and crystallization conditions for temperature ranges of 200-800° C. The AM structures may also have delicate features and it would be challenging to pressurizing the chamber containing the conductive material. This excluded many silicone rubber suspensions since they require high pressure and temperature to cure, and AM thermoplastics as well as many SLA resins have creep temperatures far below the rubber curing temperature. For manual insertion there is a practical expectation to have a few minutes between removing the conductive material from its container and inserting it into the cavity of the AM structure. The insertion requirement is specified as a pot life of at least 5 minutes.

Electrical Properties:

The target electrical properties are a combination of performing functionally like a strain gage, with some common characteristics of potentiometers and FSR.

In a sensing resistor, current is being spent as thermal energy through the resisting element. A high electrical impedance (many FSR elements are in the MΩ range) would reduce the amount of current moving through the sensor at the resting state. This also minimizes the susceptibility to thermal effects and maximizes battery life when self-powered. FSRs are usually accompanied by a relatively high change in resistance during loaded (0-50% operational range). Comparatively, typical strain gage resistances range on the order of 0.01–1 kΩ. Although sub ohm changes in electrical resistance can be measured and amplified it was preferable to see changes in at least the Ω range when the material is strained the maximum anticipated distance of 2-3 mm.

Ohm's Law between two measured points in a conductor $$V = IR$$

where:
V=potential difference between measured points
I=electrical current, A
R=resistance between measured points, Ω

Time-varying effects like capacitance should be avoided. For a charge buildup or dissipation it can affect design of analogue & digital filters, and would become a limiting factor for the maximum measurable frequency.

Mechanical Properties:

The mechanical properties of the internal sensing material should ideally not limit the mechanical structure but act 'invisibly'. To minimize complexity of modeling, the effect on mechanical stiffness should be negligible, while sensing the entire elastic range if continuing operation is required, or some of the plastic region if one-time failure warning is required. Linked with the mechanical requirements via the Gage Factor, the material should be able to electrically sense throughout its own elastic range to maximize the level of operational strain.

The requirements from the preceding categories are summarized in the table below.

| Polymer Requirements | | |
|---|---|---|
| Category | Inclusion Goals | Exclusion Criteria |
| Integration with Vendor Capabilities | Commercially available in variety of volumes | High toxicity pre or post-cure |
| | Does not require AM hardware modifications | Cost prohibitive for $10 per sensor |
| | | Shelf life is under 6 months |
| Insertion and Preparation | Can be inserted into hollow cavities post-build | High insertion pressure requires complex hardware |
| | Vulcanizes under room temp, pressure, humidity | Low viscosity prevents even curing |
| | Able to cure within hollow cavity of polymer channel | Destabilizes surrounding AM material |
| Electrical Properties | Consistent volumetric resistivity | Time-dependent properties |
| | Stable for Time, temperature, and humidity | |
| | Linear gage factor | Inconsistent gage factor |
| | Sensing range is equal to mechanical elastic range | Electrical range is binary state |
| Mechanical Properties | Elastic limit greater than AM plastics | Material is brittle |
| | Material is more compliant than AM plastics | |
| | Stable for Time, temperature, and humidity | Significant shrinkage after cure |
| | Particles remain in suspended positions, don't settle | High Poisson's ratio causes separation from polymer bridge interior |

While a variety of commercially-available conductive materials may be used in the described embodiments, the materials summarized in the table below provide an example of suitable materials. Many are conductive adhesives which are commonly used for electrically grounding enclosures or repairing broken electrical connections.

| Material | Operating Principle | Properties | Application Method | Resistance | Sample # | Hazards | Curing Conditions |
|---|---|---|---|---|---|---|---|
| Silver Paint, 18% Silver | Silver particles in evaporating suspension | Fast drying, conductive | Well Shaken in syringe | NA | 1 | Inhalation when uncured, flaking when cured | Needs complete air contact for curing |
| Silver Paint, 50% Silver | | | Well Shaken in syringe | NA | 2 | | |
| Scotch-Weld DP-100 Clear Adhesive | | 3 min work life | 2 part applicator plunger | NA | 3 | Eye, skin, respiratory irritant | Room Temperature and Pressure |
| Scotch-Weld DP-100 PLUS Clear Adhesive | | 4 min work life | 2 part applicator plunger | NA | 4 | | Room Temperature and Pressure |
| Conductive Flexible Circuit Pen | Silver-suspension for conductivity | | Pre-packed applicator pen | 31 Ω/cm | 5 | Ground Shipping only b/c of toxic Hazard | Needs complete air contact for curing |
| ResinLab Silver Conductive Epoxy | Silver particles densely packed | 40% strain, 1 hr pot life, $26 | Syringe | NA | 6 | Severe inhalation hazard | Room Temperature and Pressure |

-continued

| Material | Operating Principle | Properties | Application Method | Resistance | Sample # | Hazards | Curing Conditions |
|---|---|---|---|---|---|---|---|
| Conductive Thread | Copper and tin woven into thread, strain increases resistance | resistance changes for thread tension | Thread through cavity | 2.7 Ω/cm | 7 | None | None |
| Pure Silver Conductive Epoxy | High Conductivity | $28/50 g | Syringe | NA | 8 | None | Room Temperature and Pressure |
| Silver Conductive Grease | High Conductivity | Single Part | Syringe | NA | 9 | Eye irritant | Room Temperature and Pressure |
| Silver Conductive Grease | High Conductivity | Single Part | Syringe | NA | 11 | Eye irritant | Room Temperature and Pressure |
| 2 Part Conductive Epoxy | Conductivity | Already in Syringe, high conductivity | Syringe | NA | 10 | None | Room Temperature and Pressure |
| SPI Conductive Silver Paste | Conductive Silver particle suspension | High conductivity, absence of wicking | Cured film is a composite consisting of flakes of silver colloid in a polymer matrix | NA | NA | Severe Inhalation hazard from $CO_2$ & alcohol. Explosive | Room Temperature and Pressure |
| Elastosil LR 3162 A/B | Piezoresistive | Electrically conductive, Shore 51A, 400% elongation, | Industrial Press | 11 Ω/cm | NA | NA | 10 min at 165 C. in press |

The sections below describe a process for one or more of a large group of candidates for a conductive material according to the described embodiments. It should be understood, however, that such narrowing is not meant to exclude a candidate for use with the described embodiment, but rather to select a particular one from a larger group of suitable materials.

Each candidate was injected into a simplified bubble test specimen to simulate the instrumentation process and the candidates were narrowed according to the criteria described above. Each bubble test had 10 samples of the material and was checked for conductivity after the specified curing time. The dimensions of the bubble test for length and interior diameter were chosen from the easiest (largest) geometry goals of the final sensor.

The bubble test was an opportunity to compare the ease of preparing a rudimentary polymer bridge of the described embodiments. Most of the material samples could be injected via syringe, the translucent Accura 40 resin allowed observation of voids or cracks appearing in the cured states. Copper electrodes 0.016" in diameter were first inserted into either end of the bubble test chamber to compare ease of filling, curing process, contact to the electrode, and conductivity. From evaluation using the requirements set forth above, all of the candidates were unsuitable as detailed in the table below.

| Material | Outcome | Sample # | Suitability |
|---|---|---|---|
| Silver Paint, 18% Silver | Volume significantly shrinks and cracks, non conductive | 1 | Eliminated |
| Silver Paint, 50% Silver | Volume significantly shrinks and cracks, non conductive | 2 | Eliminated |
| Scotch-Weld DP-100 Clear Adhesive | Brittle, non conductive | 3 | Eliminated |
| Scotch-Weld DP-100 PLUS Clear Adhesive | Brittle, non conductive | 4 | Eliminated |
| Conductive Flexible Circuit Pen | High toxicity, voids appeared | 5 | Eliminated |
| ResinLab Silver Conductive Epoxy | Too Hard | 6 | Eliminated |
| Conductive Thread | Infeasible implementation | 7 | Eliminated |
| Pure Silver Conductive Epoxy | Inconsistent Conductivity | 8 | Eliminated |
| Silver Conductive Grease | Does not solidify | 9 | Eliminated |
| Silver Conductive Grease | Does not solidify | 11 | Eliminated |
| 2 Part Conductive Epoxy | Hard and brittle | 10 | Eliminated |
| SPI Conductive Silver Paste | $130 for 30 g: Cost prohibitive | NA | Unavailable |
| Elastosil LR 3162 A/B | Special order size minimum is 20 L barrel. Cost Prohibitive | NA | Unavailable |

With the commercial options unsuitable, a sample of prepared manually by doping a solvent-based silicone RTV epoxy with a dense collection of iron filings. The combination yielded candidate 12, which had poor repeatability but fit all of the polymer criteria and exhibited a resistance change when bent or strained. With the promising results of candidate 12, a suitable commercial version of the same type of material was located. This successful material was candidate 13: a silicone RTV suspension of nickel-coated graphite particles (MMS-020, Silicone Solutions, Inc., Twinsburg, Ohio). This material met all of the requirements while exhibiting piezoresistive properties and being commercially available.

Material 13 is a silicone room-temperature-vulcanizing (RTV) material containing conductive particles of nickel-coated graphite (MMS-020, Silicone Solutions, Twinsburg, Ohio). This material is commercially available as a flexible electrical insulating material to ground electronic devices. Although it satisfied the search criteria, none of the detailed piezoresistive or mechanical properties was available.

Material 13 is representative of a group of Room Temperature Vulcanizing (RTV) materials which cure by degassing a solvent reaction inhibitor. Common single part solvent-based epoxies include cyanoacrylite instant adhesive "Crazy Glue" and DWP-24 Wood Adhesive "Liquid Nails. When in the sealed environment of the container, the material remains in a liquid state because the trapped solvent inhibits the curing process. But when applied to a surface, the solvent inside the liquid escapes into the surrounding atmosphere and the epoxy molecules cross-knit and pull together to form chains. When conductive graphite is suspended inside this material the end state is that these particles are close enough together to allow electrons to jump from one to the next when fitted into a circuit with a voltage differential. Combining this silicone with graphite adds the piezoresistive response when the particles are strained apart. Silicon is a good elastomer for the suspension because it is abundant, inexpensive, and thermally stable.

To facilitate solvent evacuation and speed up the curing process alternative filling procedures were considered. By inserting a needle syringe down the filling channel and incrementally filling and retreating the needle there is an opportunity for the solvent to escape back through the filling channel. However this creates boundary interactions between the injection volumes and considerably slows down the filling process. Another option is to vacuum out the solvent through the surrounding AM material by creating a negative pressure. This process would add complexity and for thicker AM structures has a low likelihood for success.

Materials like silicone are well known for their electrically insulating properties, but these can be modified by the introduction (doping) of conducting fillers. Current can only flow through the conductors, and these additions require a minimum concentration to conduct electricity through the polymer bridge, and their curing patterns are modeled according to percolation theory. Percolation theory is a mathematical methodology to understand and make predictions in a continuum of disordered media. Each point in the media is defined by a random variation in its degree of connectivity to its neighbors. It has been used to model disordered systems such as spread of disease infections, adoption of social trends, fractals, liquid intrusion into porous rock, and in this case polymerization of chemical bonds. Statistical percolation theory predicts for the dependence of conductivity on filler concentration as a power law behavior, and percolation threshold refers to the minimum number of connections to create a link between two opposing ends, called a chemical path. The molecular bonds form as the solvent is released, and at the threshold join to form the chemical path. It is important to note that this is not necessarily the shortest or most electrically efficient path between the two end points; it is just the first to form. The formation of the chemical path indicates the first moment when the polymer bridge is able to conduct electricity. Few exact results exist since percolation theory describes probabilities. However some results have supported the theory that the shape of the continuum plays a role in determining the conductivity and percolation threshold. If correct, this theory impacts selecting the geometry of the polymer bridge and injection lines since their length will be the largest dimension of the continuum.

Values like maximum conductivity and percolation threshold can be balanced by empirically determining the shape and size of the additive particles (dopant). Generally, the closer the volume of the insulator resembles the conductor, the low the resistance. Larger particles will conduct better because their presence decreases the volume of insulator the electrons need to pass through, and when examining the particle shape, flakes conduct better than spheres because of their superior 'stacking action'. In some experiments, the resistance values of fibers and flakes decreased up to 17 orders of magnitude when packed with filler. Depending on the concentration of the fillers the mechanical properties can also be significantly impacted. Graphite is a brittle material, and the decreased percent volume of silicone in the mixtures increases the brittleness of the bulk material.

To examine the deposition, shape, and size ranges of the particles a single layer was applied to number zero glass slides and allowed to fully cure. Images of the conductive material were gathered using Differential Interference Contrast (DIS) Microscopy at 10× magnification using a Nikon Eclips TE2000-E camera system. The resulting images indicated that the nickel-graphite is a disordered semiconductor In order to conduct current the particles need to be densely packed, i.e., in direct contact with their neighbors. When the material is strained, the particles remain attached to the flexible silicon but move away from each other and decrease the number of paths for the electrons to travel from one side to the other. The non-uniformity in the shape and size of the dopant particles all add to variability in the resistance of the samples, especially when the samples are small enough it may not be representative of the bulk properties.

During the polymerization process, many pathways will form and network between the two electrodes. The micro pathways' combined resistances are equivalent to summing a large number of parallel circuits for the total resistance of the bridge.

As the polymer is strained the resistance of the pathways will increase to infinity until only one remains. This single pathway acts similarly to the chemical path that it may not be the most efficient, but is the only available conduction route. Since the polymer will always be examined in a bulk state as a fully cured material, there is no practical reason to know the resistance of the individual chemical paths, just of the resistance of the entire continuum (bridge) at complete cure. This bulk electrical property is the resistivity through the volume of the material.

A conductivity test was performed to determine the average unit resistivity through the material volume (as oppose to surface area) which estimates resting resistance of the sensor. Using the guidelines of the ASTM B193 standard, ten samples of uniform length and cross-section were prepared in two sets of tubes. One material was cellulose butyrate, a porous non-reactive plastic to facilitate solvent escape; and the second was glass, which constitutes a non-porous material. Tube samples were within 0.003 in length of the 12 in (or 300 mm) guideline of the testing standard, and interior diameter was 0.125 in (0.3175 cm). Samples were measured periodically for conductivity and let rest for 30 days to ensure full curing even though the conductivity values had settled to 10% of previous measurement after just the seven days. Resistivity was calculated using the following equation:

$$\rho_v = \left(\frac{A}{L}\right) R$$

where:
$\rho_v$=volume resistivity, $\Omega$m
A=cross-sectional area, m$^2$
L=gage length used to determine R, m
R=measured resistance, $\Omega$ During the curing period the samples were kept in a temperature controlled fume hood at 20° C. Measurements were collected with a Fluke 179 digital multimeter, and results were from an average of 5 measurements taken 10 minutes apart after 30 days curing. After the 30 day period none of the glass samples had achieved conductivity.

The range of the samples' resistance varies between 7.1 and 84.6 $\mu\Omega$m with the standard deviation of each sample within 0.03% of its average. The average from the plastic samples is 31.0 $\mu\Omega$m with a standard deviation of 27.4 $\mu\Omega$m. This variability is primarily comes from the wide variety of particle sizes in the tube batches, but the average is still representative of bulk material properties. Shape and consistency of the particles, as well as uniformity of the nickel coating all impact the variability of resistivity. Individual calibration of each sensor to the distribution of its particle properties can take these results into account. In addition this range could be reduced with a more consistent and well-controlled process for size and shape to prepare the graphite-nickel samples. Despite the high standard deviation, the resulting average is consistent with measurements for graphite resistivity. Resistivity values in this test are higher than those of pure graphite are because some of the test volume is taken up with an insulator, which is effectively constricting the electrical flow similarly to shrinking the cross-sectional area.

Prototypes from several AM materials were examined for static and dynamic responses in a controlled setting. The sensors and system was examined for capacitance and drift while is resting conditions, as well as responses to various dynamic loading patterns. The resting drift of the silicone was examined using the sensor samples in a voltage divider circuit at 20 degrees Celsius for 45 minutes. A regulated 3.3V power supply was used with a 100$\Omega$ resistor as the other half of the divider circuit. This first test specimen had a resting resistance of 6.5$\Omega$. No analogue or digital filters were used in the circuit.

The data from both samples show small changes on the order of mV, approaching the data acquisition resolution limit. For an expected resistance change on the order of several ohms, any drift effects appear to be negligible. The small changes in the data may be attributed to the quantization error in both graphs or slight thermal effects in the measurement space.

The same testing setup was used to check capacitance of the material as it discharges after the power is switched off. A diode in series prevented any drain on the samples from the power supply during shut off. Different frequencies were manually activated. For 40 ms following each termination of the power there is a discharge effect. This is a consideration for the maximum frequency of reliable measurement to avoid interference from this effect.

The performance of the sensor is dependent on the behavior of the conductive material as the sensing element. Its electrical response and mechanical limits are dictated by four parameters: three geometric dimensions which define the polymer bridge and one from the mechanical-electrical relations for gage factor. The following section discusses the three geometry parameters. The three geometry parameters affect the polymer's ability to fully cure according to: the volume of polymer inside the bridge, and the volume of material through which the solvent has to escape in order to fully cure. The curing time expected for a particular sensor now also indicates how long one can expect to wait before a sensorized device is ready to be used and take measurements reliably. The impact of these parameters was determined using Taguchi Methods.

Taguchi Design's orthogonal arrays were used to optimize parameters for response characteristics based on geometry dependent variables. This way of modeling will yield relationships to determine effects without having to test a large number of variations of the sensor's polymer bridge. Taguchi methods are strategies based on statistics for the optimization of an objective function by varying the input parameters. Taguchi introduced design criteria for robust system tolerances using orthogonal arrays that allow analysis of many factors with minimal trials. Although this method has been used for mass manufacturing for a long time, recently it has been gaining interest for parameter optimization while designing a new part. Taguchi methods have been used in RP processes for multi-variable optimization of output characteristics like surface finish, dimensional accuracy, and ultimate tensile strength. Studies have examines build parameters for temperature, build speed, and build density have been varied to determine which output characteristic is most affected by each input parameter. This setup allows the testing of all three geometry variables at three parameters without having to run 27 ($3^3$) separate experiments.

Based on the overall size goals of the sensor each geometry parameter was assigned a small, medium, and large value to define the design space. The three parameters were assigned 3 levels and 5 samples of each series were built. Sample series were built using stereolithography (SLA) Acura 40 resin. The chemical interactions during degassing are dependent on the volume to release. Although the SLA resin has a unique reaction with this solvent, it altogether still represents the most challenging conditions for curing since other materials used with FDM, SLS, and MPJ are non-reactive.

When fully cured, the polymer conducts continuously. This is the electrical indicator of the material state the curing time and curing completion is based on the ability of solvent vapor inside the mixture to escape, therefore different combinations of the geometry were evaluated to determine ranking of their impact on this degassing process.

With the exception of tube length dimensions, the experimental procedure and measurement followed the ASTM B193-02 standard. Each experiment was fabricated with the tube length aligned in the build Z-axis for maximum concentricity. This also kept all tube surfaces smooth since no internal supports were generated. Once the SLA material was post processed and fully cured, the polymer was injected into the tubes using a syringe. Observing through the translucent resin, care was taken to avoid air pockets forming. The syringe was not removed until the tube was filled with silicone. Samples were kept in a temperature controlled fume hood at 20° C. Resistance measurements were taken every six hours for a period of seven days.

The control condition was the 24 hour curing period recommended by the manufacturer. When fully exposed to the atmosphere, this allows the solvent to freely escape. The time to first conductivity and the time to stabilize are important values which indicate the ease of the solvent to escape and allow full curing to complete.

As the solvent is released and the molecules cross-knit chains they become closer together and allow electrons to move through as a semiconductor. The patterns of the data follow three stages: (1) the electrical impedance is infinite until the first conductive pathway cures, albeit constrictive and maintains high impedance; (2) rapid decay of the resistance values is an indication of the number of channel options for the electrons increasing to allowing easier flow across the graphite particles; (3) all of the molecules have cross-knit and the resistance values settle to a steady-state as the silicone is completely cured and the high density of particles allows conduction readily.

The five samples within each experiment followed the same patterns but varied in their consistency. Experiments 1, 2, 4, 5, and 8 all have curing patterns that vary, but have similar final resting values. Decay to steady-state values almost completely occurred within 40-50 hours for each experiment after the first conductive instant. To perform the Taguchi analysis, this time to first conductivity was selected as the 'small as possible' process objective since it varied across each experiment.

The geometry factors impacting curing time in order of significance are: bridge length, wall thickness, and inner diameter. This indicates that most of all the length of the polymer bridge should be minimized at 20 mm to promote rapid and complete curing of the sensor, with wall thickness and inner diameter also as small as possible, but have a design window between the small and medium values. Time for the resistance value to settle (stabilize) is the point when consecutive 6 hour measurements were within 10% of the previous value for a 12 hour period. The Electrical Resistivity has also been calculated and included in the table to compare the unit electrical conductance state of the experiment at the end of the 7 day trial. This result is consistent with the general percolation theory, which estimates the time to chemical path is based foremost on length i.e. the length of the bridge has the greatest impact on time to first and steady-state conductance.

The results from this trial reinforce the conclusion drawn that minimizing the polymer bridge dimensions decreases curing time. As experiment 1 was the first to reach curing state it had the longest time to settle and stabilized the most, indicated by having the lowest Specific Electrical Resistance value. It is possible that examining the other experiments for longer than seven days would show similar patterns, but even if they fully cured with a high repeatability this would violate the sensor requirement for having a short lead time of 1 week. The samples which did not reach the curing criteria may also have reached the solvent absorption threshold for the SLA structure, and the leftover solvent continued to inhibit the curing reaction.

The average volumetric resistance of the samples here is roughly a factor of 10 higher than the previous volumetric tests. The SLA housing restricted the solvent release, as well as the length of the experiment terminated 23 days earlier than the volumetric tests. If measurements had continued for the same full time it is likely that the smaller dimensional samples would approximate the previous average, with the likelihood decreasing as the Taguchi polymer volume increased since it will saturate the Accura 40—solvent reaction at some point.

To predict and model the performance of the conductive polymer inside the force sensor, it is necessary to understand its electrical and mechanical reactions to strain. These reactions were determined from testing for Gage Factor (GF) and Poisson's ratio (v). To determine the GF, mechanical elongation and change in electrical resistance were measured simultaneously. Material samples of the conductive silicone were prepared and tested in a tensile mode to strain them, while the change in electrical resistance was recorded. Both sets of tensile tests were in accordance with ISO 37:2011(E) standards for molded rubber dogbone samples. The curing conditions of the samples needed to approximate the interior of the polymer bridge; however a method for producing repeatable geometry and flat surfaces posed the same challenges as curing inside the bridge. Several methods were attempted to make a thin-walled mold to allow the solvent to escape while retaining the desired shape with smooth surfaces. For larger molds the barrier at the perimeter of the conductive material would cure first and block in the solvent gas escaping from the core sections which leaves the interior uncured. Lost wax negatives and thin walled SLA double-chambered molds were some alternative efforts. A substrate material was required which allowed the solvent to escape without leaving a residual texture or crack propagation. Cork, basswood, and several porous thermoplastics were unsuccessful since they could not be removed/cleaned off without gauging and damaging the sample surface.

Foamular 250 extruded polystyrene wall insulation foam (Owens Cornering, Toledo, USA) was successful to act as a secure substrate to support the dogbone surface whilst also allowing the solvent to evacuate. The opposite surface was contacted by thin polyethylene (0.127 mm) which readily peels away leaving a clean surface to apply electrodes to measure resistance during tensile testing.

Samples were left in a temperature-controlled environment at 25° C. for a period of 30 days to fully cure. At this point the polyethylene layer was peeled back and mold alignment tabs were removed. Any samples with cracks, voids, or damage from the de-molding process were discarded.

Ten samples were prepared using the molding methods described above, and testing was in accordance with ASTM D638-10 standards. Measurements were taken using an Instron and dual-axis extensometer at 1 mm/min. Results for longitudinal (axial) and transverse strain are shown in below.

This value is a very low Poisson's ratio for an elastic material. Rubber would normally closer to the theoretic mechanical maximum of between 0.4 to 0.5. However comparing the value to the filler material, in this sense it behaves more like concrete graphite who has a ratios between 0.1 and 0.2.

The likely explanation is that when the samples are molded or injected, the conductive particles (with very low Poisson's ratio) are compacted together inside the chamber, with the micro gaps being filled with the silicone elastomer (maximum Poisson's ratio). When a longitudinal load is applied, the strain elongates the silicone along its axis but there is still very little room for the particles to move closer within the transverse plane. There is very little transverse strain when the bridge in the sensor is flexed, therefore the polymer will not try to separate from the inner cylindrical surface. It is unusual for a flexible/elastic material to have such a low value, but this result is actually very beneficial because it reinforces the assumption that the strain of the flexure is equal to the strain of the conductive polymer.

The Gage Factor (GF) of a piezoresistive material is the relationship between the change in its electrical impedance (dependent variable) from change in its mechanical state (independent variable) of strain. As the name implies, it is usually a single number based off of the linearly-elastic mechanical deformation (with an assumed linear electrical changes associated with it). This is the electrical sensitivity of the gage wire responding to strain. The GF is also known as the piezoresistiviy or sensitivity factor, and can be calculated using the instantaneous resistance or unit resistivity of the material. The latter takes into account the Poisson's ratio for the shrinking cross sectional area. It is desirable to have a high GF value because it will be easier to detect small changes in strain.

When straining a material the cross section perpendicular to the applied load shrinks. So taking into account using poisson's ratio there is another option to use a modified GF equation seen below taking this into account. One of the assumptions for the sensor modeling is that the polymer contained within the bridge does not shift or part with the interior walls.

Some other materials which exhibit this effect are shown in the table below.

|  | Material | Gage Factor (GF) Low Strain | Gage Factor (GF) High Strain | Ultimate Elongation (%) |
|---|---|---|---|---|
| Pure Metals and Alloys | Platinum (Pt 100%) | 6.1 | 2.4 | 0.4 |
|  | Platinum-Iridium (Pt 95%, Ir 5%) | 5.1 | — | — |
|  | Platinum-Tungsten (Pt 92%, W 8%) | 4.0 | — | — |
|  | Isoelastic (Fe 55.5%, Ni 36%, Cr 8%, Mn 0.5%)* | 3.6 | — | — |
|  | Silver (100%) | 2.9 | 2.4 | 0.8 |
|  | Copper (100%) | 2.6 | 2.2 | 0.5 |
|  | Constantan/Advance/Copel (Ni 45%, Cu 55%)* | 2.1 | 1.9 | 1.0 |
|  | Nichrome V (Ni 80%, Cr 20%)* | 2.1 | — | — |
|  | Karma (Ni 74%, Cr 20%, Al 3%, Fe 3%)* | 2.0 | — | — |
|  | Armour D (Fe 70%, Cr 20%, Al 10%)* | 2.0 | — | — |
|  | Monel (Ni 67%, Cu 33%)* | 1.9 | — | — |
|  | Gold Paladium (Au 40%, Pd 60%) | 0.9 | 1.9 | 0.8 |
|  | Manganin (Cu 84%, Mn 12%, Ni 4%)* | 0.47 | — | — |
|  | Nickel (Ni 100%) | −12.1 | 2.7 | — |
| Families of Sensing Materials | Metal foil strain gage | 2-5 | | — |
|  | Thin-film metal | 2 | | — |
|  | Single crystal silicon | −125 to +200 | | — |
|  | Polysilicon | ±30 | | — |
|  | Thick-film resistors | 100 | | — |

*Isoelastic, Constantan, Advance, Copel, Nichrome V, Karma, Armour D, Monel, and Manganin are all trade names belonging to respective owners Platinum is an excellent conducting material available, widely used in semiconductors and integrated circuits, and also exhibits a piezoresistive effect. Note that of the list of pure metals, nickel has the greatest magnitude gage factor which makes it desirable since it is the most sensitive, however it is negative. Nickel and some other metals have an unusual GF in that they are strain-dependant, so will first decrease resistance for low strain, and then change after a point. These non-constant GF values require a separate model. GF is affected by the change in wire length, cross-section area, and the piezo-resistance effect of the wire material. The strain sensitivity factor S itself ranges from −12.1 in Nickel up to 6.1 in Platinum. Material-specific testing is necessary since even between a pure material and an alloy the GF can be quite significant. Graphite is a brittle material so in its pure state doesn't have a GF because its elastic limit is very low.

Figure 17B:
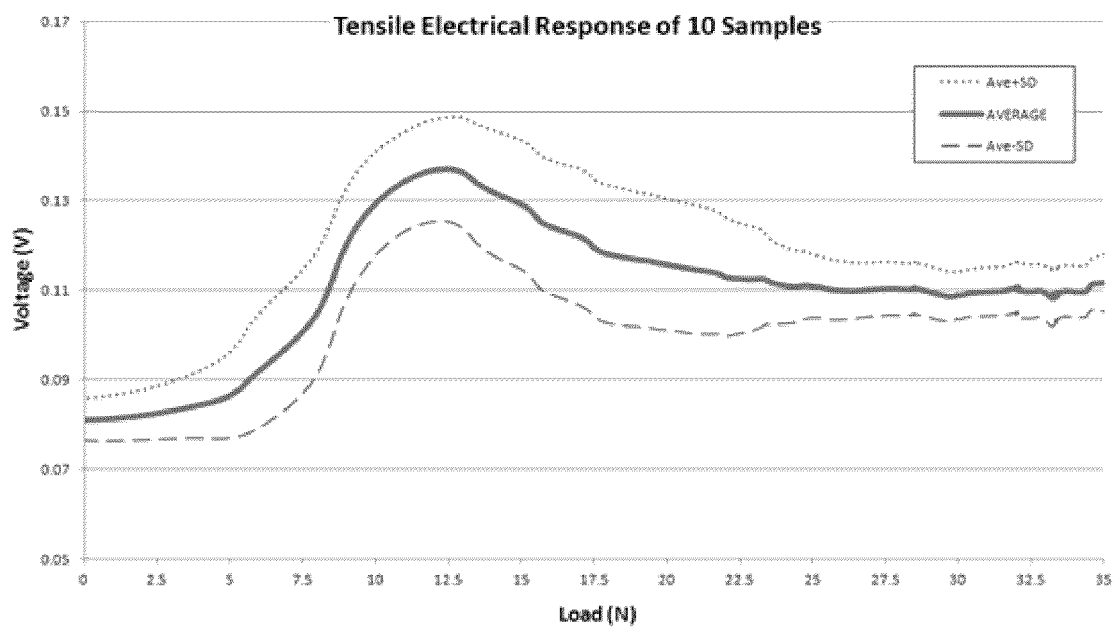
FIG. 17B illustrates electrical response during tensile testing.

The conductive silicone was tested for GF in a tensile destructive test. The testing protocol was a combination of ASTM D257-78 and ASTM B193 standards for measuring resistivity during tensile elongation of a controlled volume. Ten samples were prepared for this testing using the previously described molding technique. The electrodes were surface contacts at opposite ends and sides of the sample to measure the volumetric, not surface conductivity. The outside of the jaws were electrically insulated except through the test sample. All samples were maintained and tests were run in temperature controlled environment at 20 degrees Celsius to avoid thermal changes and effects on the sensing material. A 5V input was used with a Type I quarter Wheatstone bridge, and the signals were post-processed with a $4^{th}$-order Butterworth filter. A first examination of the electrical response to the tensile loading in FIG. 17B shows the failure limit of the samples at 35N and a level-off for the electrical response. FIG. 17B is the electrical response of the ten samples during tensile testing. When the samples no longer conduct electricity, they have reached the equivalent $p_c$ value as the minimum number of particles in contact to close the circuit. Looking at the resistance of the polymer sample as it is strained, this is when the material acts more like an insulator than a semiconductor.

Figure 17C:
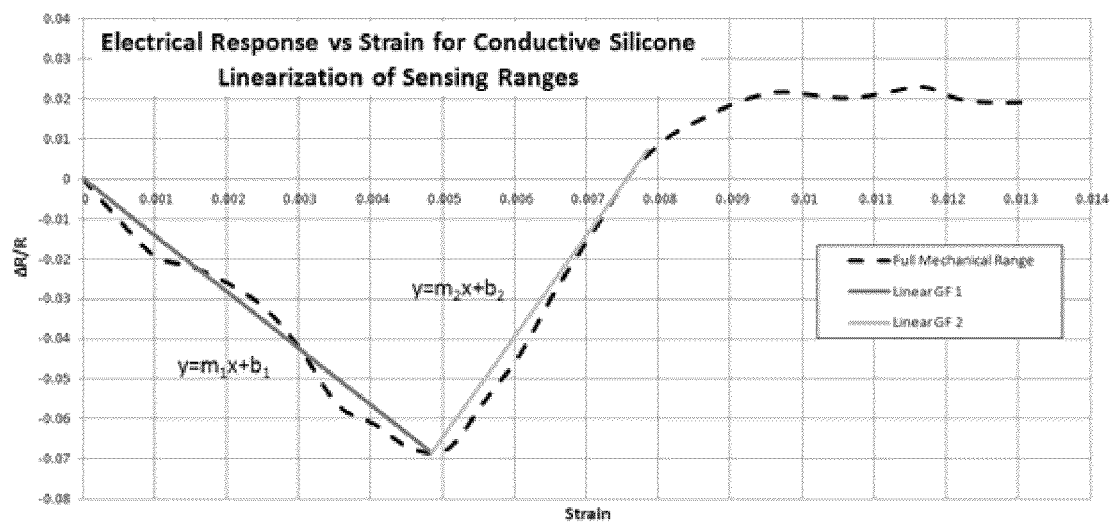
FIG. 17C illustrates Gage Factor plot for conductive silicon.

The mechanical strain and change in electrical resistivity are plotted in FIG. 17C, which shows that the Gage Factor plot for this material is a non-linear function of strain. The shape of the curve for mechanical strain and change in electrical resistivity shows that the dominant GF electrical response is from the nickel coating. The initial portion as a negative relationship, with a clear inflection point before the positive relationship is similar to the response of pure nickel. After a second strain limit the electrical response levels off, which is the sensing range of the material, but is still lower than the mechanical limit. The inflection point was determined from derivative of a curve-fitting, and two linear regression zones were overlaid on the sensing range to divide between low and high strain.

The GF from the first linear portion is comparable to the expected value for nickel in the low-strain state, but the second region is an order of magnitude higher, which is a greater sensitivity to mechanical changes. The second zone was cut off at strain of 0.00863 where the response levels off. This is considered the strain limit for electrical sensing. The gage factor itself was plotted versus strain with the two linear portion overlaid. The variability in the GF from the 10 samples affects the accuracy and repeatability of the sensor once the polymer will be contained within the bridge.

The two electrical response zones were overlaid upon the mechanical response curve. The negative GF region was found to be coincident with the non-linear mechanical zone and the positive GF was found to be coincident with a linear mechanical region.

The ideal sensing material would have an electrical response limit as close as possible to its mechanical limit to maximize the working strain range, and it has a sensing limit greater than the flexure. Each AM material has its own elastic limit and next is to compare how much of the elastic limit the polymer can sense.

An earlier requirement was that the sensor can measure all changes with the elastic limit of the flexure. The figure above shows that this particular polymer cannot sense the full strain limit of the most popular AM materials, in some cases only up to roughly 40% in the case of the SLS nylon series. The electrical sensing range of the silicone is only 9% of its own mechanical range. The sensing range can be altered by modifying the doping characteristics as discussed earlier, however any new formulations would need to be retested mechanically since the two sets of properties are inter-dependent. The measurement range of the polymer limits the force loading capacity of the sensors since they will require a stiffer structure to limit the strain to the upper (or preferably lower) strain inflection point. It also translates better to sensing stiffer materials like the SLA resins or the FDM plastics, although the SLA Accura 40 is not chemically compatible. This leads to the conclusion that the FDM series materials are best initial sensor candidates since they are time-stable, inexpensive, chemically non-reactive with the solvent, and the polymer can detect the largest proportion of their elastic limit.

Deflection analysis using a combination of the beam theory and FEA methods were used to select the geometry dimensions for the first set of functional sensors of the described embodiments. Samples were built using the most prevalent commercial AM technologies and evaluated for performance on a custom linear servotube testbed for loading profiles and magnitudes up to 10N.

The finite element analysis (FEA) was set up to examine the ABS M30i material in linear and bending modes to confirm that the sensor housing geometry can match the strain limit of the conductive silicone.

The initial design was to maintain a point load at the center of the beam by keeping the button diameter small. The simulation was carried out using COSMOS and had a mesh of 66,000 tetrahedral elements, with both end faces of the tube clamped, a symmetry condition along the X-Y plane, and applied the load on the top of the button normal to the bridge at its midpoint. The loading conditions applied were at the 10N range.

Figure 18A:
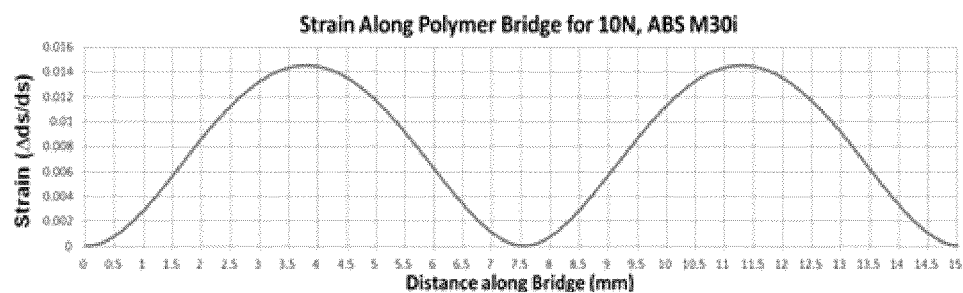
FIG. 18A illustrates longitudinal strain for polymer bridge.

The circumference of the button on the dorsal surface (force application point) was too small, causing the strain to be carried at the center rather than being evenly distributed throughout the polymer in the bridge. These type of stress concentrations need to be avoided since it can damage the silicone bridge even at lower loads. By making the button wider, it theoretically shortens the length of the sensor 'L' because it becomes stiffer. This is necessary when considering the buckling effect around the sides of the button seen in the simulation above as well as making the strain more even along the bridge and minimizing localized effects. For robustness against shear loads it also adds lateral stiffness. The load button radius was equal to $r_o$ in this case. FIG. 18A illustrates some polymer bridge results for 10N static loads—in this case longitudinal strain for the polymer bridge.

Strain Ranges within the bridge based on the FEA are 0.000337 to 0.01475. For a 10N load the analysis shows an average strain value of roughly 0.0078, which is approaching the electrical limit for the polymer's sensing ability. Although there is a range of strain within the polymer bridge, an important consideration is determining what is the representative value for the entire bridge. The GF equation assumes a consistent and equal strain along the element, and when taking the average under the area of the curve, the representative strain is 0.009. This value was used to set the upper load limit of 10N for dynamic testing of the sensor housing.

Figure 18B:
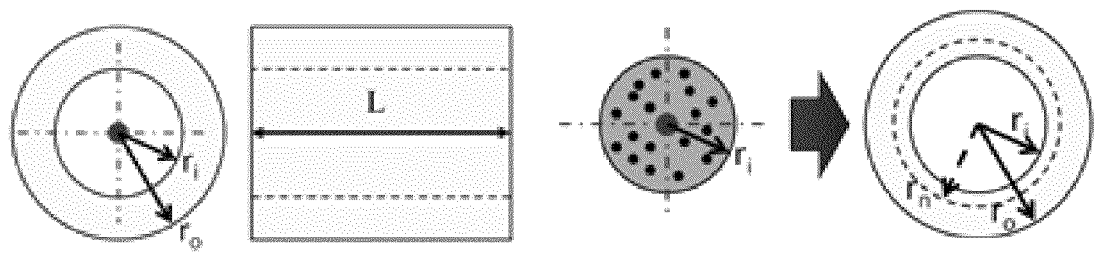
FIG. 18B shows polymer bridge key dimensions and composite equivalency.

With the dimensions of the plastic bridge determined, the impact of the polymer on its mechanical stiffness was examined. The equivalent thickness of the polymer as a layer of ABS M30i plastic was calculated using the following equation:

$$E_{silicone} \in (\pi r_i^2) = E_{M30i} \in (\pi(r_n^2 - r_i^2))$$

and overlaid on the existing cross-section as an equivalent thin-walled cylinder of equal elastic modulus. See FIG. 18B for the polymer bridge key dimensions and composite equivalency. To use as an equivalent E value for the silicone, the minimum and maximum values of 0.01 and 0.1 GPa were used, as these represent the range for rubber materials.

The equivalent wall thickness was below the minimum suggested build settings for using the FDM hardware i.e. even on the smallest feature build settings the wall would already be stiffer than any contribution the silicone would have to resist bending. Thus the simulations could use a simplified model of a hollow cylinder because the silicone is negligible. As a secondary check in reverse, the equivalent wall thickness of the conductive polymer was assumed equal to the minimum build wall thickness (which would add another calculation each time a sensor according to the described embodiment is built), and then solved for what elastic modulus it would have to effect this design constraint on the geometry.

Even if the rubber has an E value identical to the ABS plastic, it would still only be 0.0014142 m thick instead of the minimum wall thickness of 0.001762 m; matching the previous assumption. In addition, solving for the $E_2$ value to see what E is required to make a significant increase in the $r_o$ it would need to be 1.147 GPa. This is larger than upper E value of pure silicone rubber by a factor of 10, which would act more like medium duty nylon or polypropylene thermoplastic with E between 1.5-2 GPa.

Figure 19A:
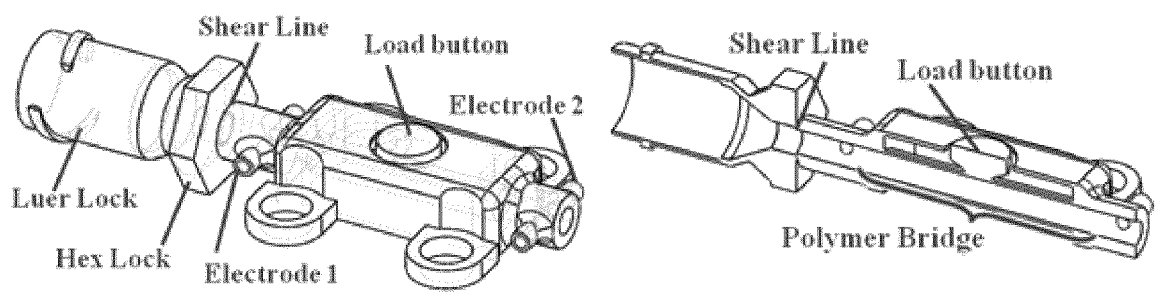
FIG. 19A illustrates a force sensor according to the described embodiment with a Leur lock.

The viscous polymer required high pressure when being injected due to the shear friction along the wall interiors. To account for this, each injection port has a Luer lock thread built into the part body to maintain the seal. FIG. 19 illustrates a force sensor according to the described embodiment with a Leur lock. Once the polymer is fully encapsulated by the channels, the thread can be cleanly removed by breaking along a built-in shear line. The copper wire electrodes are immediately inserted before the polymer begins to gel, and creates a robust electrical contact by pushing aside the neighboring conductive particles. Although the bridge can be embedded into any shape of housing, the configuration in FIG. 19A is compact enough to build and test the force sensing principle.

During the build platform preparation phase it was important to adjust the software's layer slicing parameters. Features with small curves and rounds like the polymer bridge can sometimes be interpolated out of the build. The original STL file had solid features but the top and bottom surfaces of the bridge in the bff file were missing because the angle between layers was below the default threshold. The final CAD for one sensor constructed according to the described embodiments was able to be built in the SLA Viper with no internal support structure. The build orientation and build parameters were adjusted to ease post-build cleaning.

One of the goals for the sensor design was that AM components could be built in nearly any service bureau, and either the end user can insert the conductive elements themselves or the vendor can easily add it to their service capabilities. This also necessitates the conductive material itself to be readily available and not require any special handling procedures outside of normal laboratory and AM safety. The filling strategy does not require complex hardware or procedures, and limits image of filling by using breakaway injection ports. During filling the silicon is able to move through the channels to the sensor site in its liquid state without deteriorating. The selected material is able to cure within the hollow chamber for the sensor, in conditions of ambient temperature and pressure. Many conductive materials and silicone rubber suspensions were eliminated from selection since they commonly require vulcanizing conditions with high pressures and temperatures above the creep values for AM thermoplastics as well as many SLA resins. A commercial injection gun with an 18:1 thrust ratio was modified to receive and reinforce a polypropylene syringe with Luer fitting.

Samples of a sensor constructed according to the described embodiments were built from commercial techniques which have plastic materials. The FDM Parts were built in ABS-M30i (Redeye on Demand, USA). This material is ISO 10993 certified with biocompatibility suitable for a device with prolonged superficial contact. In addition, the FDM machine selected utilized a soluble support structure to clear the internal voids of the sensor without damaging it.

The SLA Accura 40 has similar mechanical properties to nylon and is able to be heat-treated by annealing. The MPJ sample contains multiple materials and is built with the most rigid and most flexible options available for the structure and bridge, respectively. A gap was originally left between the flexible button and the rigid housing but during the build the close edges became fused together with yielded three heterogeneous material boundaries rather than two. SLS nylon 12 is also biocompatible and offers similar properties to some thermoplastics used in the medial and orthotics industries.

Overall, sensors from each material were able to be fabricated and conduct electricity i.e., fully cure. The SLA samples were the slowest to cure, taking roughly twice as long as the other samples. This is due to the chemical reaction of the resin during solvent degassing. The challenges with the polymer seeping through the layers in the FDM part could be mitigated by increasing the wall thickness. The MPJ sample had some residual expansion since the flexible bridge had unconstrained features during the injection process. MPJ was also the only family of sensor samples where failures (bridge ruptures) occurred during filling. The SLS nylon samples has a more coarse finish and thus higher injection pressures were needed. For future parts with a flexible polymer bridge it is important to minimize the volume of conductive material which needs to pass through during the injection phase.

Immediately following injection while the polymer is still in a gel-state, electrodes are inserted on either end of the bridge. The location and alignment of the electrode sites are outside of the polymer bridge to minimize the risk of the graphite particles pulling away from the copper leads when the bridge is deflected. Electrically the sensor constructed according to the described embodiments is closest to a strain gage, or a very low-resistance FSR, and the electrical circuit to acquire the analogue signals from the embodiment is a Quarter Wheatstone bridge type I with a built-in low-pass filter.

The analogue signals from the circuit are taken into the data acquisition hardware as a floating source differential measurement since the variable signal needs to be compared with a respective source which is not Earth. The other resistors in the Wheatstone were selected to maximize the voltage change with respect to the $R_s$. During sensor refinement it was observed that the carbon film resistors would overheat over the course of approximately 1 minute, leading to sensitivity degradation in the measurement. To account for the relatively high 200-300 mA current draw, the Wheatstone circuit was constructed using ceramic resistors.

Testing

To examine the electrical response of the polymer inside the bridge of the constructed sensor, controlled loads were applied to the center of the button, normal to the bridge. Load magnitudes were in series of 2, 4, 6, and 10N, which would test up to the theoretical maximum strain within the bridge.

The linear dynamometer was built to evaluate the electrical response to mechanical stimuli for testing and calibration of force transducers and load measurement sensors; specifically the piezoresistive response of the conductive polymer & sensor specimens. It can apply a static or dynamic mechanical force profile using a Servotube (XSL-230-18, Copley Controls, MA) to deliver a compression force to the bridge unit under testing, with an off-the shelf precision miniature load cell (LC302, Omega Engineering, Stamford, Conn.) in series for measuring applied input force. The response calibration is carried out by correlating the input force as recorded by the load cell against the output of the specimen under testing. The servotube is a rod-shaped series of permanent magnets which are propelled by current generated in the copper windings at the center of the electromagnet base mount. The servotube amplifier has its own built-in PI controller when using the control voltage signal. It can operate like this using only the input current to the servotube, or in closed-loop mode from the load cell measurement.

Each of the loading profiles is generated by a Labview (National Instruments, Austin, Tex.) GUI from a desktop computer and uses a BNC 2110 DAQ. Dynamic profiles are ramp, square wave, sawtooth, or sinusoid. From the GUI the parameters of the dynamic tests for amplitude, phase, and frequency of each pattern can be set. Both the load cell and sensor have an analogue low-pass RC filter set for the acquisition rate of 500 Hz and a $4^{th}$ order Butterworth filter in the Labview VI. The raw sensor value (B) is compared to the load cell before and after the digital filter is applied. A built in 60 second timer automatically runs the test pattern then records each array of data in a new txt file named with the values of its loading parameters.

In addition to force calibration, the system also allows characterizing the frequency response function for the sensor test sample. The dynamic testing examined sinusoid, square, and sawtooth force profiles for amplitudes between 2 and 10N at frequencies of 2, 4, and 6 Hz using the servotube testbed. Samples were placed near the servotube and coils to confirm that no interference was coming from the electromagnets.

The Accura 40 samples were unresponsive to all loading profiles and amplitudes up to 10N. The signal was erratic and no perceivable changes were observed from the loading. This low sensitivity is from the chemical degradation on the inside of the polymer bridge so that mechanical strain is not necessarily translated to the conductive material inside. The only noticeable change in these samples was after mechanical failure when the polymer bridge was broken and the circuit became open.

Figure 19B:
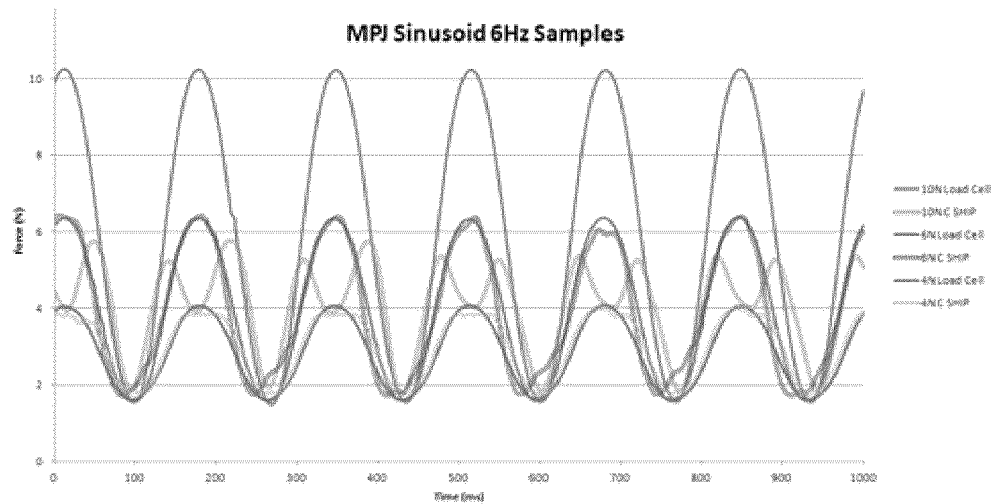
FIG. 19B illustrates MPJ sample sensor and load cell responses to 6 Hz sinusoid.

The MPJ (Multi-Polymer Jetting) samples fully cured and results were evaluated. For example, FIG. 19B illustrates multi-polymer jetted sample sensor and load cell responses to a 6 Hz sinusoid. The 10N samples exhibits a dip in the middle of the sine wave responses because of the non-constant gage factor of the silicone. This shows that the 10N load strains the bridge enough to pass the first strain line and almost saturates the sensor. There is some hysteresis response seen in the 6N series between the rise and fall of the load.

Using the MPJ fabrication technique, a single material modality was also examined (VeroWhite) where the entire flexure is made from a single material, rather than the combination of rigid and flexible.

The FDM samples fully cured and results were evaluated. A 30 minute drift test was conducted for the constructed sensor in the FDM flexure at 2N amplitude and frequency at 0.4 Hz. Signal output was evaluated at the start and end of the trial.

Both the MPJ and FDM samples showed responses in synchrony with the loading profiles, while varying accuracy and hysteresis. The effect of the non-constant gage factor is apparent in the higher-amplitude tests. Two solutions to this effect are to either reinforce the bridge to limit the amount of strain to within the first linear portion, or to have a data acquisition pattern which examines the past state of the measurement to determine whether the voltage value is referring to the first or second linear strain portions.

Although these results have been obtained for a specific formulation of conductive silicone suspension, it is not unreasonable to assume that other solvent-based conductive silicone materials would behave similarly. The influence of density of the graphite particles could potentially impact the curing time considerably since the solvent is contained in the volume of silicone suspension, but this would then also impact the mechanical properties of the material performance, as well as the conductive properties.

A single curve from each was lined up according to timescale, then the MPJ was normalized to match for amplitude with the FDM. The MPJ material is much softer so returns easier as the servotube was retracting from applying the load. This would explain the faster response compared with the FDM who has a greater spring return but slightly slower response time. Additionally, the amplitude is not necessarily the same because the different materials are deformed a different amount. The low resistance of the polymer bridge means that the sensor draws a relatively high amount of current and the resistors in series get hot. The electrical supply and conditions circuit needs to consider heat dissipation because of the high current draw for the polymer. In the Wheatstone bridge matching the other resistors with ceramic elements was key to maintain a power balance after several minutes of continued operation.

The response from the drift test was similar to the thermal effect, even when using higher wattage components. When the circuit was powered down and allowed to rest for several minutes it could return with the same fidelity using the same calibration settings. This indicates that the drift is primarily an electrical or thermal effect rather than mechanical fatigue.

Some challenges with using the AM materials arise from the speed at which they return to their resting positions, and overall visco-elastic behaviors. Although the MPJ samples had high sensitivity from their low material stiffness, they were pliable and adhered to the surface of the load cell when the sinusoidal profiles were applied. They also had a low maximum force range since their elastic limit is above the conductive silicone and stiffness is far below the profiles being applied.

Torque Sensor

The injected polymer bridge constructed according to the described embodiments was applied to a flexure as a customizable torque sensor modality. Commercial torque transducers use bonded metal foil strain gages to understand mechanical deformation of the housing. Just like their similar counterparts the force sensors, they detect the shear stresses in the torsion bar from an applied torque. The constructed polymer bridge can also function as a torque sensor if arrayed parallel to the axis of applied torque, the axis of rotation of the sensor. The description herein for a force sensor had design and testing of a specific force sensor configuration using a variety of AM materials. The following description addresses the reverse: using a specific material while adjusting the geometric configuration to meet the desired specification.

Figure 20:
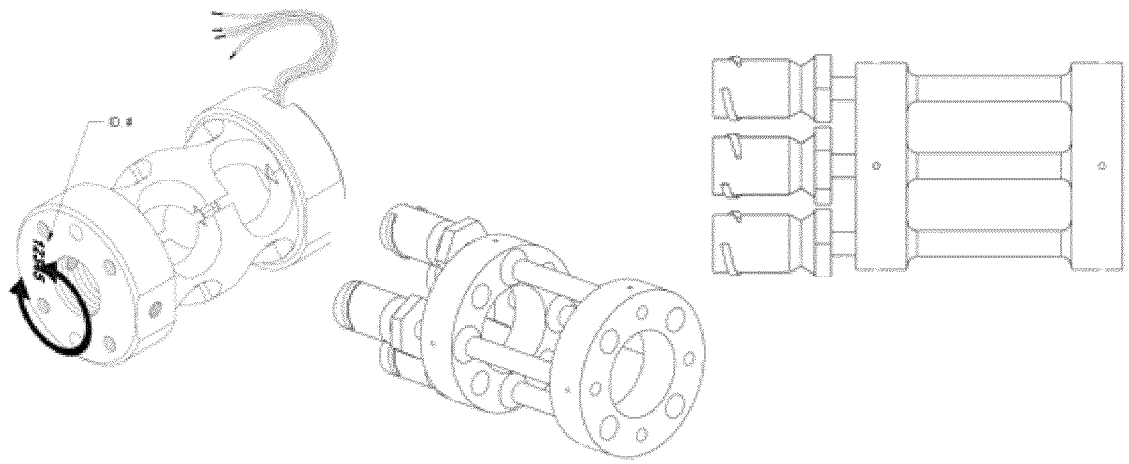
FIG. 20 is an example of such a commercial (Futek) torque sensor.

The described torque sensor embodiments use statics principles from commercial variations of torque sensors. See, for example, FIG. 20 for an example of such a commercial (Futek) torque sensor. In this case the bonded strain gage conforms to the circumference of the fillets as they strain, so the design was modified to place four polymer bridges in cantilevered shear configuration. To keep it as compatible as possible the fasteners and mounting configuration was kept consistent with the Futek.

The electrode configuration and polymer bridge inner & outer diameters are identical to the force sensor design, as well as the injection methods using the luer syringe lock. Before getting to a load-bearing version, fabrication challenges were assessed up front with a 'Series 1' design built using SLA and FDM and injected with the silicone. At first the outer diameter and overall length were kept consistent with the commercial sensor from Futek since it interfaces readily with the other devices which are designed to its geometry. The polymer bridges were moved to the outside edges of the radius to maximize the shear strain resulting from a torque. Torque Sensor Series 1: Thin polymer bridges with the same non-parametric design were used, The SLA version was able to build but as discussed herein, there were issues with the solvent degrading the inside of the bridges.

Torque sensor series 2: Straight parallel channels kept to respond in tension in either direction, with focus on Negative Space rather than positive. Fillets were included to remove stress concentration areas where the bridges meet the flanges. Examples were built with Small and Medium Loading series (0.2 Nm and 3 Nm respectively).

Varying the angle of the cut between the four bridges adjusts the torque value which induces the max polymer strain. The outer diameter was maintained even with the commercial equivalent to ease integration with existing devices. The inner and outer radiuses were kept symmetrical about the polymer bridge at the minimum.

Dimensions fixed for operations were $r_b$ and $r_o$ [the former is as close as we can get to the outside edge for safe build resolution and we can maximize the strain measured. It is not a good idea to place them at the interior of the torque sensors since the difference in strain between the outside perimeter and the interior where the bridges are would be strained past the elastic limit. i.e., the exterior would be plastically deformed before the torsional strain had reaching the inner material.

Assumptions when modeling the torque sensor FEA were similar as for the force sensor:
  There is no internal slip between the polymer and the bridge
  Even average strain is most important along the bridge since the particle distribution is expected to be homogeneous
  There is negligible strain at the flanges and no motion at the electrode-polymer interface Simulations show that the interface between the fillet and the bridges are the locations of highest stress and thus highest shear and are susceptible to failure. They also agree with the calculation assumptions that the flanges undergo negligible deformation, especially around the site of the electrodes. Results for stress distributions are comparable for both geometries.

The injection fittings normally found on the end of the polymer bridge were left out of the Series 2 built parts because the wall thickness required for the bend was below the resolution threshold for the FDM and from the Series 1 small delaminations were visible which would rupture if pressurized during injection. Series 2 samples were successfully filled via syringe retreating from within the bridges.

After 72 hours measurements were taken every 1 hour for 8 hours to confirm that the polymer had fully cured and reached its steady state resting resistance value.

Static and dynamic testing was conducted. The goals of the testing were: (a) confirm the sensors work with the new polymer bridge configuration, (b) examine the sensitivity to the loading ranges advised from the FEA models, (c) examine responses to static and dynamic loading profiles. The test setup mechanically grounds one end of the sensor and loads the other end with a mass while measuring deflection angle and load on the end of the arm.

Weights were hung at the end of the load arm on a linear track to guide and ensure that loading was perpendicular to the arm. For dynamic loading, a spring was placed in series with the tensile load cell, elongated to 0.08 m and released to examine the dissipation of energy while measuring the sensor's decaying oscillations.

To examine the sensor measurement at point of failure, the arm was strained sinusoidally with increasing oscillations until mechanical failure was pronounced. Measurement contrinued several cycles afterwards.

Comparing the dynamic tests for the two flexure shapes, the weaker structure deflects as expected. The Differences in the angle of rotation versus tensile force show that the flexure can be designed of varying stiffness for anticipated loading ranges while using the same internal dimensions and methodology for the polymer bridge. The dynamic performance of both sensors was closer to the known values than the static testing, possibly from the elastic spring effect in the sinusoidal loading and energy dissipation tests. For the static calibration trials, the high standard deviation makes this configuration challenging for slowly changing loads. However the dynamic performance is more encouraging, as it was able to detect the peaks of the higher frequency oscillations when releasing the mass.

Examining the failure mode of the torque sensor, it matches the FEA model for stress concentration, and expected magnitude. Looking at the response during and after mechanical failure, it is still able to measure change in load, albeit at a different signal output range after the break. This indicates feasibility for use as a monitoring sensor for the state of the material since it functioned in torque measurement, point of failure, and strain post-failure.

In some of the manually applied loads it is visible where the polymer crossed from the first linear GF zone into the second (regions A where the signal response inverts after crossing the strain threshold). Although it is a consideration for the sensor's operation, the greater challenge is that once it had crossed into the second GF zone it did not return to the same resting state and had to be left for several minutes to return to its unloaded shape. This is a combined effect of the slow spring return of the FDM material, and some characteristic of the polymer, likely a persisting strain in the bridge.

Impact Sensing Shear Pin

Figure 21:
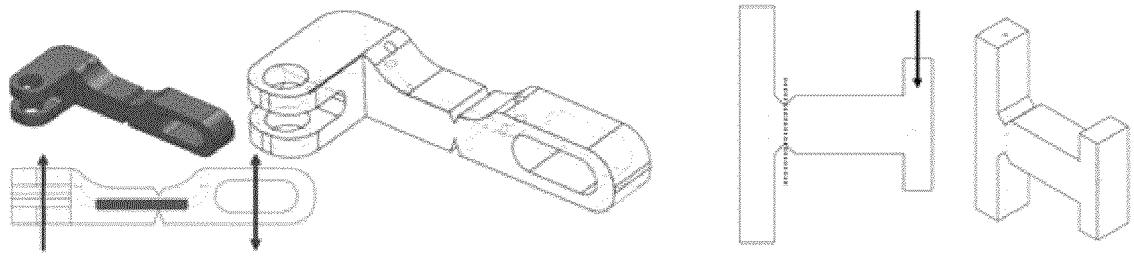
FIG. 21 shows a polymer acting like an instrumented shear pin between two zones.

In the force and torque modalities of the sensor, its responses significantly changed after mechanical failure. The Impact sensing modality uses this property as a conductive switch to indicate when the housing has broken. For measuring interaction forces to safeguard past a set threshold, the polymer can act like an instrumented shear pin between two zones as shown in FIG. 21.

When the polymer bridge is replaced by an unstrained conductive channel which passes under shear line on a part, it can operate as a digital switch or an analogue sensor to detect the interaction forces between the two moving elements and will open the circuit in the event of a mechanical failure. Although designed and tested as a single component bracket, the conductive shear line could operate as an embedded sensor. As an added benefit for impact sensing for a wearable brace or fail-safe for human-robot interaction device, breaking the pin can activate a call for assistance from a fall or end the cut power as a hard stop to the machine.

Impact testing was conducted based on the methods in the IZOD notched Impact Test [reference ASTM D256]. Three groups of five samples were built per material: brackets with and without hollow tubes, with a group of hollow samples injected with the conductive silicone L-bracket components were fabricated with and without hollow channels for the polymer. The three groups of trials examine the dynamic mechanical effect of removing material from a part cross-section to make room for the sensors, as well as the sensing gel's effect on the failure mode of the part. The cross-section of the tube is within 20% of the polymer bridge sensor, so matches the fabrication capabilities explored thus far. Five samples of each test group were built for two brittle materials from SLA and MPJ systems.

The figures below show responses from the sensors during the test. Important to note, these data have no analogue or digital filtering from the sensor, showing that at the peak velocity of the swing arm, the voltage spike is already an indication of impact, followed by a discrete step in voltage when the Wheatstone bridge becomes unbalanced from the missing resistor.

Trials were compared based on velocity after the moment of impact. Although the mass on the end of the moment arm was selected close to storing kinetic energy to break the samples, the differences in SLA and MPJ were relatively small. The effect of the different cross-sections is shown by the ending velocity after the impact. Compared to the control group's velocity the SLA samples showed no difference by removing the material for the cavities, whereas the MPJ groups had some minor differences by adding the geometry of the channels. The MPJ samples all appeared to absorb energy equally from the swinging mass, indicating that addition of the channels and polymer had negligible differences intra-test.

When examining the mechanical failure mode of the three samples, the group with the polymer inside the channels was less explosive for both materials. The two groups without the sensors shattered from the shear line upwards, whereas the sensorized materials broke cleanly into two pieces, in some cases with the polymer still inside the channel, albeit torn. This indicates that the presence of the sensing material does impact the energy absorbed at the moment of impact for a damped effect.

Of the available materials, the family of conductive elastomers was successful in building a piezoresistive sensor to measure force in a compact, customizable housing. The process model was successful to create sensors injected into AM structures able to sense a variety of loading profiles and magnitudes.

The Accura 40 can work as a binary state sensor like an on-off switch if fast curing is not required, but is not suitable for an analogue sensor. The MPJ and FDM are both good processes to use, and come with their own options and advantages. The MPJ has wider material selection for flexible structures in the low-force sensing range while the FDM is less expensive material which is also biocompatible.

Several AM materials were able to record static and dynamic mechanical loads under varying conditions, including forces applied directly by a human. To calibrate the sensor before use, it would benefit to have some similarities to preparing an industrial FSR. Applying a known force five times and adjusting the scale and offset would be routine using an OEM force sensor applied to the surface button of each sensor constructed according the described embodiments that are embedded in the device.

Thus the following summarizes the process steps for creating an AM medical structure with integrated piezoresistive sensors.

Scan wearer's surface areas for medical device
Select type of force sensor to maximize deflection for sensing range
Integrate CAD for selected sensor geometry into device CAD
AM Fabrication
Inject Polymer into hollow tubes and insert electrodes
Breakaway injection lock fitting Other embodiments may use conductive material from the graphite silicone group. In general, any conductive elastomer which can cure without requiring degassing of a caustic solvent, or at least a smaller amount then it may be usable for the described embodiments. Adding the conductive elements via injection post-build is in most cases functional, but brings unnecessary constraints and errors. Many of these complications could potentially be eliminated by adding the conductive material during the build rather than afterwards.

The description below provides exemplary implementations of using sensors constructed according to the described embodiments in devices for upper extremity biomechanics measurement.

Figure 22:
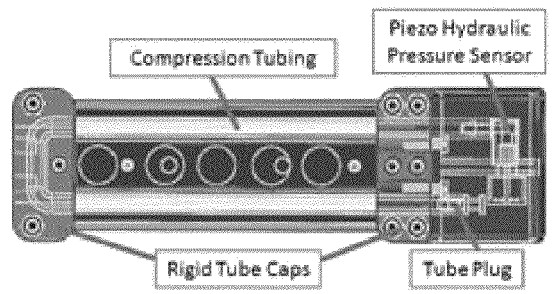
FIG. 22 shows a handle design.

The handle design shown in FIG. 22 is a type of hydraulic dynamometer designed for a stationary exercise bicycle but can be used as a general computer-interface for retraining. The bike version measures applied forces to control dynamic motion and steer the rider in a virtual environment generated by a computer. The initial prototype is inexpensive compared to alternatives with a compression load cell, and the built-in compressibility and spring return of the hydraulic chambers provides a haptic feedback to the rider as they increase isokinetic forces. The handle diameter and contours have been selected to provide the greatest ergonomic comfort for grasping while allowing the user to comfortably maximize their isokinetic strength. It records a measurement from dorsal and ventral surfaces but is unable to detect forces from individual fingers.

Figure 23:
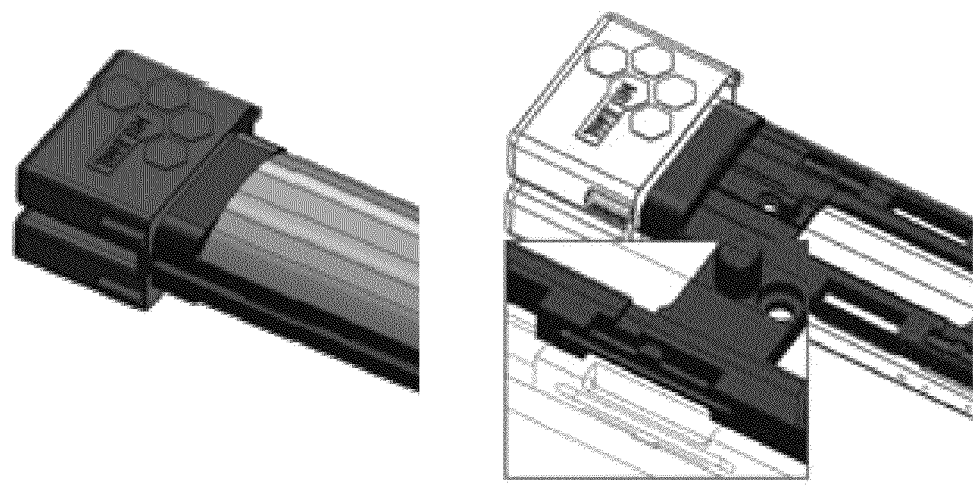
FIG. 23 illustrates a alternative version of the hydraulic handle depicted in FIG. 22.

The sensing area of the handle is the surface area of the paddle which then contacts the tubing. Tubing under the handle caps is constrained according to the tube minimal bend radius and reorient without kinking. Each channel of the two hydraulic chambers will be embedded along grooves in the housing, and thermally bonded together to maintain a close seal at higher pressures. The handlebars will be calibrated individually to match the force applied over the tubes to the voltage resulting from the pressure in the hydraulic chambers. FIG. 23 illustrates a alternative version of the hydraulic handle depicted in FIG. 22. FIG. 23 utilizes sensors of the described embodiments rather than hydraulics.

Figure 24:
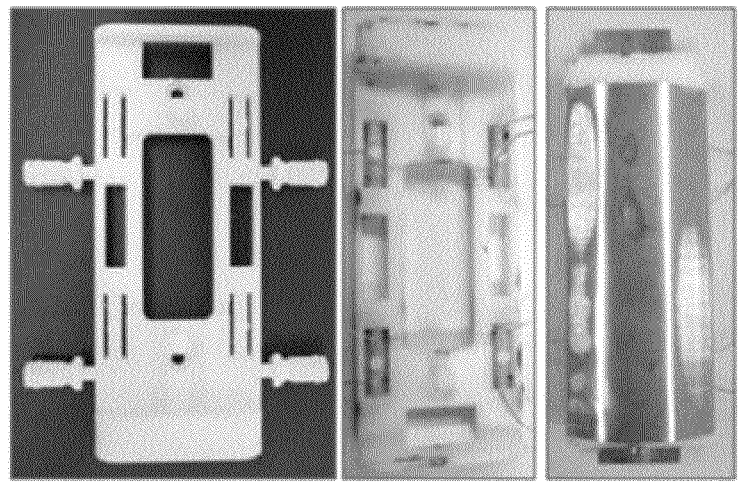
FIG. 24 illustrates the fabrication and injection stages of the handle depicted in FIG. 23.

FIG. 24 illustrates the fabrication and injection stages of the handle depicted in FIG. 23. The four syringe locks (i.e., the Leur locks described herein) are visible in the far left image, and then removed after the polymer has been injected.

Both devices were tested using the electromagnetic servo-tube actuator setup discussed for testing the force sensor herein. Loading amplitudes ranges from 0.5 to 10N of controlled regular compression in sinusoidal and sawtooth waveforms, followed by manually controlling the load. Manual loading was applying tensile forces on the handle surfaces through the tension load cell and comparing their results. The same experimental setup can be used to load the instrumented devices for benchtop testing.

The linkage to load the sensing handles was rigid along a linear guide, the underside surfaces of the aluminum force paddles was machined to match contact with the sensors. For the hydraulic handlebar it had semicircular grooves to match the tubing, for the described embodiment sensors it had two flat surfaces along the length to contact the load button heads.

The first procedure was a static calibration on the hydraulic handlebar. After using the smaller weight to confirm that the calibration values, dynamic testing occurred for sinusoidal patterns for varying amplitudes and frequencies. Each dyanmic test lasted 1 minute and the handle was allowed 1 minute between trials to rest.

The manual input was a load applied by hand on the servotube to pull the tension load cell in series with the hydraulic handle. Although within the frequency range of the dynamic testing it was performed to examine the result of a randomly generated frequency and amplitude from a human user.

The manual loading for the dynamic testing of the handlebar with sensors constructed according to the described embodiments was applied at the load bar. Both hardware configurations were able to measure static, dynamic, and manually applied loads. The hydraulic handlebar had a complete characterization and after the $6^{th}$ iteration is robust enough to be used in a clinical setting. During testing setup there were several higher impact dynamic and impulse loads which could have broken seals or damaged the hardware but it maintained its performance. The handlebar with sensors constructed according to the described embodiments was able to measure forces and key contacts. The sensor was able to be embedded into an existing geometry design for a handlebar housing and acquire and log data. To avoid any interference from electrical degradation during testing, the sensor and circuit were given one minute between trials to rest. Some of the loading peaks and troughs were not picked up by the handlebar with sensors constructed according to the described embodiments, more likely due to the mechanical elastic behavior than the electrical performance since the spring return is slower than electrical dissipation.

The contact between the electrodes and the polymer is a delicate interface and potential source of noise & signal degradation. Some embodiments refine the insertion of the electrodes to ensure a solid mechanical connection functionally equivalent of soldering a wire to the lead. For human testing, other embodiments include a wider group of devices and shapes with which to test specific grasping tasks and hand configurations using the injected sensor as a modular embedded geometry.

Excelsior is a hand-wrist device for a user post-stroke to measure and assist in hand extension & cognitive repetitive exercises to encourage neuro-plasticity. Details of the Excelsior system may be found in U.S. Patent Application No. 61/566,737, filed Dec. 5, 2011, the contents of which are hereby incorporated by reference herein in their entirety.

The sub-assemblies of the Excelsior system were examined for how the sensing elements could be embedded using less time, fewer components, and less expenditure. The Target Objects and LED Thimbles were both redesigned using sensors constructed according to the embodiments described herein.

The force sensing design was modified to fit inside a cylindrical puck design. Several of these cylinders were fitted into the cavities of a hollow spherical object design to prehension studies to evaluate the contact surfaces when performing grasping exercises.

The three pucks were calibrated with static weights before they were inserted into the spherical object. They functioned when inside the object, operating independently with three amplifier circuits were able to independently register contact from the fingertips at varying degrees of exertion. Future work will involve comparing the interaction force with a known measurement on each fingertip and specific grasping task objectives.

Conductive LED Thimble and Visual Feedback Tools

Fabricating the first version of the conductive thimbles was time and energy intensive, requiring several stages of preparing the electronics, molding, casting with components suspended inside, and then wrapping the copper mesh. In the version constructed according to the described embodiments, hollow channels were designed inside the thimble which acts like a wire. Each thimble is a self-contained circuit connected to a battery. The injection ports for the wires are located under the finger pad area, and when removed are the two contact points for closing the switch that activates the LED on the dorsal surface. In one embodiment the closure occurs when the two contact points come into electrical contact with a conducting material, such that the two contact points are electrically connected to one another through the conducting material. In another embodiment the closure occurs because the conductive material associated with one of the contact points is situated in a cantilever arrangement such that contact with any material, conductive or non-conductive, causes the contact points to be in electrical contact with one another thereby closing the circuit.

Figure 25:
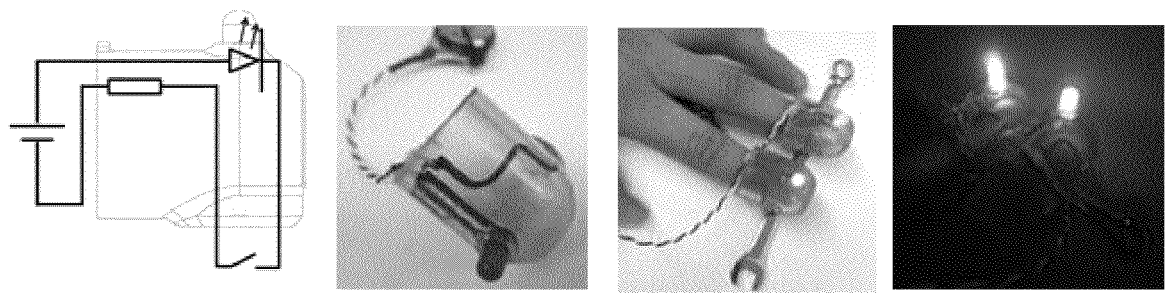
FIG. 25 shows channels embedded inside a thimble switch.

This relatively simple implementation is more robust than the original and fabricated in a single step, with the injection phase following. As shown in FIG. 25, channels are embedded inside the thimble switch. An LED is inserted in series with the battery and wires, once the injection ports are broken off. The injection site acts like electrodes of a momentary switch. The conductive thimble can be used as a contact switch or a metallic detector for exercises or games.

Figure 26:
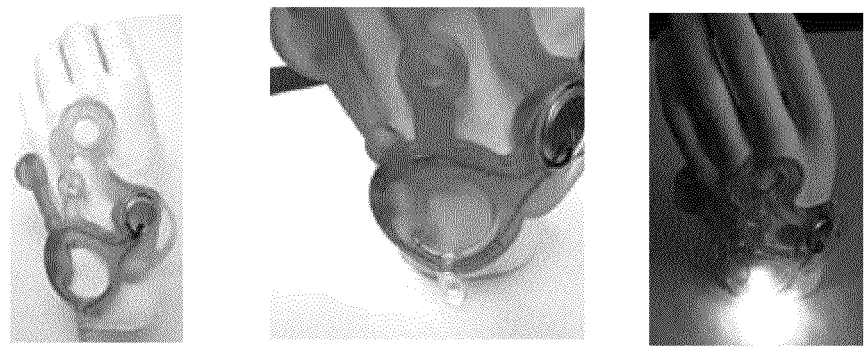
FIG. 26 shows a two part custom-designed wrist-mounted electronic device with embedded channels.

In FIG. 26, a two part custom-designed wrist-mounted electronic device is shown with embedded channels for implementing conductive paths (i.e., wiring), on board battery with LED indicator, and magnetic lock. When the channels are not strained the conductive material within the channels acts as a wire due to minimal time-dependent capacitive properties. The hand piece exterior was built as two parts designed from a 3D scan of the mannequin hand. When they encase the hand the circuit closes. Without straining the conductive polymer it acts like wire. In this case for supplying power to an LED to back light an image embossed in the SLA Accura 40 plastic. When the two halves are close enough for the magnets to secure them, the circuit closes between the two halves and the indicator light activates. For hand dexterity or balance exercises which require the wearer to complete a task, visual feedback can indicate success. Similarly, the wires can be used to connect an auditory feedback via piezo-buzzer in addition to the LED light.

The graphite suspension has a higher resistivity than pure copper or other metals which make up wires, but can still transmit power consistently when injected into a part. Using the same types of injection ports and hardware, the tube cross-section can be specified to act similarly to small resistors in series to limit current draw. This gives options for resistors being distributed along the wire, and by varying the doping concentration or cross section achieving different resistive properties.

The fit of an Ankle-Foot Orthosis (AFO) directly affects its function, including large surfaces and detail features. For example, maintaining a high comfort level around the calf band and around the leg are important so that the fibular head sustains minimal or no pressure. Posterior Leaf Spring (PLS) AFOs have a particular trimline configuration which allows them to treat drop foot well by reducing plantarflexion during swing. However patients who have severe swelling or edema, unstable ankles, or other ankle-foot deformities cannot use generic posterior leaf orthotics because the mass-produced fit is poor. In addition, patients with multiple foot ailments need a customized AFO that can be made available to them quickly for a low cost. In fabricating the RP AFO the aim was to match or exceed the effectiveness of a standard AFO in terms of supporting and controlling ankle mechanics while providing superior comfort and fit by customizing it to the subject's specific anatomy and needs resulting from impaired gait.

Figure 27:
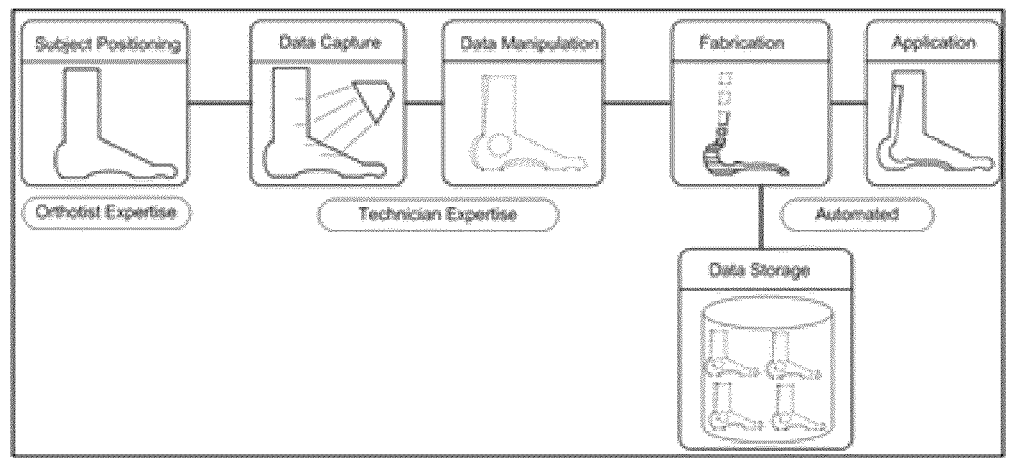
FIG. 27 illustrates a process for creating a custom RP AFO.

The digital process model expands on traditional orthotic fitting, fabrication, and treatment by preserving the value of experience and quantitative design goals of the orthotist, and minimizing the manual labor operations and processes which are difficult to record. Automating fabrication retains geometry selected from key biomechanics parameters by the practitioner while improving speed and availability of a custom medical device. By keeping a digital record of each patient it eliminates the costly need to warehouse physical copies of the leg busts. A long-running record also allows a practitioner to revisit previous stages of their anatomy and compare changes over time for musculature definition and residual pronation. The physical location of data manipulation, fabrication, and data storage are no longer necessarily adjacent to the form capture in the orthotist's clinic because all of the AFO modeling stages may be transmitted digitally. One of the greatest benefits of the integration of these technologies with the current orthotics field is that their cost and involvement is scalable to the orthotist. FIG. 27 illustrates a process for creating a custom RP AFO.

Operations were refined for utilizing patient-specific anatomical surface data from a 3D scanner, manipulating the surface data to an optimal form using Computer Aided Design software, and then downloading the digital output from the CAD software to an RP machine for fabrication. The new selection of using Nylon 11 powder offered ductile material properties similar to the range of polypropylene currently used by orthotists. In addition the material is time stable and washable, and does not leach to the skin for adverse reactions. Gait analysis showed that an SLS AFO was able to affect the gait of a healthy subject to reduce ankle plantarflexion during gait, which is the normal function to mitigate the dangers of drop foot. Using AM processes for custom orthotics components has been investigated for partial or full AFOs in varying degrees, mainly suggesting to use the SLS process with nylon 11 powder. At the time of writing, results have not been published for gait analysis of an adult who is ambulating with an AFO fabricated entirely from SLS nylon.

A modified scanning methodology was necessary to normalize the surfaces of the ankle-foot complex and minimize the variation in scan data. An opaque white nylon casting sock can stretch onto the appendage and almost completely remove all variations is skin tone, whilst decreases specular reflection and constraining the flesh. Potential problems from hair are thus also eliminated without having to shave the appendage. When stretched, the stocking adds a thickness of 0.25 mm to the skin surface.

The ankle-foot complex was in subtalar neutral referring to the relative orientation of the shank and foot. The posture of the lower extremities were slightly supine (leaning forward and supported) to allow the scanner to observe the ventral surface of the foot and posterior side of the leg in the same field of view. Scan anomalies and poor-fitting contours are removed by local curvature maximum comparison and Gaussian hole-filling algorithms for each individual point cloud. The clean point clouds are then merged into a single point cloud and a surface mesh is fitted. During a scan, data is captured which is relevant to the patient anatomy, as well as extraneous data from the environment and the orthotist's hands which must be removed. By creating a large contrast in color between the patient's anatomy and all other points the unwanted data may be removed according to range of hue & saturation for the voxel. The white balance from the patient's sock-covered appendage has a high contrast with the orthotist because of their blue gloves. Any surfaces occluded by the blue gloves cannot be registered from a scan, but may be added from a separate mesh captured when the practitioner's hands have moved to a different location on the patient's ankle.

A significant amount of subjective surface manipulation is required to develop the AFO shape model in both physical and digital processes. The modifications to the AFO digital scan still use the orthotist's instructions for location and offset distance of each region. 3D manipulation software like Rapidform has the capacity to perform surface overlay deviation analysis to compare the surface of the leg scan, with the cleaned, modified, and parameterized AFO digital model.

Figure 28A:
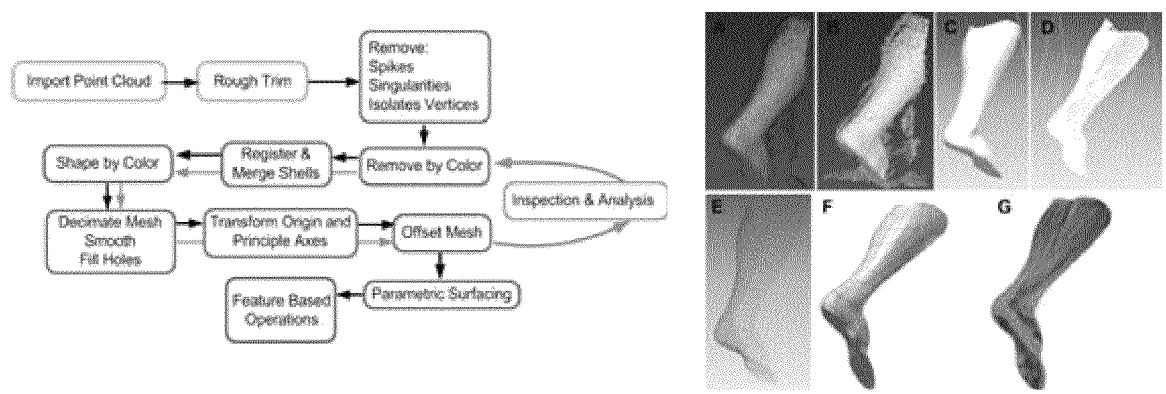
FIG. 28A illustrates the flow diagram of digital processes for point cloud refinement.

FIG. 28A illustrates the flow diagram of digital processes for point cloud refinement (AFO Digital Model Refinement Stages).

During each cleaning procedure it was important to evaluate by conducting inspection & analysis the continuity of the AFOs curvature plot to detect local irregularities. The surface mesh should ideally be a continuous smooth surface. Once the surface is well-behaved a patch of four sides NURBS model surfaces is fitted to the mesh in preparation for functioning as a CAD equation-driven feature reference. Once in CAD the surface may be referenced to offset features, thicken surfaces, create cavities, or extrude features.

A non-sensorized AFO using Polyamide Nylon 11 "Duraform PA" was fabricated to examine the process challenges using an SLS process to fabricate the AFO as well as its dynamic effects on a healthy subject's gait. Once the thermoplastic is fully sintered there is no inhalation hazard and can be autoclaved or washed. This material is rated as a United States Pharmacopeia (USP) Class VI biocompatible material, which poses no danger to superficial contact and can even be implanted within the body for up to 30 days. The mechanical properties of sintered nylon are within the range of extruded polypropylene materials currently employed by orthotists. Additionally, the thermoplastic materials used by both FDM and SLS may be selectively heated and their feature surfaces adjusted before the material re-cools and solidifies.

The trimline configuration and material thickness (3 mm) were set to match the semi-flexible polypropylene AFO. To optimize the mechanical material performance of the AFO and Z-axis, the build orientation was set to maximize the tensile yield point by aligning the horizontal datum along the Achilles. The AFO used was built in a P730 SLS system (EOS, Novi, Mich., USA). The height of this AFO was designed roughly 15% shorter than what would normally be prescribed in order to accommodate the SLS build platform available. Of the regions contacting the leg, the fit was comfortable.

Orthotists keep a detailed dialogue with each wearer and will usually have them ambulate for 20 minutes inside or near the clinic after donning a new AFO. Although a formal gait analysis is the most quantifiable assessment of benefit, even just ten minutes of casual gait reveals regions with problematic/uncomfortable fit. Locations and severity of blisters, pinching, swelling, or redness are all common indicators of the fit comfort.

The lateral trimlines set the level of rigidity in the AFO and are prescribed to the patient by an initial gait analysis. The slope and taper of the trimlines is assessed primarily qualitatively for the patient's needs. Two custom polypropylene AFOs were fabricated using the conventional process. AFO A is an off-the-shelf polypropylene posterior leaf spring orthosis and was sized from nearest available fit. AFOs B & C were fabricated based on trimline contours to give greater (flexible) freedom in dorsi & plantarflexion angle and less (semi-flexible) freedom for range of motion. The role of an AFO in gait is to allow a specified range of motion to increase gait symmetry and cadence range with maximum comfort and minimal increase in the wearer's energy expenditure. The trials in self-selected cadence, ankle range of motion and ankle energy was compared for gait between RP & traditional AFOs, both built custom for the wearer.

To characterize the gait pattern of the subject reflective markers placed with on the following specific anatomical landmarks of the subject's pelvis, and knee, ankle and foot of each leg. Additional markers were also rigidly attached to wands and placed over the mid-femur and mid-shank. The subject was instructed to ambulate along a 20 foot walkway at their self-selected comfortable speed for all of the walking trials. An 8-camera motion capture system recorded the three-dimensional trajectories of the reflective markers during the walking trials. Two force platforms embedded in the walkway surface recorded the three-dimensional ground reaction forces and moments during foot contacts onto the platforms.

The subject was a right-foot dominant healthy adult with no previous ambulatory or cognitive deficits and wore the AFOs on their right side. Four different conditions were tested during the gait evaluations: 1) with sneakers and no AFO (No AFO); 2) with the standard polypropylene posterior-leaf spring AFO (PP PLS); 3) with the flexible custom AFO (PP Flex), 4) and with the custom RP AFO (SLS RP). Each of the different AFOs was fitted to the right leg of the subject during the level walking trials. Five walking trials with foot contacts of each foot onto the force platforms were collected for each AFO condition.

Both ankle dorsi and plantarflexion angles are comparable with close standard deviations. Data from each brace condition was compared with characteristics of the right leg with No AFO. Range of motion for the SLS AFO exhibits comparable patterns and magnitudes to normal gait, as well as symmetry between the left and right ankle Dorsiflexion angle does not appear to be reduced as significantly as the other AFO conditions, although plantarflexion has decreased. Cadence was consistent between trials and comparable to gait with No AFO, indicating that this brace condition did not significantly inhibit ambulation.

Moments about the right ankle for No AFO matched magnitudes and temporal patterns with normal gait. For the PP PLS and PP Flex AFOs the shape of the moment curve matched the No AFO condition for peak location, but magnitudes have decreased by 24% and 18% respectively. Power generated at the ankle was significantly reduced for both PP PLS (84%) and PP Flex (57%), but exhibits the same patterns as healthy gait. This is as expected from the material resisting motion, which can also be a benefit to patients requiring increased stability during powered plantarflexion. Both AFOs show a higher standard deviation around peak power just prior to heel strike, again indicating an inconsistency in gait patterns. This may be due to greater compliance of the polypropylene material from which the standard AFO is made or a poorer fit of the AFO around the foot and ankle of the subject compared to the custom PP Flex AFO.

When comparing the two traditional (PP) AFOs they perform similarly in terms of controlling ankle kinematics and kinetics during the gait cycle, with some small deviations according to material and trim line. The SLS AFO has some small effects on gait, primarily in the peak ankle angles being reduced slightly but has a lesser impact than either of the PP versions or the off-the-shelf condition. The greatest likely contributing factor is because it is shorter than the other custom designs it is unable to hold and stiffen the ankle with its smaller moment arm. This is also seen in the graph for ankle power in the right side since it is not altering the power release of the ankle during toe-off as compared with the no AFO condition.

The process to build a SLS AFO was successful in comfort and had some biomechanics impacts, even at a reduced design height. If worn over a longer period of time, this smaller version would become uncomfortable because of the upper edge digging into the leg halfway along the Achilles. A pair of new AFOs was designed: a solid version with no channels and one instrumented with channels to receive the conductive polymer according to the described embodiments. The base design would be modified to match the actual polypropylene AFO in posterior height to have a relevant impact on gait, and have options for versions with and without the hollow tubes for the sensing silicone.

Even with the custom SLS version, there is need of a way to know at what stage of an AFO's lifespan it is currently in. By using the SLS process as the method of fabrication, there is relatively little overhead workload or complexity added by embedding sensing elements. The AFO may have begun to deform plastically without having significant visual impact or significant feel to the wearer. Serious injury such as falls or tripping can occur if it unexpectedly fails during use. Embedded sensors may offer clinicians and patients data on the state of the fatigued AFO over the course of its lifespan.

Figure 28B:
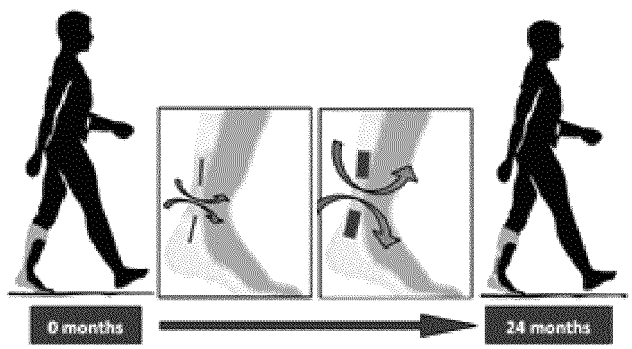
FIG. 28B shows the overview of the sensor and AFO functions interacting with the wearer.

FIG. 28B shows the overview of the sensor and AFO functions interacting with the wearer. At the initial state the AFO performs well to assist and stabilize the gait of the wearer. The range of electrical resistance (red lines) is initially a low magnitude range of strain (blue arrows). Over time the AFO mechanically fatigues, allowing the range of strain to increase. When the sensor resistance values pass a threshold to indicate plastic deformation of the AFO, it signals that it has reached the end of its safe operational life span and prompts the wearer to have it inspected or replaced. This also allows for iterating design and geometry changes as necessary based on patient feedback, biomechanical analysis of the device and its wearer, and analysis of the measurements taken over time by the embedded sensing elements. These iterations could mean modifying the thickness of the material, the trim lines indicating the edges of the material, locations of the embedded components, density of the material generated during the fabrication process, etc.

When compared to other available sensor types, the piezoresistive-based sensors constructed according to the described embodiments was the easiest to integrate because it could accommodate deformations which are too large for strain gages, while readily fitting into hollow cavities within the AFO material. An alternative used in SDM techniques is Fiber-Bragg Grating-sensors, which are an excellent strain-sensing choice free from electro-magnetic interference. The obstacle to using such technology in this application is inserting the glass tube through channels within the AFO. This entails conflicting requirements of maintaining a clearance gap between the glass and material body, yet to have no clearance gap to keep the sensitivity high. For redesign using the sensors of the described embodiments, material is removed in CAD to create the channel voids in order to make space available to fill with the conductive gel. The two versions of the SLS AFO were necessary to examine the biomechanics effect of removing this material as a tradeoff for sensing.

Figure 28C:
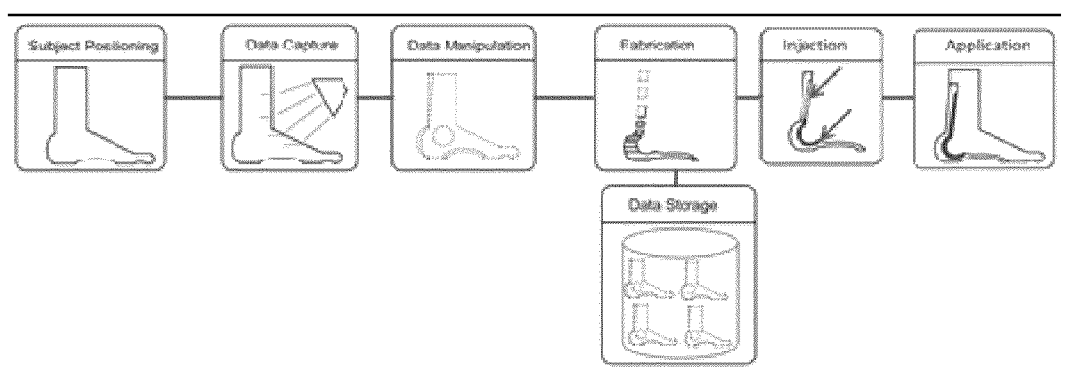
FIG. 28C illustrates a process diagram for creation, instrumentation, application and logging of a custom sensorized AFO.

Instrumenting the AFO builds on the process of generating an RP AFO via non-contact 3D scanning and stereolithography. FIG. 28C illustrates a process diagram for creation, instrumentation, application and logging of a custom sensorized AFO.

Determining the appropriate insertion sites is needed for early notification of AFO fatigue. Breakdown usually occurs around the base of the Achilles where the stress concentration is highest. A finite element model of the AFO geometry was examined in bending (using the torque and angle parameters from normative ambulatory data) to identify strain distribution. Simulations were examined for the AFO response to moments applied through the ankle joint at an axis parallel to the coronal plane. Using tetrahedral elements, a mesh of 49,717 nodes was generated in Cosmos (Dassault Systemes, Waltham, Mass., USA) for the FEA.

Simulation Limitations:
   The dominant motion of the ankle is in the sagittal plane so the analysis was performed flexing in this plane.
   Although the axis of rotation in the physical ankle alternates between dorsi and plantarflexion during gait, the axis of applied moment in the model remained normal to the sagittal plane.

Using the isotropic material properties of Nylon 11, loading was simulated to examine the way strain propagates through the posterior surfaces according to the magnitude of applied moment. Transferring the sensor geometry to the measurement sites in the AFO is selected according to the regions exhibiting mechanical strain within the sensing range. As the strain region expands and increases in magnitude, the edge of this embodiment should be close enough to register the strain without being stretched past its sensing saturation point of 0.0863 strains. The tube cross section of 2 mm was selected to ease injection with a larger diameter while retaining 0.5 mm wall thickness on either side of the AFO for build resolution.

Figure 29:
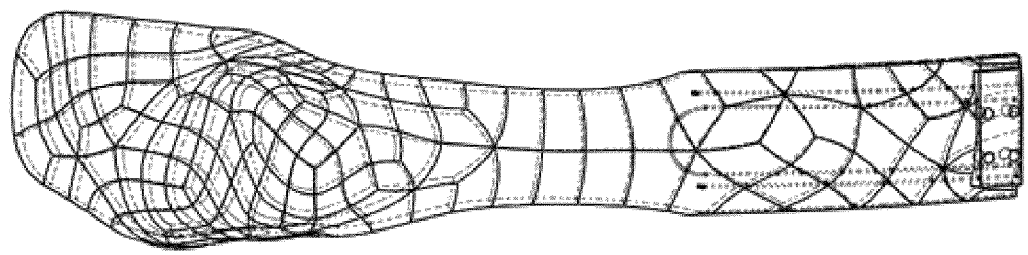
FIG. 29 illustrates the posterior view of AFO CAD.

Additional benefits of using CAD to design the AFOs is easily integrating mounting hardware and fixtures. Four mounting holes are built into the top to house electronics or attach an OEM cuff. This is chosen at the upper extremity of the shank support to avoid impacting the AFO stress distribution at the base of the Achilles where the sensor accuracy is most needed. Two sensing channel designs were included along the posterior reaching into the edge of the strain zone. The medial and lateral tabs were removed from the design to reduce build time and materials cost. The analysis conditions were also re-run to iterate the ending location of the channels. FIG. 29 illustrates the posterior view of AFO CAD with cavities (right edge) and calf tabs removed. Channel locations were updated using FEA from this new design.

Figure 30:
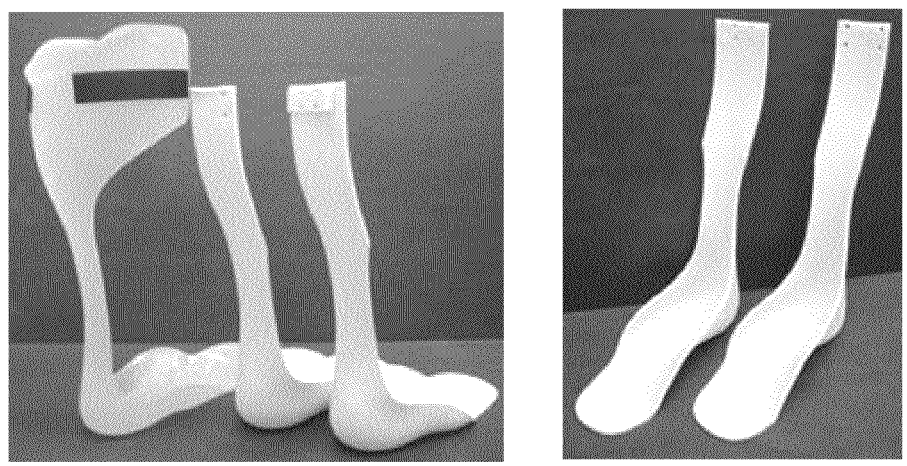
FIG. 30 provides a comparison of three AFOs.

After removal from the AM fabrication chamber, special attention was taken to clear out nylon powder material from the cavities and interior features for the sensors. Sensing and data transmission components are inserted into hollow cavities or attached via fasteners. The AFO surface was bead-blasted to remove clinging powder. FIG. 30 provides a comparison of three AFOs. The traditional polypropylene AFO, the non-instrumented SLS AFO, and the SLS AFO instrumented according to the described embodiments. The table below provides further comparison for the three AFOs.

| Physical Property | PP AFO | SLS AFO No Channels | SLS AFO With Channels |
|---|---|---|---|
| Mass (g) | 200 | 235 | 230 |
| Material Thickness (mm) | 2.3-3.63 | 4.1 | 4.1 |
| Height at posterior (cm) | 35.87 | 34.59 | 34.62 |
| Posterior Leaf Width Min (cm) | 4.16 | 5.18 | 5.18 |

Figure 31:
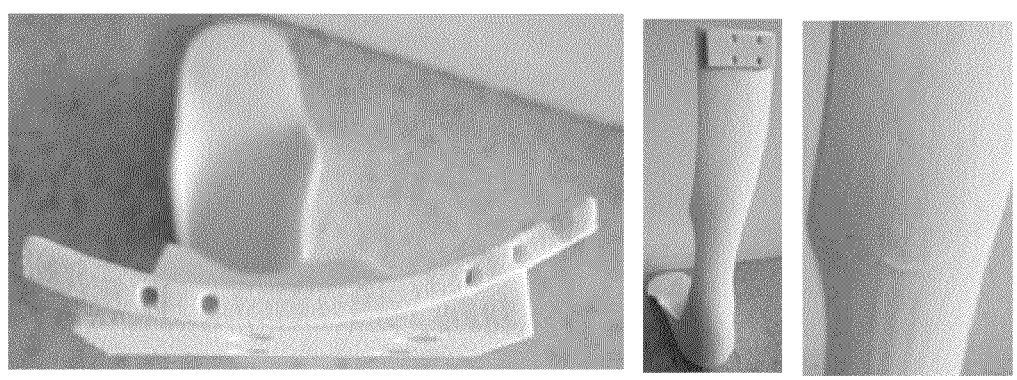
FIG. 31 shows the feature detail for the channel injection sites on the AFO instrumented according to the described embodiments.

FIG. 31 shows the feature detail for the channel injection sites on the AFO instrumented according to the described embodiments. The resolution of the hollow channels shows the interior along the AFO. The sensing channel acts in this case like the tensionned side of a cantilevered beam in bending.

Gait evaluation used a combination of IR motion capture and external load cells in the gait walkway. Each of the cameras of the Vicon system emit strobed IR light, which when reflected gives a grayscale view of each marker in 3D space. The co-ordinate of each marker is then calculated within the camera from triangulation of the markers and automatically tracks the markers to establish 3D trajectories using inverse kinematics. The procedure to record kinetic & kinematic characteristics consists of attachment of retro-reflective markers on key anatomical joint positions of the pelvis and lower extremities, and ambulating along the walkway registering one heel strike per foot per force platform. Reflective markers were placed on the pelvis and lower extremities using the same process as the first version of the SLS AFO. A static measurement was taken between each brace condition to account for any shifting of the markers. The AFOs were worn on the right leg as the 'affected side' with the left leg as the 'unaffected side'.

The gait kinetics and kinematics were recorded between four brace conditions:
   No AFO (sneaker gait)
   Traditional AFO
   SLS AFO with no Sensor Channels
   SLS AFO with Sensor Channels.

The traditional AFO was fabricated from polypropylene thermoplastic by an orthotist, aimed to provide flexible support and some resistance in dorsi and platarflexion. The two SLS versions were designed from a 3D scan according to similar trimlines of a semi-flexible PLS AFO. The goals of the baseline biomechanics testing were as follows:
   Establish baseline biomechanics effect of each AFO on gait when they are brand new
   Examine the magnitude of difference between the two SLS versions as attributed to the channels.

The gait pattern of the test subject has some graphs like ankle angle and ankle moment outside of the baseline measurements compared to the normal population data but is still considered to have a healthy gait. Temporal parameters for the trials are summarized in the table below.

The ankle angles are in greater dorsiflexion during heel strike and stance and less plantarflexion than the population, with peak toe-off at the average or higher end of normative data. The subject approaches heel strike with the ankle angles in more dorsiflexion than the normative population and has natural toe off roughly 5% later in the gait cycle. Possibly the subject takes larger steps than the normative population as shown by the heel strike and toe off angles of the sneaker (no AFO) gait. The natural difference between the left and right sides shows higher dorsi and plantarflexion angles for the right than the left side.

All brace conditions significantly decrease the plantarflexion range of motion in the right side, without significantly modifying the temporal pattern of the gait events. This is consistent with the effect of AFOs to prevent dropfoot. The peak angle during dorsiflexion stance is relatively unchanged between all AFO conditions but the angle during heel strike is decreased by 50% or more. Likewise, the peak knee angles for stance and swing are both markedly smaller during any of the brace conditions, likely because the stride length had decreased. All braces have similar effect on knee angle, with peak flexion taking place slightly later in the gait cycle (similarly with the subject's late toe off normal gait)

It is also possible that the unaffected (left) side has some compensatory strategies since the peak ankle plantarflexion angle increases when the contralateral side is wearing a brace, and the peak knee flexion angle also increases by 3-5°, but is not conclusive since this value is within the standard deviation of the trials collected.

Ankle moment for the unaffected side is relatively unchanged but still remains on the higher end of the normative population, with peak moment slightly higher than the standard deviation. The subject's right side has a natural increase in power at 20% through gait which is not entirely unusual [reference Neptune gait paper here] but is not seen in the normative population data. This bump becomes mitigated when wearing any of the AFOs, as well as peak moment also decreasing; possibly because of a slower walking velocity from wearing the braces. The table below illustrates peak gait values for right 'affected' side wearing AFOs.

| | | | Cadence (steps/min) | Walking Speed (m/s) | Opposite Foot Off (%) | Opposite Foot Contact (%) | Foot Off (%) | Stride Length (%) |
|---|---|---|---|---|---|---|---|---|
| No AFO | L | Avg | 101.57 | 1.19 | 12.26 | 48.52 | 62.90 | 1.41 |
| | | StDev | 1.71 | 0.03 | 0.99 | 0.31 | 0.30 | 0.01 |
| | R | Avg | 99.34 | 1.19 | 14.21 | 50.62 | 64.82 | 1.43 |
| | | StDev | 1.77 | 0.04 | 0.19 | 0.74 | 0.34 | 0.02 |
| Traditional | L | Avg | 94.76 | 1.08 | 13.42 | 49.21 | 63.82 | 1.36 |
| | | StDev | 1.76 | 0.05 | 0.62 | 0.29 | 0.40 | 0.03 |
| | R | Avg | 93.92 | 1.09 | 14.47 | 50.34 | 64.27 | 1.39 |
| | | StDev | 2.43 | 0.04 | 0.17 | 0.60 | 0.70 | 0.02 |
| Printed No Channels | L | Avg | 93.40 | 1.03 | 14.14 | 49.93 | 64.33 | 1.32 |
| | | StDev | 1.31 | 0.03 | 1.29 | 1.01 | 0.56 | 0.03 |
| | R | Avg | 94.01 | 1.07 | 14.49 | 50.39 | 63.97 | 1.36 |
| | | StDev | 1.18 | 0.01 | 0.43 | 0.63 | 0.42 | 0.02 |
| Printed with Channels | L | Avg | 94.99 | 1.06 | 12.93 | 49.87 | 63.98 | 1.34 |
| | | StDev | 0.56 | 0.02 | 0.64 | 0.44 | 0.40 | 0.03 |
| | R | Avg | 94.87 | 1.10 | 14.09 | 50.07 | 62.98 | 1.39 |
| | | StDev | 1.21 | 0.02 | 0.63 | 0.28 | 0.47 | 0.02 |

| Brace Condition | Ankle Angle (deg) | | Ankle Moment (Nm/kg) | Ankle Power During Stance (W/kg) | | Knee Angle (deg) | | Knee Moment (Nm/kg) |
|---|---|---|---|---|---|---|---|---|
| | Dorsi | Plant | Peak | Peak | Trough | Flex | Exten | Peak |
| Sneaker | 17.54 | 12.91 | 1.94 | 3.77 | 1.47 | 71.18 | 10.17 | 0.50 |
| Traditional AFO | 18.99 | 3.04 | 1.85 | 2.55 | 1.28 | 61.78 | 3.76 | 0.24 |
| SLS AFO - No sensor | 18.11 | 0.14 | 1.72 | 2.12 | 1.05 | 66.38 | 7.00 | 0.32 |
| SLS AFO - with sensor | 17.14 | 1.23 | 1.77 | 2.51 | 1.28 | 60.38 | 4.51 | 0.22 |

The two SLS AFOs have similar impact on ankle angles within 2° of each other to decrease peak dorsi and plantarflexion, and even have similar plantarflexion angle to the traditional version. The polypropylene is more flexible than the glass-filled Duraform EX, and its impact shows this difference in decreased heel strike and toe off angles. Peak knee angle in the right side for extension and flexion are similar, with the 'SLS sensor' version closer in effect to the traditional than the 'SLS non sensor'. The hollow cavities of the former will make the AFO slightly less stiff than if it were hollow. i.e. more closely approximate the more flexible traditional version. It is worth noting that although more flexible than the 'SLS non sensor' it is still stiffer than the traditional version, as indicated by peak plantarflexion angles during toe off between the three. In the contralateral side, knee angle and moment compensatory effects seem to be almost identical between the three brace conditions.

The impact on gait from the SLS AFOs was within the ranges of the traditional AFO for both legs. The version with hollow cavities to receive the polymer did behave with slightly more flexibly during peak angles but was a medium effect between the traditional and non-sensorized designs.

The ambulatory impact and mechanical state of the AFO can be assessed at the start and end of its anticipated lifespan. The parameters from the first gait analysis will be inputted to a motor controller in the AFO testbed to apply torque and wear down the AFO to simulate wear of up to 24 months of use. Adjustable clamps and platforms allow the axis of rotation of the testbed to be coincident with the AFO (about the base of the tibia bone). A hinged surrogate leg design is used to apply a moment profile the same way as the wearer's leg as in some similar other designs.

Strain gages bonded to the posterior surfaces coincident with the polymer sensor sites will all take periodic data to examine the strain state of the material, as well as compare the performance of the two sensor types. A rotary encoder inside the motor gearbox can measure AFO angle of dorsi/plantar flexion, and a load cell at the AFO/surrogate interface is able to measure interaction forces as it resists the loading.

Considering that the SLS AFO with hollow cavities performed in between the SLS solid and traditional versions it is feasible for it to match the mechanical properties of certain variants of traditional AFOs even with the material removed for the sensing material. With further characterization of its mechanical effects using the AFO testbed, it may be possible to approximate the impact of the traditional version more closely while also having the added benefit of sensors embedded inside it. The surface finish of the Nylon 12 is significantly rougher because of the glass beads, which poses challenges to injecting material over a channel running almost the entire length of the Achilles.

As a process for refining the advantages of an AFO build using AM techniques, combining the custom processes with modular design and adjustable fittings is a strategy considered for future work. The only custom-built regions are around the ankle which stabilizes the bony regions, while using off-the shelf solutions for the cuff which wraps around soft tissue. Finally, to offer a modular mechanical stiffness and spring return, an interchangeable load beam at the posterior connects the two regions.

Finally, to offer a modular mechanical stiffness and spring return, an interchangeable load beam at the posterior connects the two regions. This follows the design intent of "only custom build the bare minimum number of components.

The described embodiments may also utilize AM hardware that fabricates the electronics inside the parts as they are being built. For example, instrumentation that traditionally would be located remotely from the sensors could, at least in part, be embedded along with the sensor itself. Components such as amplifiers, filters, comparitors, buffers, and other such elements associated with data acquisition and measurement could be embedded.

Other embodiments may include the following improvements:

Particle Optimization Studies

The process to create the conductive elastomer merits refinement for particles with more uniform shape and size. This would improve repeatability and homogeneity of the volumetric resistivity. The tradeoff for higher density of conductive particles is a more brittle mechanical properties and lower elastic limit. Examining other types of formulations for elastic silicone could increase the elastic limit for a larger range of elastic deformation. Other types of silicone which have a smaller amount of solvent (reaction inhibitor) escaping could decrease the curing time.

Examine Alternative Materials which do not Contain Nickel

The current choice of using a conductive element which contains Nickel may not be used in some embodiments. Nickel has a non-linear gage factor which can be very challenging to model when back calculating the force from the transducer's response. In addition, there are questionable long-term health risks for using Nickel which should be avoided. Fine ground graphite powder in a silicone RTV suspension may be used in some embodiments. Additionally, graphite by itself is non-toxic and several conductive material combination have been presented made from bio-friendly and even household ingredients.

Increase the Number and Density of Sensing Channels

In some embodiments, linear and circular arrays of the same channel could increase the resolution of force sensing and improve detection of non-normal (tangential) loading on the sensor. Layers of matrices may increase the maximum force sensing saturation point by layering low-force (high strain) sensors on top of high-force (low strain) sensors to detect a similar ranges of forces but in a greater number of axes.

Sensing Layer for Protective Padding in Sports & Hazardous Work for the Wrist, Ankle, Neck, or Head.

In some embodiments, a thin AM layer of wearer-specific force sensors between the human and their exterior creates a sensing 'carapace' to detect impact forces as an early warning system for injury. A helmet may be instrumented with sensors to detect impact forces on particular locations of the skull for early warning of concussion or head trauma.

Pre Instrumented Components for Small Mobile Robots

Figure 32:
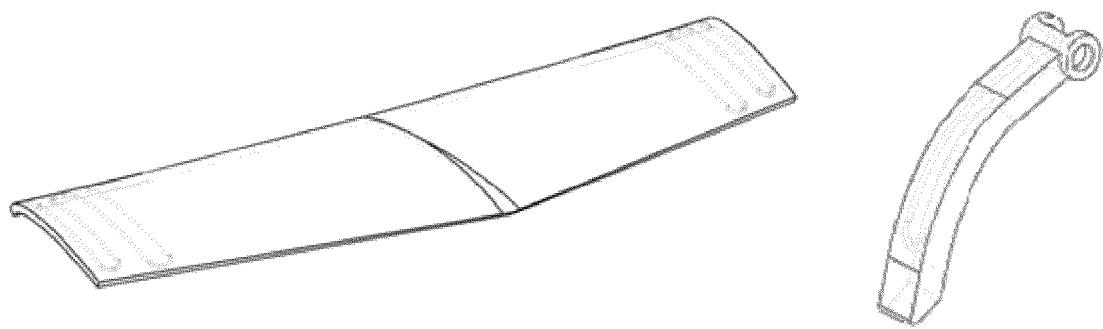
FIG. 32 illustrates a robot wing with an embedded strain sensing and a robotic leg with embedded sensors to detect impact from ground reactive forces.

Small flying/walking robots (as well as robotic devices) can be mission-customized for sensors and self-diagnostics in their end effectors, limbs, and internal mechanisms. A standard core unit with microcontroller, power, and communications can connect to these appendages which are mechanisms built on demand with sensors and electronics together. FIG. 32 illustrates a robot wing with an embedded strain sensing and a robotic leg with embedded sensors to detect impact from ground reactive forces. The described embedded sensors in robotic components could be extended to full size, non-robotic components, e.g., full sized airfoils on aircraft.

To monitor the state of limbs and manipulators in small robots, embedded sensors according to the described embodiments can help for detecting foot contact during locomotion when along the underside of the foot, or be contained within the body to detect damage in the limb after impacts, collisions or fails. A central controller in the body can be connected to the peripheral elements as if the mechanical structure is also a sensing structure, taking into account the range of motion of the limbs.

Thin airfoils can benefit from embedded sensors to monitor wind turbulence and health of the structures. The scale is meant for scale model aircraft or remote-controlled hobby size as opposed to a commercial airliner. The shape of airfoils is already a precisely-built freeform surface, by using additive methods to prototype the structure; sensors according to the described embodiments can give feedback to engineers for test models in the wind tunnels to validate the simulation models. The image shows the location of the sensors at the wing tips, this is an example of examining where the greatest strain would occur. For oscillations resulting from turbulent flow this could also be an indicator. For detecting undesired strain at other key locations like where the wing attaches to the aircraft body, the sensors of the described embodiments can warn in case plastic deformation is occurring in case of high loads.

Vibration Sensor Using a Mass on the End of a Catilevered Polymer Bridge

By affixing a mass on one end of a cantilevered beam, acceleration of the sensor will cause the polymer bridge to bend. The frequency and magnitude pattern of the strain induced from this bending can be back calculated for acceleration.

Patient-Specific Cuff to Connect with a Robotic Exoskeleton

The role of robotic exoskeletons in physical therapy is currently being explored. Their modes of operation in this field are still being examined, but regardless of the outcomes, a comfortable and secure patient-robot physical interface will be of great importance. The technology of the described embodiments can be used to generate instrumented patient-specific cuffs based off of a 3D scan of the area of interest. The areas below the knee and behind the thigh are popular choices for lower-limb interfaces since they have close contact to the bone and can generate the largest torques (respectively). The ankle-foot complex is used to mechanically ground the exoskeleton and can also benefit from embedded sensing to monitor the tissue compression and strain of the uprights connecting the robot.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of constructing a sensor, comprising:
   depositing a first material to form a structure comprising a plurality of consecutive layers each of which is a cross-sectional profile of a sensor design using additive manufacturing configured to support or sense a human body, wherein the depositing results in at least one void occurring within the structure;
   depositing a second material within at least one void, the second material having one or more electrical properties that vary according to deformation of the second material; and,
   providing electrical access to the second material to enable observation of the one or more electrical properties.

2. The method of claim 1, wherein the second material includes a conductive elastomer, and the one or more electrical properties includes piezoresistive properties.

3. The method of claim 2, wherein the second material includes a room temperature vulcanizing silicon suspension of electrically conductive particles.

4. The method of claim 3, wherein the electrically conductive particles include nickel-coated graphite particles.

5. The method of claim 1, wherein depositing the second material further includes injecting the second material through a port in the structure, the port providing access to the at least one void.

6. The method of claim 5, wherein the injecting is accomplished with a syringe, such that the syringe connects to the port through a coupler that is securely fastened to the syringe and the port.

7. The method of claim 6, wherein the coupler is a Leur lock having threads for coupling to the syringe.

8. The method of claim 1, wherein providing electrical access to the second material further includes attaching a first electrode to a first location on the second material and attaching a second electrode to a second location on the second material.

9. The method of claim 8, where the first location is a first end of the second material and the second location is a second end of the second material.

10. The method of claim 1, further including embedding one or more electrical components in the structure, wherein the one or more electrical components is electrically coupled to the second material.

11. The method of claim 10, wherein the one or more electrical components is selected from the group consisting of amplifier, filter, comparator, electrodes, voltage regulator, current regulator, sampler and buffer.

* * * * *